(12) United States Patent
Sakamoto et al.

(10) Patent No.: US 7,255,888 B2
(45) Date of Patent: Aug. 14, 2007

(54) METHOD OF IMPROVING TASTE AND/OR FLAVOUR OF FOODS AND BEVERAGES

(75) Inventors: Tomohiro Sakamoto, Kawasaki (JP); Nami Nakamura, Kawasaki (JP); Tomohiro Kodera, Kawasaki (JP); Noriki Nio, Kawasaki (JP); Noriaki Yamada, Kawasaki (JP); Hidehiko Wakabayashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/287,235

(22) Filed: Nov. 28, 2005

(65) Prior Publication Data

US 2006/0068056 A1    Mar. 30, 2006

Related U.S. Application Data

(63) Continuation of application No. PCT/JP04/07634, filed on May 26, 2004.

(30) Foreign Application Priority Data

May 27, 2003  (JP) ............................. 2003-148917

(51) Int. Cl.
*A23L 1/48* (2006.01)
*A23L 2/84* (2006.01)
*C12N 9/62* (2006.01)
*C12N 15/57* (2006.01)
*C12N 15/79* (2006.01)

(52) U.S. Cl. ............................. 426/7; 426/42; 426/52; 435/225; 435/252.3; 435/320.1; 536/23.2

(58) Field of Classification Search ..................... None
See application file for complete search history.

(56) References Cited

U.S. PATENT DOCUMENTS 6,303,359 B1 * 10/2001 Ninomiya et al. .......... 435/212
6,800,467 B1   10/2004 Blinkovsky et al.
6,902,887 B1 *  6/2005 Berka et al. .................. 435/6

FOREIGN PATENT DOCUMENTS

CN          1276012 A    12/2000
WO          WO9851804    11/1998

* cited by examiner

*Primary Examiner*—Kathleen Kerr Bragdon
*Assistant Examiner*—William W. Moore
(74) *Attorney, Agent, or Firm*—Oblon, Spivak, McClelland, Maier & Neustadt, P.C.

(57) ABSTRACT

The present invention discloses a method for producing foods and/or beverage having improved taste and/or flavour, comprising reacting a microbial aminopeptidase on a protein material optionally under the co-existence of a protease, wherein said aminopeptidase has the properties of: (a) having an activity of catalyzing the reaction of specifically releasing a glutamic acid and an aspartic acid from the N-terminal of a peptide and/or a protein; (b) having 50% or more activity at pH6.0-9.0 as compared with the activity at the optimum pH; (c) having 40% or more activity after heating at 25-60° C., pH7.5 for 30 minutes as compared with the activity of the non-heated enzyme; (d) having a molecular weight of about 40-60 kD as measured by SDS-PAGE and about 300-480 kD as measured by native-PAGE; (e) having a hydrolyzing activity of the aminopeptidase toward Glu-Glu dipeptide is 5 U/mg or more, preferably 10 U/mg or more.

15 Claims, 17 Drawing Sheets

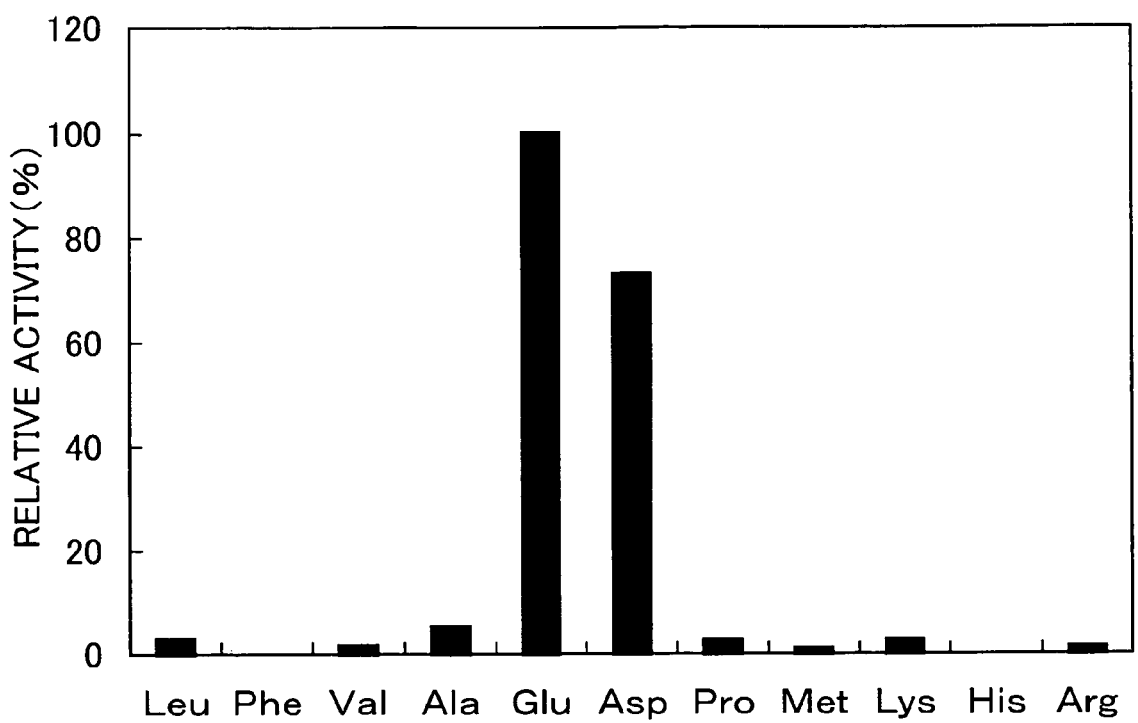
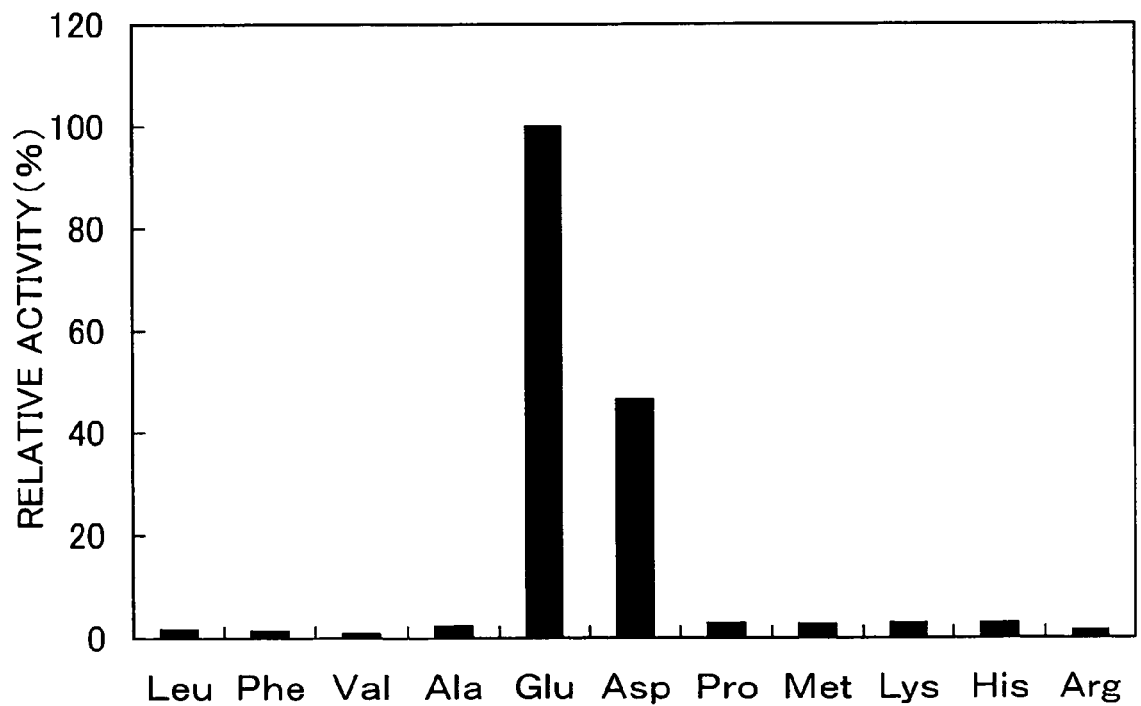

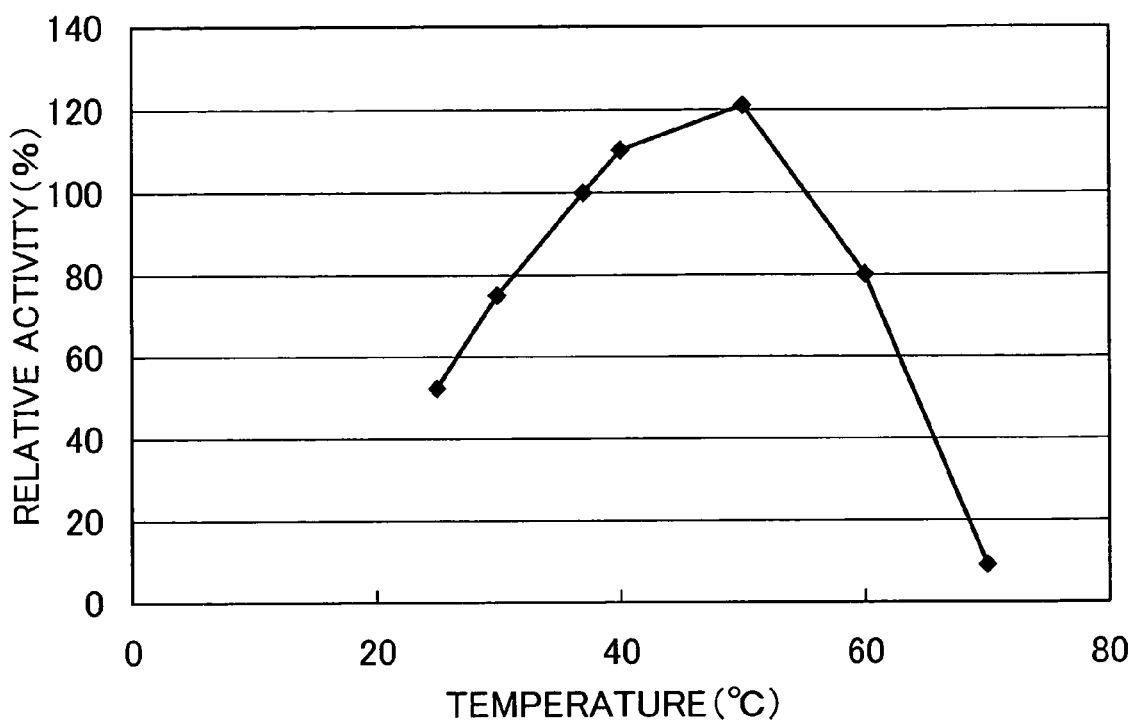
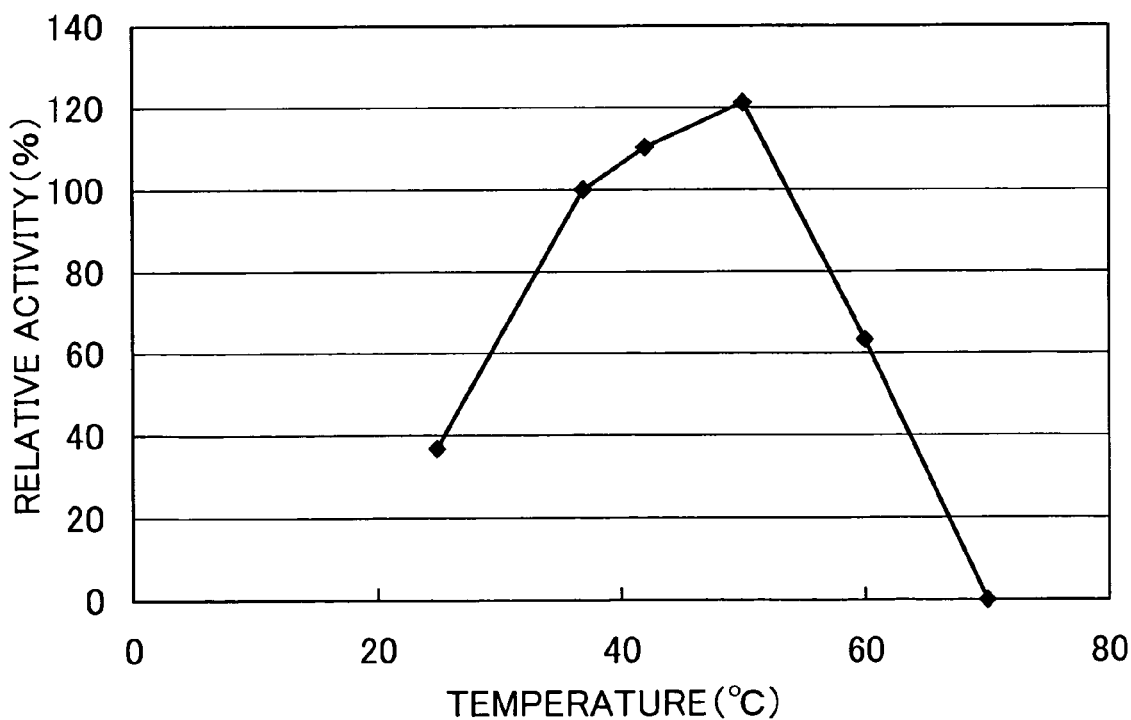

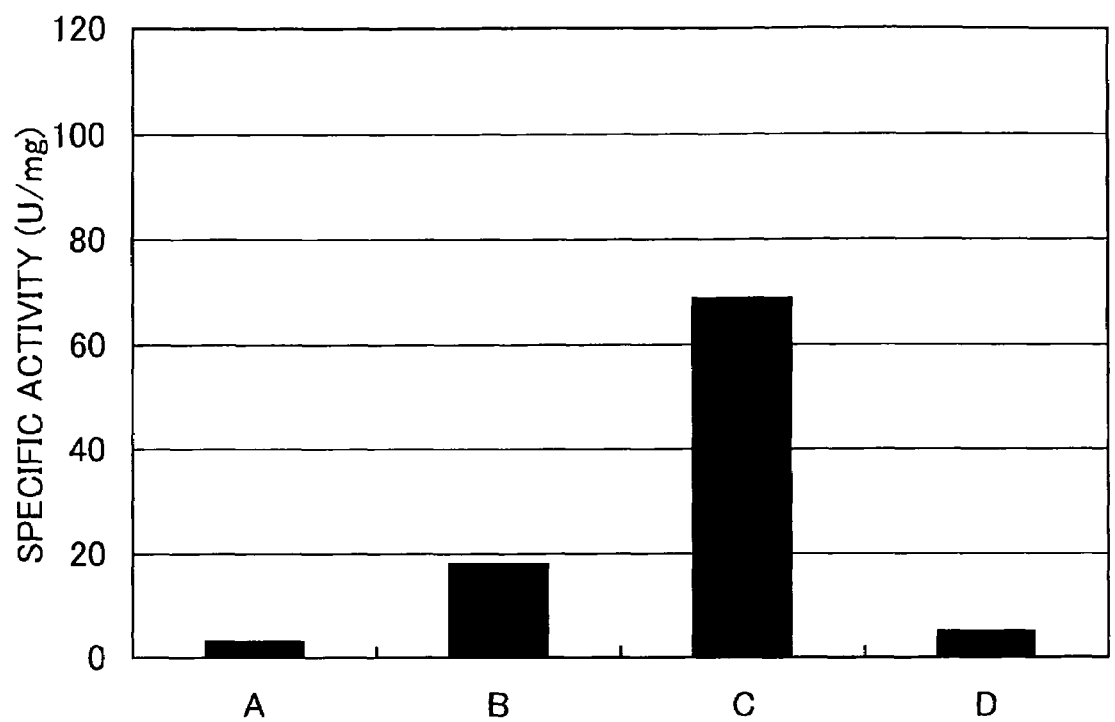
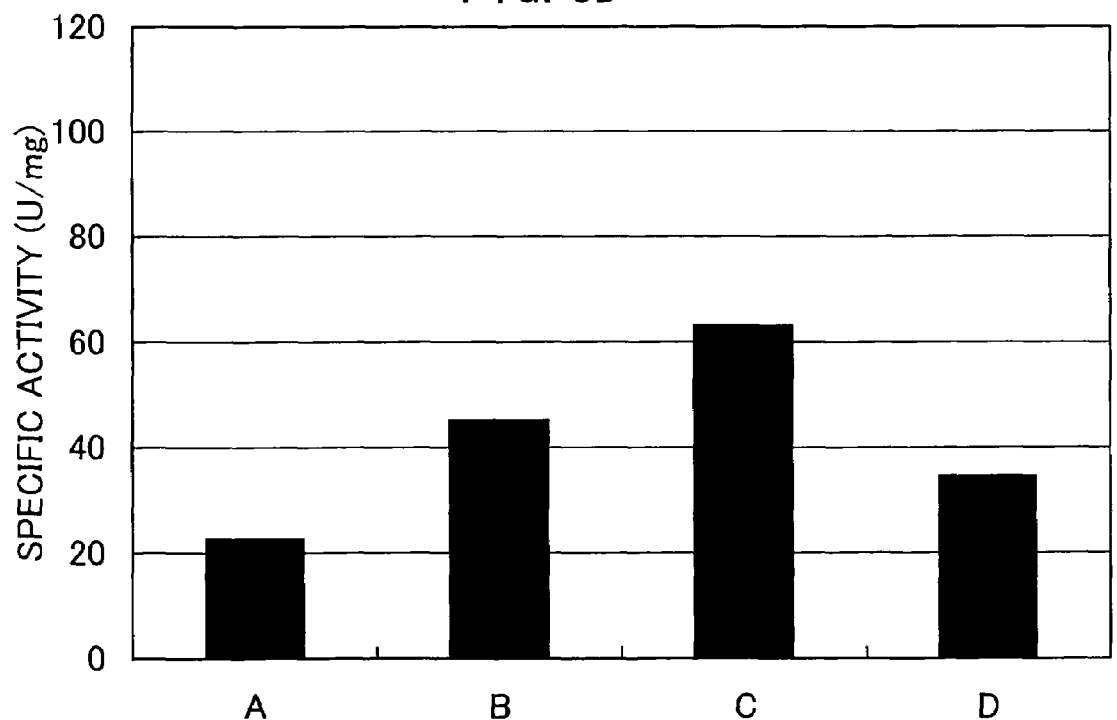

SEQUENCE LISTING

<160> NUMBER OF SEQ ID NOS: 40

<210> SEQ ID NO 1
<211> LENGTH: 1474
<212> TYPE: DNA
<213> ORGANISM: Aspergillus nidulance

<400> SEQUENCE: 1

```
atgcctctcc tactcccttt cacgccgtca attcggccag gaatctcctc gcaaatgcgg      60
gtttccaaga gatcaaggag aaagactcgt gggcttctac ttgccgccct ggtggaaaat     120
attacttgac tcgcaaccag tcaactatag tggctttcgc agttggcaag aaatggaagc     180
ctggaaatgc gatcgccatg atcggggctc acacggactc ccccgtgctg aggatcaagc     240
ccgttagtaa taaacgtggt gaaggttaca tccaagtcgg cgtcgagact tacggcggcg     300
gtatttggca tacttggttt gatcgtgatc ttggagttgc aggtcgcgcg atggttcgaa     360
cagacgacgg ttctattgtc caaaaactta tcaagattga tcgaccaatt ctccgcattc     420
cgacgttggc tatccatctg gagcgccagg agaccttctc tttcaataag gagactcaac     480
tgttccctat cgcaggcatg attgctgcgg aactaaaccg tactggccaa gccgagggtg     540
ccagcgacaa gagcaatacc gctgccgaga gcgagaatgc ggaattctct cccttgaaag     600
ctatcacaga gcgccaccac ccgcatattg tagagctcat cgctgccgag gcaggtgtgg     660
agccggccga tgtgcttgat tttgaaatga ttcttttcga tacgcaaaag tcctgcctag     720
gcggattgat ggaggagttt attttttctc cgcgtttgga caaccttaac agctccttct     780
gtgctacagc tggattgatc gagtctgtag ctgacgagtc agccctggac gacgaatcca     840
ccatccgtct tatcgctcta tttgaccacg aggaaattgg aagcaggacc gcacagggcg     900
ccgattctaa cgtccttccc ggcataatcc gccgtctgtc cgtcctgccc tctaccgctg     960
gcgatgtcga tacatcgacc gcttatgaac agactctgtc cacttctttc ctactctcgg    1020
ccgacatggc ccacgctgtt caccccaact ggtccgccaa gtatgaaaat gaccacaggc    1080
ctgaaattaa taaggggcca gtgatcaaga tcaatgccaa tgcacgctat gcgaccaact    1140
cccctggtat tgtgcttctc caggaagtcg cacgcaaggc tgtagagact gaaggcgaag    1200
```

```
gtgtcccgct acaactcttt gtcgttcgta acgattccag ctgtggaagc actatcggac    1260
ctatgctctc tgctgctcta ggggctcgga ccctagattt aggcaaccct cagctaagca    1320
tgcacagtat ccgcgagacg ggcgggacgt acgatgtggc gcacagtatc cgactcttca    1380
agagcttctt ccaacattac gccagcactt ctcaatcgat atttgtggat tagattctat    1440
tacgaggtag tgcgagggct agtgaatccc aaga                                1474

<210> SEQ ID NO 2
<211> LENGTH: 1494
<212> TYPE: DNA
<213> ORGANISM: Aspergillus nidulans
<220> FEATURE:
<221> NAME/KEY: CDS
<222> LOCATION: (1)..(1491)

<400> SEQUENCE: 2
```

| | | | | | | | | | | | | | | | | |
|---|---|---|---|---|---|---|---|---|---|---|---|---|---|---|---|---|
| atg | acg | tct | aat | cta | acg | aag | aat | ctc | aaa | cag | ccg | gcc | ctg | gac | ttc | 48 |
| Met | Thr | Ser | Asn | Leu | Thr | Lys | Asn | Leu | Lys | Gln | Pro | Ala | Leu | Asp | Phe | |
| 1 | | | | 5 | | | | | 10 | | | | | 15 | | |
| ttg | tcc | ttt | gtc | aat | gcc | tct | cct | act | ccc | ttt | cac | gcc | gtc | aat | tcg | 96 |
| Leu | Ser | Phe | Val | Asn | Ala | Ser | Pro | Thr | Pro | Phe | His | Ala | Val | Asn | Ser | |
| | | | 20 | | | | | 25 | | | | | 30 | | | |
| gcc | agg | aat | ctc | ctc | gca | aat | gcg | ggt | ttc | caa | gag | atc | aag | gag | aaa | 144 |
| Ala | Arg | Asn | Leu | Leu | Ala | Asn | Ala | Gly | Phe | Gln | Glu | Ile | Lys | Glu | Lys | |
| | | 35 | | | | | 40 | | | | | 45 | | | | |
| gac | tcg | tgg | gct | tct | act | tgc | cgc | cct | ggt | gga | aaa | tat | tac | ttg | act | 192 |
| Asp | Ser | Trp | Ala | Ser | Thr | Cys | Arg | Pro | Gly | Gly | Lys | Tyr | Tyr | Leu | Thr | |
| | 50 | | | | | 55 | | | | | 60 | | | | | |
| cgc | aac | cag | tca | act | ata | gtg | gct | ttc | gca | gtt | ggc | aag | aaa | tgg | aag | 240 |
| Arg | Asn | Gln | Ser | Thr | Ile | Val | Ala | Phe | Ala | Val | Gly | Lys | Lys | Trp | Lys | |
| 65 | | | | | 70 | | | | | 75 | | | | | 80 | |
| cct | gga | aat | gcg | atc | gcc | atg | atc | ggg | gct | cac | acg | gac | tcc | ccc | gtg | 288 |
| Pro | Gly | Asn | Ala | Ile | Ala | Met | Ile | Gly | Ala | His | Thr | Asp | Ser | Pro | Val | |
| | | | | 85 | | | | | 90 | | | | | 95 | | |
| ctg | agg | atc | aag | ccc | gtt | agt | aat | aaa | cgt | ggt | gaa | ggt | tac | atc | caa | 336 |
| Leu | Arg | Ile | Lys | Pro | Val | Ser | Asn | Lys | Arg | Gly | Glu | Gly | Tyr | Ile | Gln | |
| | | | 100 | | | | | 105 | | | | | 110 | | | |
| gtc | ggc | gtc | gag | act | tac | ggc | ggc | ggt | att | tgg | cat | act | tgg | ttt | gat | 384 |
| Val | Gly | Val | Glu | Thr | Tyr | Gly | Gly | Gly | Ile | Trp | His | Thr | Trp | Phe | Asp | |
| | | 115 | | | | | 120 | | | | | 125 | | | | |
| cgt | gat | ctt | gga | gtt | gca | ggt | cgc | gcg | atg | gtt | cga | aca | gac | gac | ggt | 432 |
| Arg | Asp | Leu | Gly | Val | Ala | Gly | Arg | Ala | Met | Val | Arg | Thr | Asp | Asp | Gly | |
| | 130 | | | | | 135 | | | | | 140 | | | | | |
| tct | att | gtc | caa | aaa | ctt | atc | aag | att | gat | cga | cca | att | ctc | cgc | att | 480 |
| Ser | Ile | Val | Gln | Lys | Leu | Ile | Lys | Ile | Asp | Arg | Pro | Ile | Leu | Arg | Ile | |
| 145 | | | | | 150 | | | | | 155 | | | | | 160 | |
| ccg | acg | ttg | gct | atc | cat | ctg | gag | cgc | cag | gag | acc | ttc | tct | ttc | aat | 528 |
| Pro | Thr | Leu | Ala | Ile | His | Leu | Glu | Arg | Gln | Glu | Thr | Phe | Ser | Phe | Asn | |
| | | | | 165 | | | | | 170 | | | | | 175 | | |
| aag | gag | act | caa | ctg | ttc | cct | atc | gca | ggc | atg | att | gct | gcg | gaa | cta | 576 |
| Lys | Glu | Thr | Gln | Leu | Phe | Pro | Ile | Ala | Gly | Met | Ile | Ala | Ala | Glu | Leu | |
| | | | 180 | | | | | 185 | | | | | 190 | | | |
| aac | cgt | act | ggc | caa | gcc | gag | ggt | gcc | agc | gac | aag | agc | aat | acc | gct | 624 |
| Asn | Arg | Thr | Gly | Gln | Ala | Glu | Gly | Ala | Ser | Asp | Lys | Ser | Asn | Thr | Ala | |
| | | 195 | | | | | 200 | | | | | 205 | | | | |
| gcc | gag | agc | gag | aat | gcg | gaa | ttc | tct | ccc | ttg | aaa | gct | atc | aca | gag | 672 |
| Ala | Glu | Ser | Glu | Asn | Ala | Glu | Phe | Ser | Pro | Leu | Lys | Ala | Ile | Thr | Glu | |
| | 210 | | | | | 215 | | | | | 220 | | | | | |
| cgc | cac | cac | ccg | cat | att | gta | gag | ctc | atc | gct | gcc | gag | gca | ggt | gtg | 720 |

-continued

```
Arg His His Pro His Ile Val Glu Leu Ile Ala Ala Glu Ala Gly Val
225                 230                 235                 240 gag ccg gcc gat gtg ctt gat ttt gaa atg att ctt ttc gat acg caa      768
Glu Pro Ala Asp Val Leu Asp Phe Glu Met Ile Leu Phe Asp Thr Gln
                245                 250                 255 aag tcc tgc cta ggc gga ttg atg gag gag ttt att ttt tct ccg cgt      816
Lys Ser Cys Leu Gly Gly Leu Met Glu Glu Phe Ile Phe Ser Pro Arg
        260                 265                 270 ttg gac aac ctt aac agc tcc ttc tgt gct aca gct gga ttg atc gag      864
Leu Asp Asn Leu Asn Ser Ser Phe Cys Ala Thr Ala Gly Leu Ile Glu
    275                 280                 285 tct gta gct gac gag tca gcc ctg gac gac gaa tcc acc atc cgt ctt      912
Ser Val Ala Asp Glu Ser Ala Leu Asp Asp Glu Ser Thr Ile Arg Leu
290                 295                 300 atc gct cta ttt gac cac gag gaa att gga agc agg acc gca cag ggc      960
Ile Ala Leu Phe Asp His Glu Glu Ile Gly Ser Arg Thr Ala Gln Gly
305                 310                 315                 320 gcc gat tct aac gtc ctt ccc ggc ata atc cgc cgt ctg tcc gtc ctg     1008
Ala Asp Ser Asn Val Leu Pro Gly Ile Ile Arg Arg Leu Ser Val Leu
                325                 330                 335 ccc tct acc gct ggc gat gtc gat aca tcg acc gct tat gaa cag act     1056
Pro Ser Thr Ala Gly Asp Val Asp Thr Ser Thr Ala Tyr Glu Gln Thr
            340                 345                 350 ctg tcc act tct ttc cta ctc tcg gcc gac atg gcc cac gct gtt cac     1104
Leu Ser Thr Ser Phe Leu Leu Ser Ala Asp Met Ala His Ala Val His
        355                 360                 365 ccc aac tgg tcc gcc aag tat gaa aat gac cac agg cct gaa att aat     1152
Pro Asn Trp Ser Ala Lys Tyr Glu Asn Asp His Arg Pro Glu Ile Asn
370                 375                 380 aag ggg cca gtg atc aag atc aat gcc aat gca cgc tat gcg acc aac     1200
Lys Gly Pro Val Ile Lys Ile Asn Ala Asn Ala Arg Tyr Ala Thr Asn
385                 390                 395                 400 tcc cct ggt att gtg ctt ctc cag gaa gtc gca cgc aag gct gta gag     1248
Ser Pro Gly Ile Val Leu Leu Gln Glu Val Ala Arg Lys Ala Val Glu
                405                 410                 415 act gaa ggc gaa ggt gtc ccg cta caa ctc ttt gtc gtt cgt aac gat     1296
Thr Glu Gly Glu Gly Val Pro Leu Gln Leu Phe Val Val Arg Asn Asp
            420                 425                 430 tcc agc tgt gga agc act atc gga cct atg ctc tct gct gct cta ggg     1344
Ser Ser Cys Gly Ser Thr Ile Gly Pro Met Leu Ser Ala Ala Leu Gly
        435                 440                 445 gct cgg acc cta gat tta ggc aac cct cag cta agc atg cac agt atc     1392
Ala Arg Thr Leu Asp Leu Gly Asn Pro Gln Leu Ser Met His Ser Ile
450                 455                 460 cgc gag acg ggc ggg acg tac gat gtg gcg cac agt atc cga ctc ttc     1440
Arg Glu Thr Gly Gly Thr Tyr Asp Val Ala His Ser Ile Arg Leu Phe
465                 470                 475                 480 aag agc ttc ttc caa cat tac gcc agc act tct caa tcg ata ttt gtg     1488
Lys Ser Phe Phe Gln His Tyr Ala Ser Thr Ser Gln Ser Ile Phe Val
                485                 490                 495 gat tag                                                              1494
Asp
```

<210> SEQ ID NO 3
<211> LENGTH: 497
<212> TYPE: PRT
<213> ORGANISM: Aspergillus nidulans

<400> SEQUENCE: 3

Met Thr Ser Asn Leu Thr Lys Asn Leu Lys Gln Pro Ala Leu Asp Phe

-continued

```
1               5                   10                  15
Leu Ser Phe Val Asn Ala Ser Pro Thr Pro Phe His Ala Val Asn Ser
                    20                  25                  30

Ala Arg Asn Leu Leu Ala Asn Ala Gly Phe Gln Glu Ile Lys Glu Lys
                    35                  40                  45

Asp Ser Trp Ala Ser Thr Cys Arg Pro Gly Gly Lys Tyr Tyr Leu Thr
        50                  55                  60

Arg Asn Gln Ser Thr Ile Val Ala Phe Ala Val Gly Lys Lys Trp Lys
65                      70                  75                  80

Pro Gly Asn Ala Ile Ala Met Ile Gly Ala His Thr Asp Ser Pro Val
                        85                  90                  95

Leu Arg Ile Lys Pro Val Ser Asn Lys Arg Gly Glu Gly Tyr Ile Gln
                    100                 105                 110

Val Gly Val Glu Thr Tyr Gly Gly Ile Trp His Thr Trp Phe Asp
                115                 120                 125

Arg Asp Leu Gly Val Ala Gly Arg Ala Met Val Arg Thr Asp Asp Gly
            130                 135                 140

Ser Ile Val Gln Lys Leu Ile Lys Ile Asp Arg Pro Ile Leu Arg Ile
145                     150                 155                 160

Pro Thr Leu Ala Ile His Leu Glu Arg Gln Glu Thr Phe Ser Phe Asn
                        165                 170                 175

Lys Glu Thr Gln Leu Phe Pro Ile Ala Gly Met Ile Ala Ala Glu Leu
                    180                 185                 190

Asn Arg Thr Gly Gln Ala Glu Gly Ala Ser Asp Lys Ser Asn Thr Ala
                195                 200                 205

Ala Glu Ser Glu Asn Ala Glu Phe Ser Pro Leu Lys Ala Ile Thr Glu
            210                 215                 220

Arg His His Pro His Ile Val Glu Leu Ile Ala Ala Glu Ala Gly Val
225                     230                 235                 240

Glu Pro Ala Asp Val Leu Asp Phe Glu Met Ile Leu Phe Asp Thr Gln
                        245                 250                 255

Lys Ser Cys Leu Gly Gly Leu Met Glu Glu Phe Ile Phe Ser Pro Arg
                    260                 265                 270

Leu Asp Asn Leu Asn Ser Ser Phe Cys Ala Thr Ala Gly Leu Ile Glu
                275                 280                 285

Ser Val Ala Asp Glu Ser Ala Leu Asp Asp Glu Ser Thr Ile Arg Leu
            290                 295                 300

Ile Ala Leu Phe Asp His Glu Glu Ile Gly Ser Arg Thr Ala Gln Gly
305                     310                 315                 320

Ala Asp Ser Asn Val Leu Pro Gly Ile Ile Arg Arg Leu Ser Val Leu
                        325                 330                 335

Pro Ser Thr Ala Gly Asp Val Asp Thr Ser Thr Ala Tyr Glu Gln Thr
                    340                 345                 350

Leu Ser Thr Ser Phe Leu Leu Ser Ala Asp Met Ala His Ala Val His
                355                 360                 365

Pro Asn Trp Ser Ala Lys Tyr Glu Asn Asp His Arg Pro Glu Ile Asn
            370                 375                 380

Lys Gly Pro Val Ile Lys Ile Asn Ala Asn Ala Arg Tyr Ala Thr Asn
385                     390                 395                 400

Ser Pro Gly Ile Val Leu Leu Gln Glu Val Ala Arg Lys Ala Val Glu
                        405                 410                 415

Thr Glu Gly Glu Gly Val Pro Leu Gln Leu Phe Val Val Arg Asn Asp
                    420                 425                 430
```

```
Ser Ser Cys Gly Ser Thr Ile Gly Pro Met Leu Ser Ala Ala Leu Gly
        435                 440                 445

Ala Arg Thr Leu Asp Leu Gly Asn Pro Gln Leu Ser Met His Ser Ile
    450                 455                 460

Arg Glu Thr Gly Gly Thr Tyr Asp Val Ala His Ser Ile Arg Leu Phe
465                 470                 475                 480

Lys Ser Phe Phe Gln His Tyr Ala Ser Thr Ser Gln Ser Ile Phe Val
                485                 490                 495

Asp

<210> SEQ ID NO 4
<211> LENGTH: 1854
<212> TYPE: DNA
<213> ORGANISM: Aspergillus oryzae

<400> SEQUENCE: 4
atgacttcga aaatcgccca aaatttgaag cagccggctc tggacttctt gtcctttgtc      60
aatgcttccc ccactcgtaa ctagctccct tcctatttgc gctcttggtc cacttatcta     120
actccggcca aattcagcct tccacgctgt ccaatcggca aggaacttc tgtcaaaggc      180
tggcttccag gagatcaagg tatgcgactc catttcagtg ttaactaaaa taataactgt     240
gtcttcagga gaaagattct tggtcctcca cttgtcgtcc ggtggaaag tattacctga      300
cccgtaatag ctcaaccatt gtggctttcg ctatcggcaa gaaatggaag gtatatacag     360
ataacaatcc gcacctgttc agcttttccc tctttgagac tgcaatgcta acagttatta     420
atgaaactaa gcctggaaac ccgatatcta tgatcggtgc ccacacggac tctcccgtgt     480
tgaggatcaa gcctgtcagc aacaagcgcg gcgaaggctt cgttcaagtt ggcgtggaga     540
cctacggtgg cggcatttgg cacacctgta atgaagttgt ccatcctctg ccgtgcgttg     600
catactaata agttctaggg ttcgaccgtg acttgggtgt cgcaggccgg gctatggtac     660
ggaccggtga cggctccatt gtgcagaagt tggtcaagat cgaccggccg agtatggttt     720
ccgcggaaca ttgacttgga taatatgtga ctgacatctt tcgcagttct ccgaatcccg     780
accttggcta tccaccttga tcgccaggag acttttgctt tcaataagga gacccaattg     840
ttccctatcg caggccttgt cgctgctgag ctgaaccgca ctgctgattc tactgcaact     900
ggcgaaaaga ccgcggcaaa caacgaaacg gagaaaggag actttgctcc actaaaatca     960
gtaaccgagc gtcatcaccc ctacttggtg gagcttattg ctgccgaagc aggagttaag    1020
ccggacgaca tcttggactt tgagatgatc ttgttcgaca ctcagaagtc ttgccttggt    1080
ggcttgctgg aggagttcgt tttctcgccc cgtctggata acctgaacag ctcgttctgt    1140
gccactgttg gactaatcga ctccgttgcc gatgcgtcgg cgctggacga tgaaccgtcc    1200
attcgtctca ttgcgttatt cgatcacgaa gagatcggca gccgtaccgc acagggagct    1260
gactcaaatg tgcttccggc aattatccgt cgcctgtctg ttctaccttc ttccacatct    1320
ggcaatgaag acttggctac tgcttttcgag gagactttgt cgacttcatt cctcctctct    1380
gcggacatgg ctcatgctgt ccacctaac tacgctgcta agtacgagaa tgatcaccga    1440
ccggagatca acaagggtcc tgtgatcaag atcaacgcca atgctcgcta cgcgacgaac    1500
tcccctggca ttgtcctact tcaggaggtt gcacgcaagg cagcagaaga cggtggagaa    1560
ggcgttcctc tccaactctt cgtcgttcgc aacgactcca gctgcggaag cacaattggt    1620
cccatgttgt ccgctcgcgct tggtgcccgc acgctggact tgggtaaccc acagctaagc    1680
```

-continued

```
atgcacagta tccgggagac tggtggtaca tatgatgttg ggcattctat tcggttgttc    1740
actagcttct tcaagcatta ctccaacacg tcaaagacaa tctttgttga ctgaagcgtt    1800
ggttacttgt gtagataggt atctatagaa aattgattgt ctatagagct caga          1854
```

<210> SEQ ID NO 5
<211> LENGTH: 1497
<212> TYPE: DNA
<213> ORGANISM: Aspergillus oryzae

<400> SEQUENCE: 5

```
atgacttcga aaatcgccca aaatttgaag cagccggctc tggacttctt gtcctttgtc      60
aatgcttccc ccactccctt ccacgctgtc aatcggcaa aggaacttct gtcaaaggct     120
ggcttccagg agatcaagga aaagattct tggtcctcca cttgtcgtcc cggtggaaag     180
tattacctga cccgtaatag ctcaaccatt gtggctttcg ctatcggcaa gaaatggaag    240
cctgaaaacc cgatatctat gatcggtgcc cacacggact ctcccgtgtt gaggatcaag    300
cctgtcagca caagcgcgg cgaaggcttc gttcaagttg gcgtggagac ctacggtggc    360
ggcatttggc acacctggtt cgaccgtgac ttgggtgtcg caggccgggc tatggtacgg    420
accggtgacg gctccattgt gcagaagttg gtcaagatcg accggccgat tctccgaatc    480
ccgaccttgg ctatccacct tgatcgccag gagacttttg ctttcaataa ggagacccaa    540
ttgttcccta tcgcaggcct tgtcgctgct gagctgaacc gcactgctga ttctactgca    600
actggcgaaa agaccgcggc aaacaacgaa acggagaaag gagactttgc tccactaaaa    660
tcagtaaccg agcgtcatca cccctacttg gtggagctta ttgctgccga agcaggagtt    720
aagccggacg acatcttgga ctttgagatg atcttgttcg acactcagaa gtcttgcctt    780
ggtggcttgc tggaggagtt cgttttctcg ccccgtctgg ataacctgaa cagctcgttc    840
tgtgccactg ttggactaat cgactccgtt gccgatgcgt cggcgctgga cgatgaaccg    900
tccattcgtc tcattgcgtt attcgatcac gaagagatcg gcagccgtac cgcacaggga    960
gctgactcaa atgtgcttcc ggcaattatc cgtcgcctgt ctgttctacc ttcttccaca   1020
tctggcaatg aagacttggc tactgctttc gaggagactt tgtcgacttc attcctcctc   1080
tctgcggaca tggctcatgc tgtccaccct aactacgctg ctaagtacga gaatgatcac   1140
cgaccggaga tcaacaaggg tcctgtgatc aagatcaacg ccaatgctcg ctacgcgacg   1200
aactcccctg gcattgtcct acttcaggag gttgcacgca aggcagcaga agacggtgga   1260
gaaggcgttc ctctccaact cttcgtcgtt cgcaacgact ccagctgcgg aagcacaatt   1320
ggtcccatgt tgtccgctgc gcttggtgcc cgcacgctgg acttgggtaa cccacagcta   1380
agcatgcaca gtatccggga gactggtggt acatatgatg ttgggcattc tattcggttg   1440
ttcactagct tcttcaagca ttactccaac acgtcaaaga caatctttgt tgactga      1497
```

<210> SEQ ID NO 6
<211> LENGTH: 1497
<212> TYPE: DNA
<213> ORGANISM: Aspergillus oryzae
<220> FEATURE:
<221> NAME/KEY: CDS
<222> LOCATION: (1)..(1494)

<400> SEQUENCE: 6

```
atg act tcg aaa atc gcc caa aat ttg aag cag ccg gct ctg gac ttc      48
Met Thr Ser Lys Ile Ala Gln Asn Leu Lys Gln Pro Ala Leu Asp Phe
1               5                   10                  15
```

```
ttg tcc ttt gtc aat gct tcc ccc act ccc ttc cac gct gtc caa tcg      96
Leu Ser Phe Val Asn Ala Ser Pro Thr Pro Phe His Ala Val Gln Ser
         20                  25                  30 gca aag gaa ctt ctg tca aag gct ggc ttc cag gag atc aag gag aaa     144
Ala Lys Glu Leu Leu Ser Lys Ala Gly Phe Gln Glu Ile Lys Glu Lys
             35                  40                  45 gat tct tgg tcc tcc act tgt cgt ccc ggt gga aag tat tac ctg acc     192
Asp Ser Trp Ser Ser Thr Cys Arg Pro Gly Gly Lys Tyr Tyr Leu Thr
 50                  55                  60 cgt aat agc tca acc att gtg gct ttc gct atc ggc aag aaa tgg aag     240
Arg Asn Ser Ser Thr Ile Val Ala Phe Ala Ile Gly Lys Lys Trp Lys
 65                  70                  75                  80 cct gga aac ccg ata tct atg atc ggt gcc cac acg gac tct ccc gtg     288
Pro Gly Asn Pro Ile Ser Met Ile Gly Ala His Thr Asp Ser Pro Val
                 85                  90                  95 ttg agg atc aag cct gtc agc aac aag cgc ggc gaa ggc ttc gtt caa     336
Leu Arg Ile Lys Pro Val Ser Asn Lys Arg Gly Glu Gly Phe Val Gln
            100                 105                 110 gtt ggc gtg gag acc tac ggt ggc ggc att tgg cac acc tgg ttc gac     384
Val Gly Val Glu Thr Tyr Gly Gly Gly Ile Trp His Thr Trp Phe Asp
        115                 120                 125 cgt gac ttg ggt gtc gca ggc cgg gct atg gta cgg acc ggt gac ggc     432
Arg Asp Leu Gly Val Ala Gly Arg Ala Met Val Arg Thr Gly Asp Gly
130                 135                 140 tcc att gtg cag aag ttg gtc aag atc gac cgg ccg att ctc cga atc     480
Ser Ile Val Gln Lys Leu Val Lys Ile Asp Arg Pro Ile Leu Arg Ile
145                 150                 155                 160 ccg acc ttg gct atc cac ctt gat cgc cag gag act ttt gct ttc aat     528
Pro Thr Leu Ala Ile His Leu Asp Arg Gln Glu Thr Phe Ala Phe Asn
                165                 170                 175 aag gag acc caa ttg ttc cct atc gca ggc ctt gtc gct gct gag ctg     576
Lys Glu Thr Gln Leu Phe Pro Ile Ala Gly Leu Val Ala Ala Glu Leu
            180                 185                 190 aac cgc act gct gat tct act gca act ggc gaa aag acc gcg gca aac     624
Asn Arg Thr Ala Asp Ser Thr Ala Thr Gly Glu Lys Thr Ala Ala Asn
        195                 200                 205 aac gaa acg gag aaa gga gac ttt gct cca cta aaa tca gta acc gag     672
Asn Glu Thr Glu Lys Gly Asp Phe Ala Pro Leu Lys Ser Val Thr Glu
210                 215                 220 cgt cat cac ccc tac ttg gtg gag ctt att gct gcc gaa gca gga gtt     720
Arg His His Pro Tyr Leu Val Glu Leu Ile Ala Ala Glu Ala Gly Val
225                 230                 235                 240 aag ccg gac gac atc ttg gac ttt gag atg atc ttg ttc gac act cag     768
Lys Pro Asp Asp Ile Leu Asp Phe Glu Met Ile Leu Phe Asp Thr Gln
                245                 250                 255 aag tct tgc ctt ggt ggc ttg ctg gag gag ttc gtt ttc tcg ccc cgt     816
Lys Ser Cys Leu Gly Gly Leu Leu Glu Glu Phe Val Phe Ser Pro Arg
            260                 265                 270 ctg gat aac ctg aac agc tcg ttc tgt gcc act gtt gga cta atc gac     864
Leu Asp Asn Leu Asn Ser Ser Phe Cys Ala Thr Val Gly Leu Ile Asp
        275                 280                 285 tcc gtt gcc gat gcg tcg gcg ctg gac gat gaa ccg tcc att cgt ctc     912
Ser Val Ala Asp Ala Ser Ala Leu Asp Asp Glu Pro Ser Ile Arg Leu
290                 295                 300 att gcg tta ttc gat cac gaa gag atc ggc agc cgt acc gca cag gga     960
Ile Ala Leu Phe Asp His Glu Glu Ile Gly Ser Arg Thr Ala Gln Gly
305                 310                 315                 320 gct gac tca aat gtg ctt ccg gca att atc cgt cgc ctg tct gtt cta    1008
Ala Asp Ser Asn Val Leu Pro Ala Ile Ile Arg Arg Leu Ser Val Leu
                325                 330                 335
```

```
cct tct tcc aca tct ggc aat gaa gac ttg gct act gct ttc gag gag    1056
Pro Ser Ser Thr Ser Gly Asn Glu Asp Leu Ala Thr Ala Phe Glu Glu
            340                 345                 350 act ttg tcg act tca ttc ctc ctc tct gcg gac atg gct cat gct gtc    1104
Thr Leu Ser Thr Ser Phe Leu Leu Ser Ala Asp Met Ala His Ala Val
        355                 360                 365 cac cct aac tac gct gct aag tac gag aat gat cac cga ccg gag atc    1152
His Pro Asn Tyr Ala Ala Lys Tyr Glu Asn Asp His Arg Pro Glu Ile
    370                 375                 380 aac aag ggt cct gtg atc aag atc aac gcc aat gct cgc tac gcg acg    1200
Asn Lys Gly Pro Val Ile Lys Ile Asn Ala Asn Ala Arg Tyr Ala Thr
385                 390                 395                 400 aac tcc cct ggc att gtc cta ctt cag gag gtt gca cgc aag gca gca    1248
Asn Ser Pro Gly Ile Val Leu Leu Gln Glu Val Ala Arg Lys Ala Ala
                405                 410                 415 gaa gac ggt gga gaa ggc gtt cct ctc caa ctc ttc gtc gtt cgc aac    1296
Glu Asp Gly Gly Glu Gly Val Pro Leu Gln Leu Phe Val Val Arg Asn
            420                 425                 430 gac tcc agc tgc gga agc aca att ggt ccc atg ttg tcc gct gcg ctt    1344
Asp Ser Ser Cys Gly Ser Thr Ile Gly Pro Met Leu Ser Ala Ala Leu
        435                 440                 445 ggt gcc cgc acg ctg gac ttg ggt aac cca cag cta agc atg cac agt    1392
Gly Ala Arg Thr Leu Asp Leu Gly Asn Pro Gln Leu Ser Met His Ser
    450                 455                 460 atc cgg gag act ggt ggt aca tat gat gtt ggg cat tct att cgg ttg    1440
Ile Arg Glu Thr Gly Gly Thr Tyr Asp Val Gly His Ser Ile Arg Leu
465                 470                 475                 480 ttc act agc ttc ttc aag cat tac tcc aac acg tca aag aca atc ttt    1488
Phe Thr Ser Phe Phe Lys His Tyr Ser Asn Thr Ser Lys Thr Ile Phe
                485                 490                 495 gtt gac tga                                                        1497
Val Asp

<210> SEQ ID NO 7
<211> LENGTH: 498
<212> TYPE: PRT
<213> ORGANISM: Aspergillus oryzae

<400> SEQUENCE: 7

Met Thr Ser Lys Ile Ala Gln Asn Leu Lys Gln Pro Ala Leu Asp Phe
1               5                   10                  15

Leu Ser Phe Val Asn Ala Ser Pro Thr Pro Phe His Ala Val Gln Ser
            20                  25                  30

Ala Lys Glu Leu Leu Ser Lys Ala Gly Phe Gln Glu Ile Lys Glu Lys
        35                  40                  45

Asp Ser Trp Ser Ser Thr Cys Arg Pro Gly Gly Lys Tyr Tyr Leu Thr
    50                  55                  60

Arg Asn Ser Ser Thr Ile Val Ala Phe Ala Ile Gly Lys Lys Trp Lys
65                  70                  75                  80

Pro Gly Asn Pro Ile Ser Met Ile Gly Ala His Thr Asp Ser Pro Val
                85                  90                  95

Leu Arg Ile Lys Pro Val Ser Asn Lys Arg Gly Glu Gly Phe Val Gln
            100                 105                 110

Val Gly Val Glu Thr Tyr Gly Gly Gly Ile Trp His Thr Trp Phe Asp
        115                 120                 125

Arg Asp Leu Gly Val Ala Gly Arg Ala Met Val Arg Thr Gly Asp Gly
    130                 135                 140
```

```
Ser Ile Val Gln Lys Leu Val Lys Ile Asp Arg Pro Ile Leu Arg Ile
145                 150                 155                 160

Pro Thr Leu Ala Ile His Leu Asp Arg Gln Glu Thr Phe Ala Phe Asn
                165                 170                 175

Lys Glu Thr Gln Leu Phe Pro Ile Ala Gly Leu Val Ala Ala Glu Leu
            180                 185                 190

Asn Arg Thr Ala Asp Ser Thr Ala Thr Gly Glu Lys Thr Ala Ala Asn
        195                 200                 205

Asn Glu Thr Glu Lys Gly Asp Phe Ala Pro Leu Lys Ser Val Thr Glu
    210                 215                 220

Arg His His Pro Tyr Leu Val Glu Leu Ile Ala Ala Glu Ala Gly Val
225                 230                 235                 240

Lys Pro Asp Asp Ile Leu Asp Phe Glu Met Ile Leu Phe Asp Thr Gln
                245                 250                 255

Lys Ser Cys Leu Gly Gly Leu Leu Glu Glu Phe Val Phe Ser Pro Arg
            260                 265                 270

Leu Asp Asn Leu Asn Ser Ser Phe Cys Ala Thr Val Gly Leu Ile Asp
        275                 280                 285

Ser Val Ala Asp Ala Ser Ala Leu Asp Asp Glu Pro Ser Ile Arg Leu
    290                 295                 300

Ile Ala Leu Phe Asp His Glu Glu Ile Gly Ser Arg Thr Ala Gln Gly
305                 310                 315                 320

Ala Asp Ser Asn Val Leu Pro Ala Ile Ile Arg Arg Leu Ser Val Leu
                325                 330                 335

Pro Ser Ser Thr Ser Gly Asn Glu Asp Leu Ala Thr Ala Phe Glu Glu
            340                 345                 350

Thr Leu Ser Thr Ser Phe Leu Leu Ser Ala Asp Met Ala His Ala Val
        355                 360                 365

His Pro Asn Tyr Ala Ala Lys Tyr Glu Asn Asp His Arg Pro Glu Ile
    370                 375                 380

Asn Lys Gly Pro Val Ile Lys Ile Asn Ala Asn Ala Arg Tyr Ala Thr
385                 390                 395                 400

Asn Ser Pro Gly Ile Val Leu Leu Gln Glu Val Ala Arg Lys Ala Ala
                405                 410                 415

Glu Asp Gly Gly Glu Gly Val Pro Leu Gln Leu Phe Val Val Arg Asn
            420                 425                 430

Asp Ser Ser Cys Gly Ser Thr Ile Gly Pro Met Leu Ser Ala Ala Leu
        435                 440                 445

Gly Ala Arg Thr Leu Asp Leu Gly Asn Pro Gln Leu Ser Met His Ser
    450                 455                 460

Ile Arg Glu Thr Gly Gly Thr Tyr Asp Val Gly His Ser Ile Arg Leu
465                 470                 475                 480

Phe Thr Ser Phe Phe Lys His Tyr Ser Asn Thr Ser Lys Thr Ile Phe
                485                 490                 495

Val Asp

<210> SEQ ID NO 8
<211> LENGTH: 1494
<212> TYPE: DNA
<213> ORGANISM: Aspergillus niger

<400> SEQUENCE: 8
atgacttcga aaatcgccca aaatttgaag cagccggctc tggacttctt gtcctttgtc    60
aatgcatctc ctaccccgtt ccatgccgtt cagtcggcaa aggaactcct tgccaaggct   120
```

-continued

```
ggcttccagg agatcaagga gaaggactct tgggcgtcaa cctgccggcc tggtggaaag     180
tactacttga cccgtaacca gtccaccatc atcgcttttg ctgtcggcaa gaaatggaag     240
cctggtaacc ccatttcgat gattggtgct cacaccgact ctcccgtcct cagagtcaag     300
ccggtcagca acaagcgcgg cgaaggatat gttcaggtcg gcgtagagac ttatggaggc     360
ggcatctggc acacctggtt cgaccgtgat ctgggtgttg caggtcgggc tatggtccgc     420
aatggcgacg gttcgatcgt gcagaagctg atcaagattg accgacccat tctccgcatt     480
cccactctgg ccattcatct ggaccgccag gagacttttg ccttcaacaa ggaaacacag     540
ctgttcccca tcgctggtct tgttgctgct gagctgaacc gtaccggtgc ctccgaggag     600
actgacaaag cggccaagga agccaacgag acaagggcg acttgtcgcc tctgaaggcc      660
atcactgagc gccaccaccc ttacctggtt gagctcattg ctgccgaagc cggtgtcaag     720
cccctcgatg tccttgactt cgagatgatt ctattcgata cccagaagtc gaacctgggt     780
ggactgctgg aggagttcat cttttcgcct cgcctggaca acctgaacag ctctttctgt     840
gccaccgtcg gcttgatcga ctctgtggct gactcctcag cgttggacga ggaacccgct     900
atccgtctca ttgccctctt tgaccacgag gaaatcggaa gccgcactgc tcagggtgcc     960
gactcgaaca tcctcccctc cgttatccgt cgcttgtccg tgctcccgtc gacggcaggc    1020
gctagtgacg acatcgccac tgcttacgag cagaccttgt ctacgtcttt ccttctgtct    1080
gctgatatgg cccatggagt ccacccgaat tacacggcca gtatgagaa cgaccaccgg     1140 ccccaaatca caagggccc tgttatcaag atcaacgcca acgcgcgcta tcgaccaac      1200 tcacccggta ttgttcttct tcaggaagtc gctcgcaagg ctggggaaga tgttggcgaa    1260
aaggttcccc tgcagctgtt tgttgtccgc aatgactcca gctgcggaag caccattggc    1320
ccaatgctgt ctgcggcgct tggcgctcgg acatcggatc tgggtaaccc ccagttgagc    1380
atgcacagta tccgtgagac gggaggtacc ctcgatgtgg cacactcgat ccgcctgttc    1440
actggattct tcaagcacta cgccaatctt tccaagacca tctttgttga ttag          1494
```

<210> SEQ ID NO 9
<211> LENGTH: 1494
<212> TYPE: DNA
<213> ORGANISM: Aspergillus niger
<220> FEATURE:
<221> NAME/KEY: CDS
<222> LOCATION: (1)..(1491)

<400> SEQUENCE: 9

```
atg act tcg aaa atc gcc caa aat ttg aag cag ccg gct ctg gac ttc    48
Met Thr Ser Lys Ile Ala Gln Asn Leu Lys Gln Pro Ala Leu Asp Phe
 1               5                  10                  15 ttg tcc ttt gtc aat gca tct cct acc ccg ttc cat gcc gtt cag tcg    96
Leu Ser Phe Val Asn Ala Ser Pro Thr Pro Phe His Ala Val Gln Ser
             20                  25                  30 gca aag gaa ctc ctt gcc aag gct ggc ttc cag gag atc aag gag aag   144
Ala Lys Glu Leu Leu Ala Lys Ala Gly Phe Gln Glu Ile Lys Glu Lys
         35                  40                  45 gac tct tgg gcg tca acc tgc cgg cct ggt gga aag tac tac ttg acc   192
Asp Ser Trp Ala Ser Thr Cys Arg Pro Gly Gly Lys Tyr Tyr Leu Thr
     50                  55                  60 cgt aac cag tcc acc atc atc gct ttt gct gtc ggc aag aaa tgg aag   240
Arg Asn Gln Ser Thr Ile Ile Ala Phe Ala Val Gly Lys Lys Trp Lys
 65                  70                  75                  80 cct ggt aac ccc att tcg atg att ggt gct cac acc gac tct ccc gtc   288
```

```
                Pro Gly Asn Pro Ile Ser Met Ile Gly Ala His Thr Asp Ser Pro Val
                                 85                  90                  95 ctc aga gtc aag ccg gtc agc aac aag cgc ggc gaa gga tat gtt cag          336
Leu Arg Val Lys Pro Val Ser Asn Lys Arg Gly Glu Gly Tyr Val Gln
                100                 105                 110 gtc ggc gta gag act tat gga ggc ggc atc tgg cac acc tgg ttc gac          384
Val Gly Val Glu Thr Tyr Gly Gly Gly Ile Trp His Thr Trp Phe Asp
                115                 120                 125 cgt gat ctg ggt gtt gca ggt cgg gct atg gtc cgc aat ggc gac ggt          432
Arg Asp Leu Gly Val Ala Gly Arg Ala Met Val Arg Asn Gly Asp Gly
        130                 135                 140 tcg atc gtg cag aag ctg atc aag att gac cga ccc att ctc cgc att          480
Ser Ile Val Gln Lys Leu Ile Lys Ile Asp Arg Pro Ile Leu Arg Ile
145                 150                 155                 160 ccc act ctg gcc att cat ctg gac cgc cag gag act ttt gcc ttc aac          528
Pro Thr Leu Ala Ile His Leu Asp Arg Gln Glu Thr Phe Ala Phe Asn
                    165                 170                 175 aag gaa aca cag ctg ttc ccc atc gct ggt ctt gtt gct gct gag ctg          576
Lys Glu Thr Gln Leu Phe Pro Ile Ala Gly Leu Val Ala Ala Glu Leu
                180                 185                 190 aac cgt acc ggt gcc tcc gag gag act gac aaa gcg gcc aag gaa gcc          624
Asn Arg Thr Gly Ala Ser Glu Glu Thr Asp Lys Ala Ala Lys Glu Ala
                195                 200                 205 aac gag gac aag ggc gac ttg tcg cct ctg aag gcc atc act gag cgc          672
Asn Glu Asp Lys Gly Asp Leu Ser Pro Leu Lys Ala Ile Thr Glu Arg
210                 215                 220 cac cac cct tac ctg gtt gag ctc att gct gcc gaa gcc ggt gtc aag          720
His His Pro Tyr Leu Val Glu Leu Ile Ala Ala Glu Ala Gly Val Lys
225                 230                 235                 240 ccc ctc gat gtc ctt gac ttc gag atg att cta ttc gat acc cag aag          768
Pro Leu Asp Val Leu Asp Phe Glu Met Ile Leu Phe Asp Thr Gln Lys
                    245                 250                 255 tcg aac ctg ggt gga ctg ctg gag gag ttc atc ttt tcg cct cgc ctg          816
Ser Asn Leu Gly Gly Leu Leu Glu Glu Phe Ile Phe Ser Pro Arg Leu
                260                 265                 270 gac aac ctg aac agc tct ttc tgt gcc acc gtc ggc ttg atc gac tct          864
Asp Asn Leu Asn Ser Ser Phe Cys Ala Thr Val Gly Leu Ile Asp Ser
                275                 280                 285 gtg gct gac tcc tca gcg ttg gac gag gaa ccc gct atc cgt ctc att          912
Val Ala Asp Ser Ser Ala Leu Asp Glu Glu Pro Ala Ile Arg Leu Ile
        290                 295                 300 gcc ctc ttt gac cac gag gaa atc gga agc cgc act gct cag ggt gcc          960
Ala Leu Phe Asp His Glu Glu Ile Gly Ser Arg Thr Ala Gln Gly Ala
305                 310                 315                 320 gac tcg aac atc ctc ccc tcc gtt atc cgt cgc ttg tcc gtg ctc ccg         1008
Asp Ser Asn Ile Leu Pro Ser Val Ile Arg Arg Leu Ser Val Leu Pro
                    325                 330                 335 tcg acg gca ggc gct agt gac gac atc gcc act gct tac gag cag acc         1056
Ser Thr Ala Gly Ala Ser Asp Asp Ile Ala Thr Ala Tyr Glu Gln Thr
                340                 345                 350 ttg tct acg tct ttc ctt ctg tct gct gat atg gcc cat gga gtc cac         1104
Leu Ser Thr Ser Phe Leu Leu Ser Ala Asp Met Ala His Gly Val His
                355                 360                 365 ccg aat tac acg gcc aag tat gag aac gac cac cgg ccc caa atc aac         1152
Pro Asn Tyr Thr Ala Lys Tyr Glu Asn Asp His Arg Pro Gln Ile Asn
        370                 375                 380 aag ggc cct gtt atc aag atc aac gcc aac gcg cgc tat gcg acc aac         1200
Lys Gly Pro Val Ile Lys Ile Asn Ala Asn Ala Arg Tyr Ala Thr Asn
385                 390                 395                 400
```

```
tca ccc ggt att gtt ctt ctt cag gaa gtc gct cgc aag gct ggg gaa    1248
Ser Pro Gly Ile Val Leu Leu Gln Glu Val Ala Arg Lys Ala Gly Glu
            405                 410                 415 gat gtt ggc gaa aag gtt ccc ctg cag ctg ttt gtt gtc cgc aat gac    1296
Asp Val Gly Glu Lys Val Pro Leu Gln Leu Phe Val Val Arg Asn Asp
        420                 425                 430 tcc agc tgc gga agc acc att ggc cca atg ctg tct gcg gcg ctt ggc    1344
Ser Ser Cys Gly Ser Thr Ile Gly Pro Met Leu Ser Ala Ala Leu Gly
    435                 440                 445 gct cgg aca tcg gat ctg ggt aac ccc cag ttg agc atg cac agt atc    1392
Ala Arg Thr Ser Asp Leu Gly Asn Pro Gln Leu Ser Met His Ser Ile
450                 455                 460 cgt gag acg gga ggt acc ctc gat gtg gca cac tcg atc cgc ctg ttc    1440
Arg Glu Thr Gly Gly Thr Leu Asp Val Ala His Ser Ile Arg Leu Phe
465                 470                 475                 480 act gga ttc ttc aag cac tac gcc aat ctt tcc aag acc atc ttt gtt    1488
Thr Gly Phe Phe Lys His Tyr Ala Asn Leu Ser Lys Thr Ile Phe Val
                485                 490                 495 gat tag                                                              1494
Asp
```

<210> SEQ ID NO 10
<211> LENGTH: 497
<212> TYPE: PRT
<213> ORGANISM: Aspergillus niger

<400> SEQUENCE: 10

```
Met Thr Ser Lys Ile Ala Gln Asn Leu Lys Gln Pro Ala Leu Asp Phe
1               5                   10                  15

Leu Ser Phe Val Asn Ala Ser Pro Thr Pro Phe His Ala Val Gln Ser
            20                  25                  30

Ala Lys Glu Leu Leu Ala Lys Ala Gly Phe Gln Glu Ile Lys Glu Lys
        35                  40                  45

Asp Ser Trp Ala Ser Thr Cys Arg Pro Gly Gly Lys Tyr Tyr Leu Thr
    50                  55                  60

Arg Asn Gln Ser Thr Ile Ile Ala Phe Ala Val Gly Lys Lys Trp Lys
65                  70                  75                  80

Pro Gly Asn Pro Ile Ser Met Ile Gly Ala His Thr Asp Ser Pro Val
                85                  90                  95

Leu Arg Val Lys Pro Val Ser Asn Lys Arg Gly Glu Gly Tyr Val Gln
            100                 105                 110

Val Gly Val Glu Thr Tyr Gly Gly Gly Ile Trp His Thr Trp Phe Asp
        115                 120                 125

Arg Asp Leu Gly Val Ala Gly Arg Ala Met Val Arg Asn Gly Asp Gly
    130                 135                 140

Ser Ile Val Gln Lys Leu Ile Lys Ile Asp Arg Pro Ile Leu Arg Ile
145                 150                 155                 160

Pro Thr Leu Ala Ile His Leu Asp Arg Gln Glu Thr Phe Ala Phe Asn
                165                 170                 175

Lys Glu Thr Gln Leu Phe Pro Ile Ala Gly Leu Val Ala Ala Glu Leu
            180                 185                 190

Asn Arg Thr Gly Ala Ser Glu Glu Thr Asp Lys Ala Ala Lys Glu Ala
        195                 200                 205

Asn Glu Asp Lys Gly Asp Leu Ser Pro Leu Lys Ala Ile Thr Glu Arg
    210                 215                 220

His His Pro Tyr Leu Val Glu Leu Ile Ala Ala Glu Ala Gly Val Lys
225                 230                 235                 240
```

Pro Leu Asp Val Leu Asp Phe Glu Met Ile Leu Phe Asp Thr Gln Lys
            245                 250                 255

Ser Asn Leu Gly Gly Leu Leu Glu Glu Phe Ile Phe Ser Pro Arg Leu
            260                 265                 270

Asp Asn Leu Asn Ser Ser Phe Cys Ala Thr Val Gly Leu Ile Asp Ser
            275                 280                 285

Val Ala Asp Ser Ser Ala Leu Asp Glu Glu Pro Ala Ile Arg Leu Ile
        290                 295                 300

Ala Leu Phe Asp His Glu Glu Ile Gly Ser Arg Thr Ala Gln Gly Ala
305                 310                 315                 320

Asp Ser Asn Ile Leu Pro Ser Val Ile Arg Arg Leu Ser Val Leu Pro
                325                 330                 335

Ser Thr Ala Gly Ala Ser Asp Asp Ile Ala Thr Ala Tyr Glu Gln Thr
            340                 345                 350

Leu Ser Thr Ser Phe Leu Leu Ser Ala Asp Met Ala His Gly Val His
            355                 360                 365

Pro Asn Tyr Thr Ala Lys Tyr Glu Asn Asp His Arg Pro Gln Ile Asn
370                 375                 380

Lys Gly Pro Val Ile Lys Ile Asn Ala Asn Ala Arg Tyr Ala Thr Asn
385                 390                 395                 400

Ser Pro Gly Ile Val Leu Leu Gln Glu Val Ala Arg Lys Ala Gly Glu
            405                 410                 415

Asp Val Gly Glu Lys Val Pro Leu Gln Leu Phe Val Val Arg Asn Asp
            420                 425                 430

Ser Ser Cys Gly Ser Thr Ile Gly Pro Met Leu Ser Ala Ala Leu Gly
            435                 440                 445

Ala Arg Thr Ser Asp Leu Gly Asn Pro Gln Leu Ser Met His Ser Ile
        450                 455                 460

Arg Glu Thr Gly Gly Thr Leu Asp Val Ala His Ser Ile Arg Leu Phe
465                 470                 475                 480

Thr Gly Phe Phe Lys His Tyr Ala Asn Leu Ser Lys Thr Ile Phe Val
                485                 490                 495

Asp

<210> SEQ ID NO 11
<211> LENGTH: 1473
<212> TYPE: DNA
<213> ORGANISM: Saccharomyces

<400> SEQUENCE: 11
atgttcagga tacaactgag aactatgtcc agcaaaacat gcaagagtga ttacccaaag      60
gagtttgtca gtttcttaaa tagctcacac tctccttacc atacagttca taacatcaaa     120
aagcatctgg tgtcaaatgg cttcaaagag ttgagcgaac gtgactcgtg ggctggccac     180
gtcgcacaaa aaggaaagta ctttgtgaca agaaatggct cttccattat tgcgtttgct     240
gttggtggaa gtgggagcc tggtaatcca attgccatta cgggtgctca caccgactcc     300
cccgcattaa ggattaagcc tatttctaaa agagtcagtg agaagtattt acaagtgggc     360
gtggaaactt atggtggcgc tatttggcat tcatggtttg ataaggattt gggcgttgcc     420
ggaagagttt tcgtaaagga tgcgaaaact ggcaaatcca ttgctagatt ggtggatttg     480
aatagacctc tgttaaagat tcctactttg gctattcatc tggacagaga cgtaaatcaa     540
aaattcgagt ttaatagaga aactcaactg ttgccgattg gtggtctgca agaagacaaa     600

-continued

```
actgaagcga aaactgaaaa ggaaattaat aacggtgagt ttacctccat aaaaacgata    660
gtacagaggc atcacgcaga acttttgggg ctaatagcca agaactcgc cattgataca     720 attgaagaca ttgaagactt cgaattgatc ctttatgatc ataatgcatc cactctaggt    780
gggttcaacg atgagtttgt cttctctggt cgattggata atttgacatc ttgtttcaca    840
tcaatgcacg gtttaacgtt ggcggctgac acagaaattg accgagaatc aggcattaga    900
ttgatggcat gctttgatca tgaggagatt ggctcatcct ccgcccaagg ggcagattct    960
aacttcttgc ctaatatatt ggaaaggttg tccatcctga aggggacgg ttctgatcaa    1020 actaaacctt tgtttcactc ggcaatattg gaaacttccg ctaagtcgtt tttcctttca   1080
tctgatgttg ctcatgcagt tcatccaaac tatgcaaaca aatacgaaag ccaacacaaa   1140 ccctttattgg gtggtggtcc cgtaatcaag attaacgcga atcaacgtta catgaccaat   1200
tcaccagggt tggtcttggt gaaaagacta gcagaggctg ctaaagtccc tttgcaattg   1260
tttgtcgtag ctaacgactc accatgcggt tctaccatcg gccccatttt ggcctcaaag   1320
acaggtatta gaactctaga cttgggtaat cctgtgttga gtatgcattc gattagagag   1380
accggtggct ctgcagacct ggagttccaa atcaagttat ttaaggaatt ttttgaacgc   1440
tacacttcca tagaatctga aattgttgtc taa                                1473
```

<210> SEQ ID NO 12
<211> LENGTH: 1473
<212> TYPE: DNA
<213> ORGANISM: Saccharomyces
<220> FEATURE:
<221> NAME/KEY: CDS
<222> LOCATION: (1)..(1470)

<400> SEQUENCE: 12

```
atg ttc agg ata caa ctg aga act atg tcc agc aaa aca tgc aag agt    48
Met Phe Arg Ile Gln Leu Arg Thr Met Ser Ser Lys Thr Cys Lys Ser
 1               5                  10                  15 gat tac cca aag gag ttt gtc agt ttc tta aat agc tca cac tct cct    96
Asp Tyr Pro Lys Glu Phe Val Ser Phe Leu Asn Ser Ser His Ser Pro
             20                  25                  30 tac cat aca gtt cat aac atc aaa aag cat ctg gtg tca aat ggc ttc    144
Tyr His Thr Val His Asn Ile Lys Lys His Leu Val Ser Asn Gly Phe
         35                  40                  45 aaa gag ttg agc gaa cgt gac tcg tgg gct ggc cac gtc gca caa aaa    192
Lys Glu Leu Ser Glu Arg Asp Ser Trp Ala Gly His Val Ala Gln Lys
     50                  55                  60 gga aag tac ttt gtg aca aga aat ggc tct tcc att att gcg ttt gct    240
Gly Lys Tyr Phe Val Thr Arg Asn Gly Ser Ser Ile Ile Ala Phe Ala
 65                  70                  75                  80 gtt ggt gga aag tgg gag cct ggt aat cca att gcc att acg ggt gct    288
Val Gly Gly Lys Trp Glu Pro Gly Asn Pro Ile Ala Ile Thr Gly Ala
                 85                  90                  95 cac acc gac tcc ccc gca tta agg att aag cct att tct aaa aga gtc    336
His Thr Asp Ser Pro Ala Leu Arg Ile Lys Pro Ile Ser Lys Arg Val
            100                 105                 110 agt gag aag tat tta caa gtg ggc gtg gaa act tat ggt ggc gct att    384
Ser Glu Lys Tyr Leu Gln Val Gly Val Glu Thr Tyr Gly Gly Ala Ile
        115                 120                 125 tgg cat tca tgg ttt gat aag gat ttg ggc gtt gcc gga aga gtt ttc    432
Trp His Ser Trp Phe Asp Lys Asp Leu Gly Val Ala Gly Arg Val Phe
    130                 135                 140 gta aag gat gcg aaa act ggc aaa tcc att gct aga ttg gtg gat ttg    480
Val Lys Asp Ala Lys Thr Gly Lys Ser Ile Ala Arg Leu Val Asp Leu
```

-continued

| | | | | | | | | | | | | | | | | |
|---|---|---|---|---|---|---|---|---|---|---|---|---|---|---|---|---|
| | | 145 | | | | 150 | | | | 155 | | | | 160 | | |
| aat | aga | cct | ctg | tta | aag | att | cct | act | ttg | gct | att | cat | ctg | gac | aga | 528 |
| Asn | Arg | Pro | Leu | Leu | Lys | Ile | Pro | Thr | Leu | Ala | Ile | His | Leu | Asp | Arg | |
| | | 165 | | | | 170 | | | | 175 | | | | | | |
| gac | gta | aat | caa | aaa | ttc | gag | ttt | aat | aga | gaa | act | caa | ctg | ttg | ccg | 576 |
| Asp | Val | Asn | Gln | Lys | Phe | Glu | Phe | Asn | Arg | Glu | Thr | Gln | Leu | Leu | Pro | |
| | | | 180 | | | | 185 | | | | 190 | | | | | |
| att | ggt | ggt | ctg | caa | gaa | gac | aaa | act | gaa | gcg | aaa | act | gaa | aag | gaa | 624 |
| Ile | Gly | Gly | Leu | Gln | Glu | Asp | Lys | Thr | Glu | Ala | Lys | Thr | Glu | Lys | Glu | |
| | | 195 | | | | 200 | | | | 205 | | | | | | |
| att | aat | aac | ggt | gag | ttt | acc | tcc | ata | aaa | acg | ata | gta | cag | agg | cat | 672 |
| Ile | Asn | Asn | Gly | Glu | Phe | Thr | Ser | Ile | Lys | Thr | Ile | Val | Gln | Arg | His | |
| 210 | | | | | 215 | | | | | 220 | | | | | | |
| cac | gca | gaa | ctt | ttg | ggg | cta | ata | gcc | aaa | gaa | ctc | gcc | att | gat | aca | 720 |
| His | Ala | Glu | Leu | Leu | Gly | Leu | Ile | Ala | Lys | Glu | Leu | Ala | Ile | Asp | Thr | |
| 225 | | | | | 230 | | | | | 235 | | | | | 240 | |
| att | gaa | gac | att | gaa | gac | ttc | gaa | ttg | atc | ctt | tat | gat | cat | aat | gca | 768 |
| Ile | Glu | Asp | Ile | Glu | Asp | Phe | Glu | Leu | Ile | Leu | Tyr | Asp | His | Asn | Ala | |
| | | | | 245 | | | | | 250 | | | | | 255 | | |
| tcc | act | cta | ggt | ggg | ttc | aac | gat | gag | ttt | gtc | ttc | tct | ggt | cga | ttg | 816 |
| Ser | Thr | Leu | Gly | Gly | Phe | Asn | Asp | Glu | Phe | Val | Phe | Ser | Gly | Arg | Leu | |
| | | | 260 | | | | | 265 | | | | | 270 | | | |
| gat | aat | ttg | aca | tct | tgt | ttc | aca | tca | atg | cac | ggt | tta | acg | ttg | gcg | 864 |
| Asp | Asn | Leu | Thr | Ser | Cys | Phe | Thr | Ser | Met | His | Gly | Leu | Thr | Leu | Ala | |
| | 275 | | | | | 280 | | | | | 285 | | | | | |
| gct | gac | aca | gaa | att | gac | cga | gaa | tca | ggc | att | aga | ttg | atg | gca | tgc | 912 |
| Ala | Asp | Thr | Glu | Ile | Asp | Arg | Glu | Ser | Gly | Ile | Arg | Leu | Met | Ala | Cys | |
| 290 | | | | | 295 | | | | | 300 | | | | | | |
| ttt | gat | cat | gag | gag | att | ggc | tca | tcc | tcc | gcc | caa | ggg | gca | gat | tct | 960 |
| Phe | Asp | His | Glu | Glu | Ile | Gly | Ser | Ser | Ser | Ala | Gln | Gly | Ala | Asp | Ser | |
| 305 | | | | | 310 | | | | | 315 | | | | | 320 | |
| aac | ttc | ttg | cct | aat | ata | ttg | gaa | agg | ttg | tcc | atc | ctg | aag | ggg | gac | 1008 |
| Asn | Phe | Leu | Pro | Asn | Ile | Leu | Glu | Arg | Leu | Ser | Ile | Leu | Lys | Gly | Asp | |
| | | | | 325 | | | | | 330 | | | | | 335 | | |
| ggt | tct | gat | caa | act | aaa | cct | ttg | ttt | cac | tcg | gca | ata | ttg | gaa | act | 1056 |
| Gly | Ser | Asp | Gln | Thr | Lys | Pro | Leu | Phe | His | Ser | Ala | Ile | Leu | Glu | Thr | |
| | | | 340 | | | | | 345 | | | | | 350 | | | |
| tcc | gct | aag | tcg | ttt | ttc | ctt | tca | tct | gat | gtt | gct | cat | gca | gtt | cat | 1104 |
| Ser | Ala | Lys | Ser | Phe | Phe | Leu | Ser | Ser | Asp | Val | Ala | His | Ala | Val | His | |
| | 355 | | | | | 360 | | | | | 365 | | | | | |
| cca | aac | tat | gca | aac | aaa | tac | gaa | agc | caa | cac | aaa | ccc | tta | ttg | ggt | 1152 |
| Pro | Asn | Tyr | Ala | Asn | Lys | Tyr | Glu | Ser | Gln | His | Lys | Pro | Leu | Leu | Gly | |
| 370 | | | | | 375 | | | | | 380 | | | | | | |
| ggt | ggt | ccc | gta | atc | aag | att | aac | gcg | aat | caa | cgt | tac | atg | acc | aat | 1200 |
| Gly | Gly | Pro | Val | Ile | Lys | Ile | Asn | Ala | Asn | Gln | Arg | Tyr | Met | Thr | Asn | |
| 385 | | | | | 390 | | | | | 395 | | | | | 400 | |
| tca | cca | ggg | ttg | gtc | ttg | gtg | aaa | aga | cta | gca | gag | gct | gct | aaa | gtc | 1248 |
| Ser | Pro | Gly | Leu | Val | Leu | Val | Lys | Arg | Leu | Ala | Glu | Ala | Ala | Lys | Val | |
| | | | | 405 | | | | | 410 | | | | | 415 | | |
| cct | ttg | caa | ttg | ttt | gtc | gta | gct | aac | gac | tca | cca | tgc | ggt | tct | acc | 1296 |
| Pro | Leu | Gln | Leu | Phe | Val | Val | Ala | Asn | Asp | Ser | Pro | Cys | Gly | Ser | Thr | |
| | | | 420 | | | | | 425 | | | | | 430 | | | |
| atc | ggc | ccc | att | ttg | gcc | tca | aag | aca | ggt | att | aga | act | cta | gac | ttg | 1344 |
| Ile | Gly | Pro | Ile | Leu | Ala | Ser | Lys | Thr | Gly | Ile | Arg | Thr | Leu | Asp | Leu | |
| | 435 | | | | | 440 | | | | | 445 | | | | | |
| ggt | aat | cct | gtg | ttg | agt | atg | cat | tcg | att | aga | gag | acc | ggt | ggc | tct | 1392 |
| Gly | Asn | Pro | Val | Leu | Ser | Met | His | Ser | Ile | Arg | Glu | Thr | Gly | Gly | Ser | |
| 450 | | | | | 455 | | | | | 460 | | | | | | |
| gca | gac | ctg | gag | ttc | caa | atc | aag | tta | ttt | aag | gaa | ttt | ttt | gaa | cgc | 1440 |

```
Ala Asp Leu Glu Phe Gln Ile Lys Leu Phe Lys Glu Phe Phe Glu Arg
465                 470                 475                 480 tac act tcc ata gaa tct gaa att gtt gtc taa                        1473
Tyr Thr Ser Ile Glu Ser Glu Ile Val Val
                485             490

<210> SEQ ID NO 13
<211> LENGTH: 490
<212> TYPE: PRT
<213> ORGANISM: Saccharomyces

<400> SEQUENCE: 13

Met Phe Arg Ile Gln Leu Arg Thr Met Ser Lys Thr Cys Lys Ser
1               5                   10                  15

Asp Tyr Pro Lys Glu Phe Val Ser Phe Leu Asn Ser Ser His Ser Pro
                20                  25                  30

Tyr His Thr Val His Asn Ile Lys Lys His Leu Val Ser Asn Gly Phe
                35                  40                  45

Lys Glu Leu Ser Glu Arg Asp Ser Trp Ala Gly His Val Ala Gln Lys
            50                  55                  60

Gly Lys Tyr Phe Val Thr Arg Asn Gly Ser Ser Ile Ile Ala Phe Ala
65                  70                  75                  80

Val Gly Gly Lys Trp Glu Pro Gly Asn Pro Ile Ala Ile Thr Gly Ala
                85                  90                  95

His Thr Asp Ser Pro Ala Leu Arg Ile Lys Pro Ile Ser Lys Arg Val
                100                 105                 110

Ser Glu Lys Tyr Leu Gln Val Gly Val Glu Thr Tyr Gly Gly Ala Ile
            115                 120                 125

Trp His Ser Trp Phe Asp Lys Asp Leu Gly Val Ala Gly Arg Val Phe
            130                 135                 140

Val Lys Asp Ala Lys Thr Gly Lys Ser Ile Ala Arg Leu Val Asp Leu
145                 150                 155                 160

Asn Arg Pro Leu Leu Lys Ile Pro Thr Leu Ala Ile His Leu Asp Arg
                165                 170                 175

Asp Val Asn Gln Lys Phe Glu Phe Asn Arg Glu Thr Gln Leu Leu Pro
                180                 185                 190

Ile Gly Gly Leu Gln Glu Asp Lys Thr Glu Ala Lys Thr Glu Lys Glu
            195                 200                 205

Ile Asn Asn Gly Glu Phe Thr Ser Ile Lys Thr Ile Val Gln Arg His
210                 215                 220

His Ala Glu Leu Leu Gly Leu Ile Ala Lys Glu Leu Ala Ile Asp Thr
225                 230                 235                 240

Ile Glu Asp Ile Glu Asp Phe Glu Leu Ile Leu Tyr Asp His Asn Ala
                245                 250                 255

Ser Thr Leu Gly Gly Phe Asn Asp Glu Phe Val Phe Ser Gly Arg Leu
            260                 265                 270

Asp Asn Leu Thr Ser Cys Phe Thr Ser Met His Gly Leu Thr Leu Ala
            275                 280                 285

Ala Asp Thr Glu Ile Asp Arg Glu Ser Gly Ile Arg Leu Met Ala Cys
            290                 295                 300

Phe Asp His Glu Glu Ile Gly Ser Ser Ala Gln Gly Ala Asp Ser
305                 310                 315                 320

Asn Phe Leu Pro Asn Ile Leu Glu Arg Leu Ser Ile Leu Lys Gly Asp
                325                 330                 335

Gly Ser Asp Gln Thr Lys Pro Leu Phe His Ser Ala Ile Leu Glu Thr
```

```
                    340               345               350
Ser Ala Lys Ser Phe Phe Leu Ser Ser Asp Val Ala His Ala Val His
            355                   360                   365
Pro Asn Tyr Ala Asn Lys Tyr Glu Ser Gln His Lys Pro Leu Leu Gly
        370                   375                   380
Gly Gly Pro Val Ile Lys Ile Asn Ala Asn Gln Arg Tyr Met Thr Asn
385                   390                   395                   400
Ser Pro Gly Leu Val Leu Val Lys Arg Leu Ala Glu Ala Ala Lys Val
                405                   410                   415
Pro Leu Gln Leu Phe Val Val Ala Asn Asp Ser Pro Cys Gly Ser Thr
            420                   425                   430
Ile Gly Pro Ile Leu Ala Ser Lys Thr Gly Ile Arg Thr Leu Asp Leu
        435                   440                   445
Gly Asn Pro Val Leu Ser Met His Ser Ile Arg Glu Thr Gly Gly Ser
    450                   455                   460
Ala Asp Leu Glu Phe Gln Ile Lys Leu Phe Lys Glu Phe Phe Glu Arg
465                   470                   475                   480
Tyr Thr Ser Ile Glu Ser Glu Ile Val Val
                485                   490

<210> SEQ ID NO 14
<211> LENGTH: 1263
<212> TYPE: DNA
<213> ORGANISM: Coryneform bacteria

<400> SEQUENCE: 14
atgcatgtaa ctgacgattt cttaagtttt attgccctaa gcccaagttc ctatcacgcg        60 gccgcgcgg tggagcgcag gttgctccat gaggggttca ttcgtcagga agataccgat       120
gaatgggatg cccgccctgg tgggcatgtg acggtgcgtg ggggagcagt agtggcgtgg       180
tgggtgcctg aggatgcttc gccagattcc gggttccgca tcattgggtc acatactgat       240
tcaccgggtt tcaagttaaa gccccgtggg gatctttcct cacacggttg gcagcaggcc       300
ggcgtcgagg tttacggcgg accgatcctg ccaagctggc tggatcgcga gctggcctta       360
gccggtcgca ttgtgcttgc cgacgggtcc gtcaagcttg tcaacaccgg cccgattctg       420
cgcatcccgc acgtggctat tcatttggac cgtactgtta ttcccaact cacccttaat       480 ccacagcgtc acctgcagcc tgtgtttgct gttggtgagc ccgacgtatc aattctggat       540
gtcattgctg tgctgcggt agtggatcct gcagatattg tcagccatga tctgatcacg       600
gtggctaccc aagatgctga agtatttggc gcacatgggg atttcttggc gtctggtcgc       660
ctggataacc tgagcagcgt gcatccatcc atgactgcat tgattgcggc ttcgcaatct       720
gacgatactg gttcggatat tttggttctt gctgcattcg atcatgaaga agtaggaagt       780
aattccacct cggtgccgg cggcccctg ttggaggatg tactcaaccg tactgctcgc       840
gcgttgggtg cagatgaaga tgagcgacgc cggatgttta accgttccac catggtctca       900
gctgacgcgg cacactccat tcaccccaac ttccccgaga gcatgatca gctaattac        960 cccatcattg gtaaaggtcc tgtattgaag gtcaacgcca accagcgcta cacctccgat      1020
gcagtcactt caggcatgtg gatcagggca tgtcagattg ccgtgtgcc acaccaggtg      1080 tttgccggca caacgatgt gccgtgtggt tccaccatcg gccgatcag tgcgactcgc      1140 ctgggtatcg attctgtcga tgtcggtatt ccattgctgt ccatgcactc cgcacgcgaa      1200
atggccggcg tgaaggatct gatgtggttt gaacaagccc tggaagccta tctggtaaat      1260
```

-continued

```
taa                                                                      1263
```

<210> SEQ ID NO 15
<211> LENGTH: 1263
<212> TYPE: DNA
<213> ORGANISM: Coryneform bactera
<220> FEATURE:
<221> NAME/KEY: CDS
<222> LOCATION: (1)..(1260)

<400> SEQUENCE: 15

```
atg cat gta act gac gat ttc tta agt ttt att gcc cta agc cca agt         48
Met His Val Thr Asp Asp Phe Leu Ser Phe Ile Ala Leu Ser Pro Ser
 1               5                  10                  15 tcc tat cac gcg gcc gcg gcg gtg gag cgc agg ttg ctc cat gag ggg         96
Ser Tyr His Ala Ala Ala Ala Val Glu Arg Arg Leu Leu His Glu Gly
             20                  25                  30 ttc att cgt cag gaa gat acc gat gaa tgg gat gcc cgc cct ggt ggg        144
Phe Ile Arg Gln Glu Asp Thr Asp Glu Trp Asp Ala Arg Pro Gly Gly
         35                  40                  45 cat gtg acg gtg cgt ggg gga gca gta gtg gcg tgg tgg gtg cct gag        192
His Val Thr Val Arg Gly Gly Ala Val Val Ala Trp Trp Val Pro Glu
     50                  55                  60 gat gct tcg cca gat tcc ggg ttc cgc atc att ggg tca cat act gat        240
Asp Ala Ser Pro Asp Ser Gly Phe Arg Ile Ile Gly Ser His Thr Asp
 65                  70                  75                  80 tca ccg ggt ttc aag tta aag ccc cgt ggg gat ctt tcc tca cac ggt        288
Ser Pro Gly Phe Lys Leu Lys Pro Arg Gly Asp Leu Ser Ser His Gly
                 85                  90                  95 tgg cag cag gcc ggc gtc gag gtt tac ggc gga ccg atc ctg cca agc        336
Trp Gln Gln Ala Gly Val Glu Val Tyr Gly Gly Pro Ile Leu Pro Ser
            100                 105                 110 tgg ctg gat cgc gag ctg gcc tta gcc ggt cgc att gtg ctt gcc gac        384
Trp Leu Asp Arg Glu Leu Ala Leu Ala Gly Arg Ile Val Leu Ala Asp
        115                 120                 125 ggg tcc gtc aag ctt gtc aac acc ggc ccg att ctg cgc atc ccg cac        432
Gly Ser Val Lys Leu Val Asn Thr Gly Pro Ile Leu Arg Ile Pro His
    130                 135                 140 gtg gct att cat ttg gac cgt act gtt aat tcc caa ctc acc ctt aat        480
Val Ala Ile His Leu Asp Arg Thr Val Asn Ser Gln Leu Thr Leu Asn
145                 150                 155                 160 cca cag cgt cac ctg cag cct gtg ttt gct gtt ggt gag ccc gac gta        528
Pro Gln Arg His Leu Gln Pro Val Phe Ala Val Gly Glu Pro Asp Val
                165                 170                 175 tca att ctg gat gtc att gct ggt gct gcg gta gtg gat cct gca gat        576
Ser Ile Leu Asp Val Ile Ala Gly Ala Ala Val Val Asp Pro Ala Asp
            180                 185                 190 att gtc agc cat gat ctg atc acg gtg gct acc caa gat gct gaa gta        624
Ile Val Ser His Asp Leu Ile Thr Val Ala Thr Gln Asp Ala Glu Val
        195                 200                 205 ttt ggc gca cat ggg gat ttc ttg gcg tct ggt cgc ctg gat aac ctg        672
Phe Gly Ala His Gly Asp Phe Leu Ala Ser Gly Arg Leu Asp Asn Leu
    210                 215                 220 agc agc gtg cat cca tcc atg act gca ttg att gcg gct tcg caa tct        720
Ser Ser Val His Pro Ser Met Thr Ala Leu Ile Ala Ala Ser Gln Ser
225                 230                 235                 240 gac gat act ggt tcg gat att ttg gtt ctt gct gca ttc gat cat gaa        768
Asp Asp Thr Gly Ser Asp Ile Leu Val Leu Ala Ala Phe Asp His Glu
                245                 250                 255 gaa gta gga agt aat tcc acc tcg ggt gcc ggc ggc ccc ctg ttg gag        816
Glu Val Gly Ser Asn Ser Thr Ser Gly Ala Gly Gly Pro Leu Leu Glu
```

-continued

```
                     260                 265                 270
gat gta ctc aac cgt act gct cgc gcg ttg ggt gca gat gaa gat gag      864
Asp Val Leu Asn Arg Thr Ala Arg Ala Leu Gly Ala Asp Glu Asp Glu
        275                 280                 285 cga cgc cgg atg ttt aac cgt tcc acc atg gtc tca gct gac gcg gca      912
Arg Arg Arg Met Phe Asn Arg Ser Thr Met Val Ser Ala Asp Ala Ala
290                 295                 300 cac tcc att cac ccc aac ttc ccc gag aag cat gat caa gct aat tac      960
His Ser Ile His Pro Asn Phe Pro Glu Lys His Asp Gln Ala Asn Tyr
305                 310                 315                 320 ccc atc att ggt aaa ggt cct gta ttg aag gtc aac gcc aac cag cgc     1008
Pro Ile Ile Gly Lys Gly Pro Val Leu Lys Val Asn Ala Asn Gln Arg
            325                 330                 335 tac acc tcc gat gca gtc act tca ggc atg tgg atc agg gca tgt cag     1056
Tyr Thr Ser Asp Ala Val Thr Ser Gly Met Trp Ile Arg Ala Cys Gln
            340                 345                 350 att gcc ggt gtg cca cac cag gtg ttt gcc ggc aac aac gat gtg ccg     1104
Ile Ala Gly Val Pro His Gln Val Phe Ala Gly Asn Asn Asp Val Pro
            355                 360                 365 tgt ggt tcc acc atc ggc ccg atc agt gcg act cgc ctg ggt atc gat     1152
Cys Gly Ser Thr Ile Gly Pro Ile Ser Ala Thr Arg Leu Gly Ile Asp
370                 375                 380 tct gtc gat gtc ggt att cca ttg ctg tcc atg cac tcc gca cgc gaa     1200
Ser Val Asp Val Gly Ile Pro Leu Leu Ser Met His Ser Ala Arg Glu
385                 390                 395                 400 atg gcc ggc gtg aag gat ctg atg tgg ttt gaa caa gcc ctg gaa gcc     1248
Met Ala Gly Val Lys Asp Leu Met Trp Phe Glu Gln Ala Leu Glu Ala
                405                 410                 415 tat ctg gta aat taa                                                  1263
Tyr Leu Val Asn
            420

<210> SEQ ID NO 16
<211> LENGTH: 420
<212> TYPE: PRT
<213> ORGANISM: Coryneform bactera

<400> SEQUENCE: 16

Met His Val Thr Asp Asp Phe Leu Ser Phe Ile Ala Leu Ser Pro Ser
1               5                   10                  15

Ser Tyr His Ala Ala Ala Val Glu Arg Arg Leu Leu His Glu Gly
            20                  25                  30

Phe Ile Arg Gln Glu Asp Thr Asp Glu Trp Asp Ala Arg Pro Gly Gly
        35                  40                  45

His Val Thr Val Arg Gly Gly Ala Val Val Ala Trp Trp Val Pro Glu
    50                  55                  60

Asp Ala Ser Pro Asp Ser Gly Phe Arg Ile Ile Gly Ser His Thr Asp
65                  70                  75                  80

Ser Pro Gly Phe Lys Leu Lys Pro Arg Gly Asp Leu Ser Ser His Gly
                85                  90                  95

Trp Gln Gln Ala Gly Val Glu Val Tyr Gly Gly Pro Ile Leu Pro Ser
            100                 105                 110

Trp Leu Asp Arg Glu Leu Ala Leu Ala Gly Arg Ile Val Leu Ala Asp
        115                 120                 125

Gly Ser Val Lys Leu Val Asn Thr Gly Pro Ile Leu Arg Ile Pro His
    130                 135                 140

Val Ala Ile His Leu Asp Arg Thr Val Asn Ser Gln Leu Thr Leu Asn
145                 150                 155                 160
```

```
Pro Gln Arg His Leu Gln Pro Val Phe Ala Val Gly Glu Pro Asp Val
            165                 170                 175
Ser Ile Leu Asp Val Ile Ala Gly Ala Ala Val Val Asp Pro Ala Asp
            180                 185                 190
Ile Val Ser His Asp Leu Ile Thr Val Ala Thr Gln Asp Ala Glu Val
            195                 200                 205
Phe Gly Ala His Gly Asp Phe Leu Ala Ser Gly Arg Leu Asp Asn Leu
            210                 215                 220
Ser Ser Val His Pro Ser Met Thr Ala Leu Ile Ala Ala Ser Gln Ser
225                 230                 235                 240
Asp Asp Thr Gly Ser Asp Ile Leu Val Leu Ala Ala Phe Asp His Glu
                245                 250                 255
Glu Val Gly Ser Asn Ser Thr Ser Gly Ala Gly Pro Leu Leu Glu
                260                 265                 270
Asp Val Leu Asn Arg Thr Ala Arg Ala Leu Gly Ala Asp Glu Asp Glu
                275                 280                 285
Arg Arg Arg Met Phe Asn Arg Ser Thr Met Val Ser Ala Asp Ala Ala
290                 295                 300
His Ser Ile His Pro Asn Phe Pro Glu Lys His Asp Gln Ala Asn Tyr
305                 310                 315                 320
Pro Ile Ile Gly Lys Gly Pro Val Leu Lys Val Asn Ala Asn Gln Arg
                325                 330                 335
Tyr Thr Ser Asp Ala Val Thr Ser Gly Met Trp Ile Arg Ala Cys Gln
                340                 345                 350
Ile Ala Gly Val Pro His Gln Val Phe Ala Gly Asn Asn Asp Val Pro
                355                 360                 365
Cys Gly Ser Thr Ile Gly Pro Ile Ser Ala Thr Arg Leu Gly Ile Asp
370                 375                 380
Ser Val Asp Val Gly Ile Pro Leu Leu Ser Met His Ser Ala Arg Glu
385                 390                 395                 400
Met Ala Gly Val Lys Asp Leu Met Trp Phe Glu Gln Ala Leu Glu Ala
                405                 410                 415
Tyr Leu Val Asn
            420

<210> SEQ ID NO 17
<211> LENGTH: 22
<212> TYPE: DNA
<213> ORGANISM: Artificial Sequence
<220> FEATURE:
<223> OTHER INFORMATION: Synthetic DNA

<400> SEQUENCE: 17
cgcattccga cgttggctat cc                                          22

<210> SEQ ID NO 18
<211> LENGTH: 23
<212> TYPE: DNA
<213> ORGANISM: Artificial Sequence
<220> FEATURE:
<223> OTHER INFORMATION: Synthetic DNA

<400> SEQUENCE: 18
atgttggaag agctcttgaa gag                                         23

<210> SEQ ID NO 19
<211> LENGTH: 19
```

```
<212> TYPE: DNA
<213> ORGANISM: Artificial Sequence
<220> FEATURE:
<223> OTHER INFORMATION: Synthetic DNA

<400> SEQUENCE: 19
tagggaacag ttgagtctc                                                  19

<210> SEQ ID NO 20
<211> LENGTH: 21
<212> TYPE: DNA
<213> ORGANISM: Artificial Sequence
<220> FEATURE:
<223> OTHER INFORMATION: Synthetic DNA

<400> SEQUENCE: 20
tccgtgtgag ccccgatcat g                                               21

<210> SEQ ID NO 21
<211> LENGTH: 22
<212> TYPE: DNA
<213> ORGANISM: Artificial Sequence
<220> FEATURE:
<223> OTHER INFORMATION: Synthetic DNA

<400> SEQUENCE: 21
tcccgctaca actctttgtc gt                                              22

<210> SEQ ID NO 22
<211> LENGTH: 21
<212> TYPE: DNA
<213> ORGANISM: Artificial Sequence
<220> FEATURE:
<223> OTHER INFORMATION: Synthetic DNA

<400> SEQUENCE: 22
atgacgtcta atctaacgaa g                                               21

<210> SEQ ID NO 23
<211> LENGTH: 22
<212> TYPE: DNA
<213> ORGANISM: Artificial Sequence
<220> FEATURE:
<223> OTHER INFORMATION: Synthetic DNA

<400> SEQUENCE: 23
gattcactag ccctcgcact ac                                              22

<210> SEQ ID NO 24
<211> LENGTH: 24
<212> TYPE: DNA
<213> ORGANISM: Artificial Sequence
<220> FEATURE:
<223> OTHER INFORMATION: Synthetic DNA

<400> SEQUENCE: 24
tccaccttga tcgccaggag actt                                            24

<210> SEQ ID NO 25
<211> LENGTH: 19
<212> TYPE: DNA
<213> ORGANISM: Artificial Sequence
<220> FEATURE:
<223> OTHER INFORMATION: Synthetic DNA

<400> SEQUENCE: 25
```

-continued tagggaacaa ttgggtctc                                          19

<210> SEQ ID NO 26
<211> LENGTH: 18
<212> TYPE: DNA
<213> ORGANISM: Artificial Sequence
<220> FEATURE:
<223> OTHER INFORMATION: Synthetic DNA

<400> SEQUENCE: 26
ggcttccatt tcttgccg                                           18

<210> SEQ ID NO 27
<211> LENGTH: 30
<212> TYPE: DNA
<213> ORGANISM: Artificial Sequence
<220> FEATURE:
<223> OTHER INFORMATION: Synthetic DNA

<400> SEQUENCE: 27
atgacttcga aaatcgccca aaatttgaag                              30

<210> SEQ ID NO 28
<211> LENGTH: 28
<212> TYPE: DNA
<213> ORGANISM: Artificial Sequence
<220> FEATURE:
<223> OTHER INFORMATION: Synthetic DNA

<400> SEQUENCE: 28
tcagtcaaca aagattgtct ttgacgtg                                28

<210> SEQ ID NO 29
<211> LENGTH: 17
<212> TYPE: DNA
<213> ORGANISM: Artificial Sequence
<220> FEATURE:
<223> OTHER INFORMATION: Synthetic DNA

<400> SEQUENCE: 29
ttgtcctttg tcaatgc                                            17

<210> SEQ ID NO 30
<211> LENGTH: 18
<212> TYPE: DNA
<213> ORGANISM: Artificial Sequence
<220> FEATURE:
<223> OTHER INFORMATION: Synthetic DNA

<400> SEQUENCE: 30
cggatactgt gcatgctt                                           18

<210> SEQ ID NO 31
<211> LENGTH: 19
<212> TYPE: DNA
<213> ORGANISM: Artificial Sequence
<220> FEATURE:
<223> OTHER INFORMATION: Synthetic DNA

<400> SEQUENCE: 31
caacaagggc cctgttatc                                          19

<210> SEQ ID NO 32
<211> LENGTH: 18
<212> TYPE: DNA
<213> ORGANISM: Artificial Sequence

```
<220> FEATURE:
<223> OTHER INFORMATION: Synthetic DNA

<400> SEQUENCE: 32
ctttgccgac tgaacggc                                                    18

<210> SEQ ID NO 33
<211> LENGTH: 34
<212> TYPE: DNA
<213> ORGANISM: Artificial Sequence
<220> FEATURE:
<223> OTHER INFORMATION: Synthetic DNA

<400> SEQUENCE: 33
gtaaggaggt ttaaaatgac ttcgaaaatc gccc                                  34

<210> SEQ ID NO 34
<211> LENGTH: 34
<212> TYPE: DNA
<213> ORGANISM: Artificial Sequence
<220> FEATURE:
<223> OTHER INFORMATION: Synthetic DNA

<400> SEQUENCE: 34
ctaatcaaca aagatggtct tggaaagatt ggcg                                  34

<210> SEQ ID NO 35
<211> LENGTH: 24
<212> TYPE: DNA
<213> ORGANISM: Artificial Sequence
<220> FEATURE:
<223> OTHER INFORMATION: Synthetic DNA

<400> SEQUENCE: 35
ctatgttcag gatacaactg agaa                                             24

<210> SEQ ID NO 36
<211> LENGTH: 24
<212> TYPE: DNA
<213> ORGANISM: Artificial Sequence
<220> FEATURE:
<223> OTHER INFORMATION: Synthetic DNA

<400> SEQUENCE: 36
cagtttagac aacaatttca gatt                                             24

<210> SEQ ID NO 37
<211> LENGTH: 52
<212> TYPE: DNA
<213> ORGANISM: Artificial Sequence
<220> FEATURE:
<223> OTHER INFORMATION: Synthetic DNA

<400> SEQUENCE: 37
gtaaggaggt ttaaaatgca tgtaactgac gatttcttaa gttttattgc cc              52

<210> SEQ ID NO 38
<211> LENGTH: 29
<212> TYPE: DNA
<213> ORGANISM: Artificial Sequence
<220> FEATURE:
<223> OTHER INFORMATION: Synthetic DNA

<400> SEQUENCE: 38
ttaatttacc agataggctt ccagggctt                                        29
```

```
<210> SEQ ID NO 39
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 39

Glu His Phe Arg Trp Gly
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 40

Glu Gly Val Tyr Val His Pro Val
1               5
```

METHOD OF IMPROVING TASTE AND/OR FLAVOUR OF FOODS AND BEVERAGES

FIELD OF THE INVENTION

The present invention relates to a method of improving taste and/or flavour of foods and beverages such as seasoning and flavouring materials.

BACKGROUND OF THE INVENTION

There have been many reports on methods of improving taste and/or flavour using enzymes. For example, as a method for enhancing umami a process of increasing free amino acids by the use of a combination of proteases and peptidases has been known. Such a process may be used for not only producing seasoning mix but also improving the quality and taste of meat (Japanese publication of non-examined patent application (JP-Kokai) No. 05-276899). There is also a method which uses an enzyme that specifically functions on proline as described in JP Kokai No. 11-075765 or No. 07-115969. A method of enhancing umami is also known where glutamate is increased by using a γ-GTP (gamma glutamyl transpeptidase) during protease reaction or by converting glutamine to glutamate by a glutaminase. The peptidases of the present invention were also reported to have an umami-enhancing activity because they specifically release glutamate or aspartate (JP Kokai No. 2000-325090).

For example koji molds have been used to produce natural seasonings including soy sauce, miso and other protein hydrolysates. For example soy sauce is produce through two steps, koji-making and fermentation. The raw materials are mainly hydrolized by enzymes produced by koji molds (*Aspergillus* fungi) during the koji-making step. During the step, it is important to increase the content of free amino acids in the resulting koji (moromi), particularly the content of free glutamate to improve the taste of soy sauce.

In general, amino acids are generated through two steps from raw material proteins. The first step is the release of peptides from the proteins by proteases, and the second step is the generation of amino acids by hydrolysis of the peptides, which is catalyzed by peptidases.

Asano et al. noticed that soybeans hydrolyze the storage proteins in the seeds in a very short period during the germinating process and found a peptidase (a peptidase which efficiently hydrolyzes peptides containing acidic amino acid residues and leucine aminopeptidases) and succeeded in the efficient hydrolysis of soybean proteins (JP Kokai No. 9-294583).

The soybean aminopeptidase is an enzyme which has been proved to be a novel enzyme, which has not been reported previously, as defined by its enzymatic profile. The existence of the enzyme has not been known except in germinating soybeans. The soybean aminopeptidase has the activity of releasing N-terminal acidic amino acids efficiently from peptides having acidic amino acids such as glutamic acid at the N-terminal. It is known that a di-peptide consisting of two glutamic acid residues exists as a hydrolysis-resistant peptide in seasonings including protein hydrolysates, such as soy sauce. Accordingly, it is possible to hydrolyze such hydrolysis-resistant di-peptides by using the action of the soybean aminopeptidase to produce a seasoning liquid which has a high content of free glutamate and improved taste.

Ninomiya et al. succeeded in the mass production of the soybean aminopeptidase by using genetic recombination techniques (JP Kokai No. 2000-325090), but the soybean aminopeptidase GX produced by this method can be hardly used for producing seasoning liquid, because peptidases from soybean are not approved as enzymes for foods. Additionally, there remain several problems in their applicability because the recombinant soybean is poor in the heat-stability and is not suitable for the reaction at 50° C. or more.

For peptidases from koji molds which include many microorganism species for foods, peptidases from *Aspergillus oryzae* and *Aspergillus sojae* have been reported (JP Kokai No. 11-346777, DE95-1952648, WO 98/51163, WO 96/28542, WO 96/15504, WO 98/51803, WO 98/14599). Among them, there are many reports on leucine aminopeptidases, but there is no report on a peptidase that has an activity to efficiently release glutamate, such as the soybean aminopeptidase GX. For example, Koibuchi et al. screened a *Aspergillus nidulans* genomic DNA library using *Aspergillus nidulans* ESTs having a homology to the soybean aminopeptidase GX and obtained a DNA encoding a novel aminopeptidase of *Aspergillus nidulans* (WO 02/077223). However, the obtained novel aminopeptidase was the enzyme having leucine aminopeptidase (LAP) activity, which requires cobalt or zinc ion for its activation, although it had a homology of close to 40% to the soybean GX. Thus, an enzyme having the soybean aminopeptidase-like properties has not been obtained from other sources than soybean. Furthermore, it was shown that the existence of the soybean aminopeptidase-like properties could not be determined from the sequence homology alone.

In this connection, an EST database of a koji mold (*Aspergillus oryzae* RIB40) was opened on Mar. 31, 2003 at the Web site of National Research Institute of Brewing and the search for the sequences has been possible.

On the other hand, methods for improving sweetness and flavour are known where hydrolyzing enzymes or microorganisms containing the enzymes are used, or a combination of the enzymes and other processes are used for improving sweetness. For example, in JP Kokai No. 09-299094 after reacting the enzymes or the microorganisms on carbohydrates, alcohol fermentation was conducted to improve the flavour. In JP Kokai No. 09-299094, the improvement in sweetness was also succeeded by functions of sugar hydrolyzing enzymes together with sugar transfer reactions and condensation reactions. Particularly, in JP Kokai No. 2003-153651 sweetness and umami were increased by reacting enzymes which decompose tannin, polysaccharides and proteins on tea leafages material or dried tea leafages to reduce astringency. However, a method for enhancing sweetness by the action of peptidases alone has not been reported.

As methods for reducing saltiness edge, treatment with various essences (JP Kokai No. 2002-034496) or yeast (JP Kokai No. 11-276113) or the addition of soybean mineral concentrates (JP Kokai No. 05-049439) have been reported. However no successful examples have been known where saltiness edge taste was reduced by a peptidase treatment.

The following processes have been reported as general methods for improving flavour and taste by enzymes. For improving the taste of egg yolk, phospholipases has been used and JP Kokai No. 2002-325559 clearly describes the effects of phospholipase A1. In JP Kokai No. 2002-253171, bitter amino acids were γ-glutamylated by a γ-glutamyl transpeptidase and the reduction of bitterness, the increase of sourness and the improvement of taste were successful. Additionally, in JP Kokai No. 2000-327692 the taste and the solubility of isoflavones were improved by the function of glycosyltransferases. Besides these reports, many methods are known including a method for producing taste-improving food materials by glutamate decarboxylases (JP Kokai No. 2000-166502), a method for providing flavour improving composition by synthesizing adenine using glutaminases (JP Kokai No. 09-313129), a method for improving flavour of foods using beta-primevelosidases (JP Kokai No. 08-140675), a method for improving the flavour of oils and fats using lipases (JP Kokai No. 07-135972) and a method for improving the taste of bread by a combination of lactic acid bacteria, lipases and proteases. However, a method for improving taste and/or flavour by peptidases alone has not been known.

SUMMARY OF THE INVENTION

An object of the present invention is to provide a method for producing foods and beverages which have a high content of glutamate or aspartate and which are improved in the taste and/or flavour.

The inventors of the present invention obtained a DNA encoding a novel aminopeptidase from *Aspergillus nidulans*, which have the soybean aminopeptidase-like activity, by using 5' RACE method based on *Aspergillus nidulans* (*A. nidulans*) ESTs having homology to the soybean aminopeptidase GX gene. Additionally, the inventors obtained DNAs encoding novel aminopeptidases from *Aspergillus oryzae*, *Aspergillus niger*, a yeast and of a coryneform bacterium, which have the soybean aminopeptidase-like activity based on the obtained sequence information. Furthermore, the inventors found that foods and beverages having enhanced taste and/or flavour can be produced by treating these aminopeptidases on protein materials optionally under the co-existence of proteases, whereby increasing the free glutamate content.

Accordingly, the present inventions are described as follows.

(1) A method for producing foods and/or beverage having improved taste and/or flavour, comprising reacting an aminopeptidase from a microorganism on a protein material optionally under the co-existence of a protease, wherein said aminopeptidase has the following properties:

(a) having an activity of catalyzing the reaction of specifically releasing a glutamic acid and an aspartic acid from the N-terminal of a peptide and/or a protein;

(b) having 50% or more activity at pH6.0-9.0 compared with the activity at the optimum pH;

(c) having 40% or more activity after heating at 25-60° C., pH7.5 for 30 minutes as compared with the activity of the non-heated enzyme;

(d) having a molecular weight of about 40-60 kD as measured by SDS-PAGE and about 300-480 kD as measured by native-PAGE;

(e) having a hydrolyzing activity of 5 U/mg or more for Glu-Glu dipeptide, preferably 10 U/mg or more.

(2) the method according to item (1), wherein the aminopeptidase is encoded by the nucleic acid molecule having the nucleotide sequence shown in SEQ ID NO:2 or is encoded by the nucleic acid molecule which is hybridizable to the nucleic acid molecule having the nucleotide sequence shown in SEQ ID NO:2;

(3) the method according to item (1), wherein the aminopeptidase is encoded by the nucleic acid molecule having the nucleotide sequence shown in SEQ ID NO:6 or is encoded by the nucleic acid molecule which is hybridizable to the nucleic acid molecule having the nucleotide sequence shown in SEQ ID NO:6;

(4) the method according to item (1), wherein the aminopeptidase is encoded by the nucleic acid molecule having the nucleotide sequence shown in SEQ ID NO:9 or is encoded by the nucleic acid molecule which is hybridizable to the nucleic acid molecule having the nucleotide sequence shown in SEQ ID NO:9;

(5) the method according to item (1), wherein the aminopeptidase is encoded by the nucleic acid molecule having the nucleotide sequence shown in SEQ ID NO:12 or is encoded by the nucleic acid molecule which is hybridizable to the nucleic acid molecule having the nucleotide sequence shown in SEQ ID NO:12;

(6) a method for producing foods and/or beverage having improved taste and/or flavour, comprising treating an aminopeptidase from a microorganism on a protein material optionally under the co-existence of a protease, wherein said aminopeptidase is encoded by the nucleic acid molecule having the nucleotide sequence shown in SEQ ID NO:15 or is encoded by the nucleic acid molecule which is hybridizable to the nucleic acid molecule having the nucleotide sequence shown in SEQ ID NO:15.

(7) the method according to any of items (1) to (6), wherein the aminopeptidase is produced by a transformed microorganism;

(8) the method according to any of items (1) to (7), wherein the foods and/or beverages are selected from the group consisting of protein hydrolysates, cheeses, tomato juice containing beverages and soy milk-containing beverages.

*Aspergillus oryzae* EAP; (5B) *Aspergillus nidulans* EAP (5C) *Aspergillus niger* EAP; (5D) Coryneform bacterial EAP; (5E) Yeast EAP.

Figure 6A:
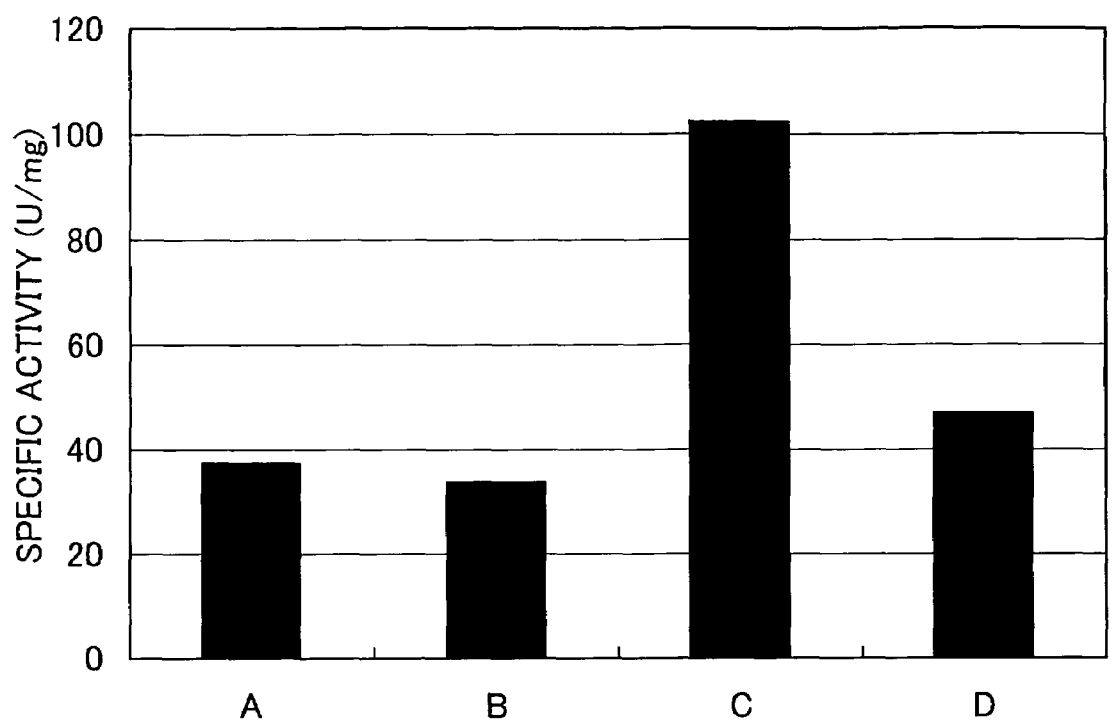
Figure 6B:
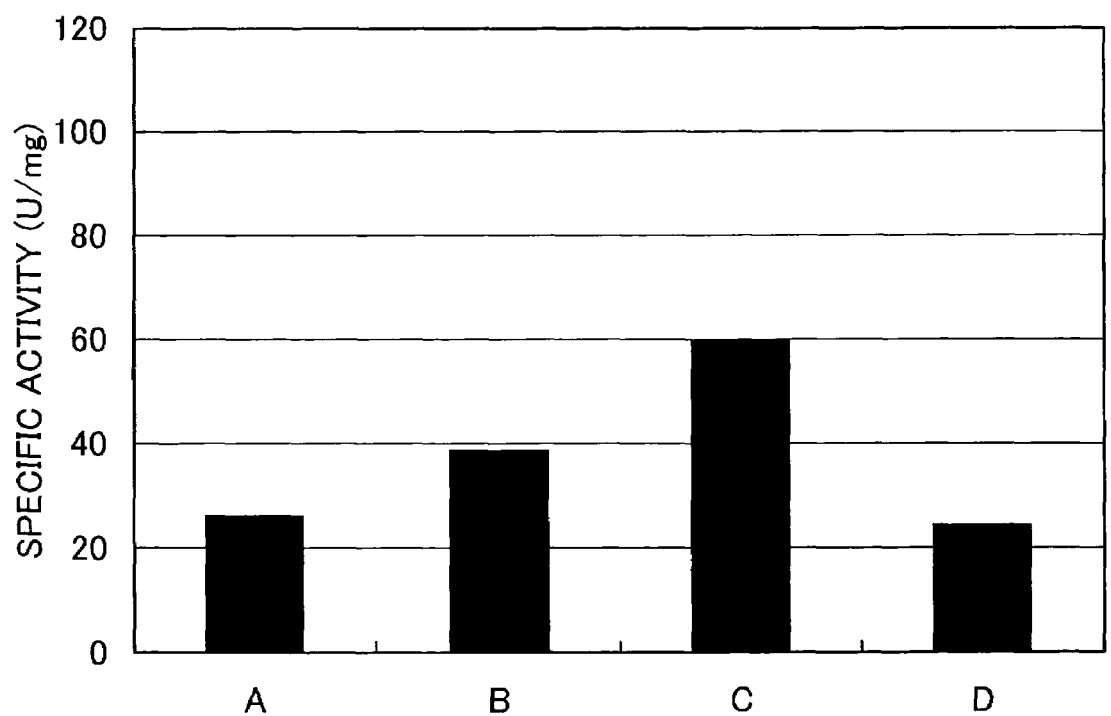

FIG. 6 is a graph showing the reaction profiles of the EAPs on peptides having different lengths. The symbols "A", "B", "C" and "D" indicated in the horizontal axes represent the substrates: (A) Glu-Glu; (B) Glu-His-Phe-Arg-Trp-Gly; (C) Glu-Gly-Val-Tyr-Val-His-Pro-Val; (D) Asp-Glu. (6A) *Aspergillus oryzae* EAP; (6B) *Aspergillus niger* EAP; (6C) Coryneform bacterial EAP; (6D) Yeast EAP.

Figure 7:
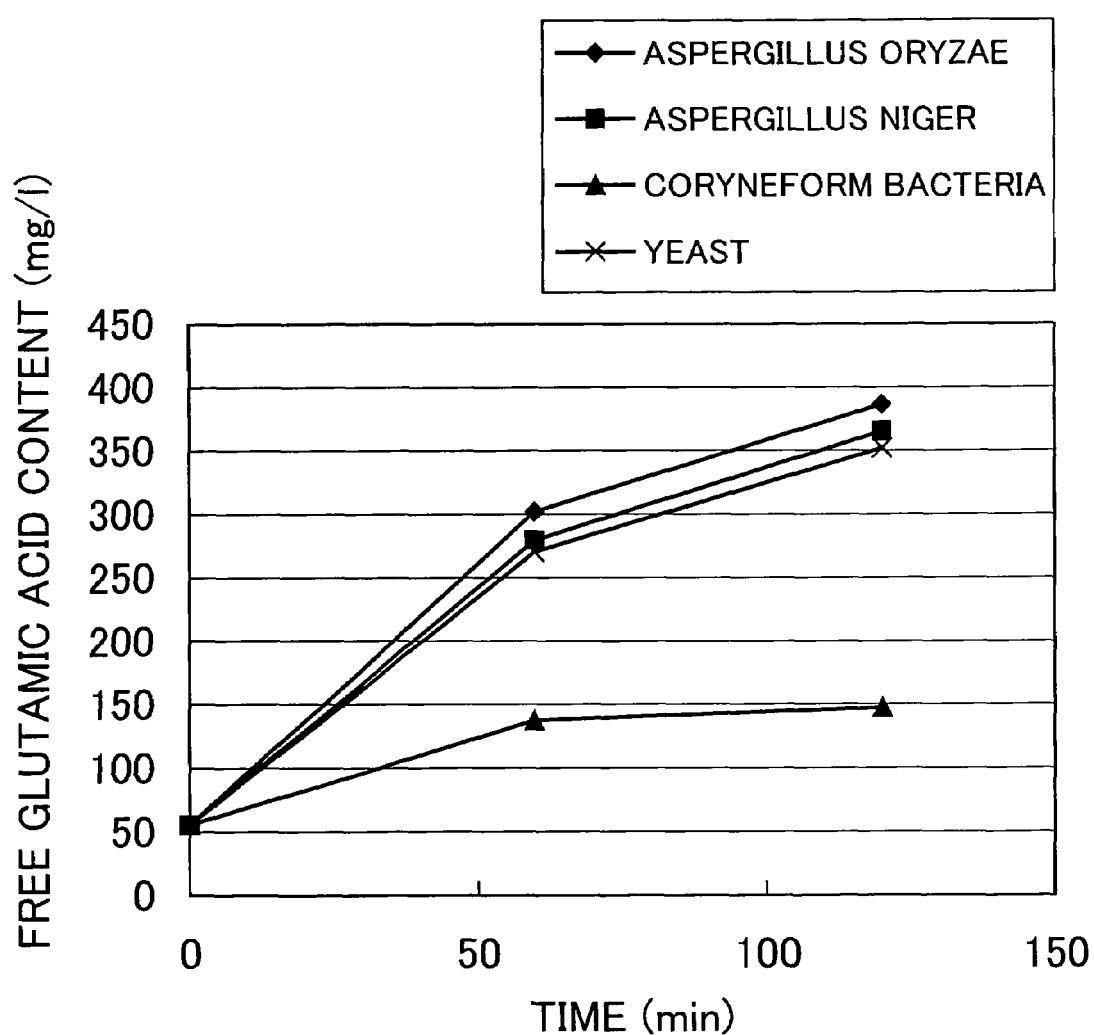

FIG. 7 is a graph showing the taste-enhancing effects of the EAPs on a bonito-essence seasoning.

Figure 8A:
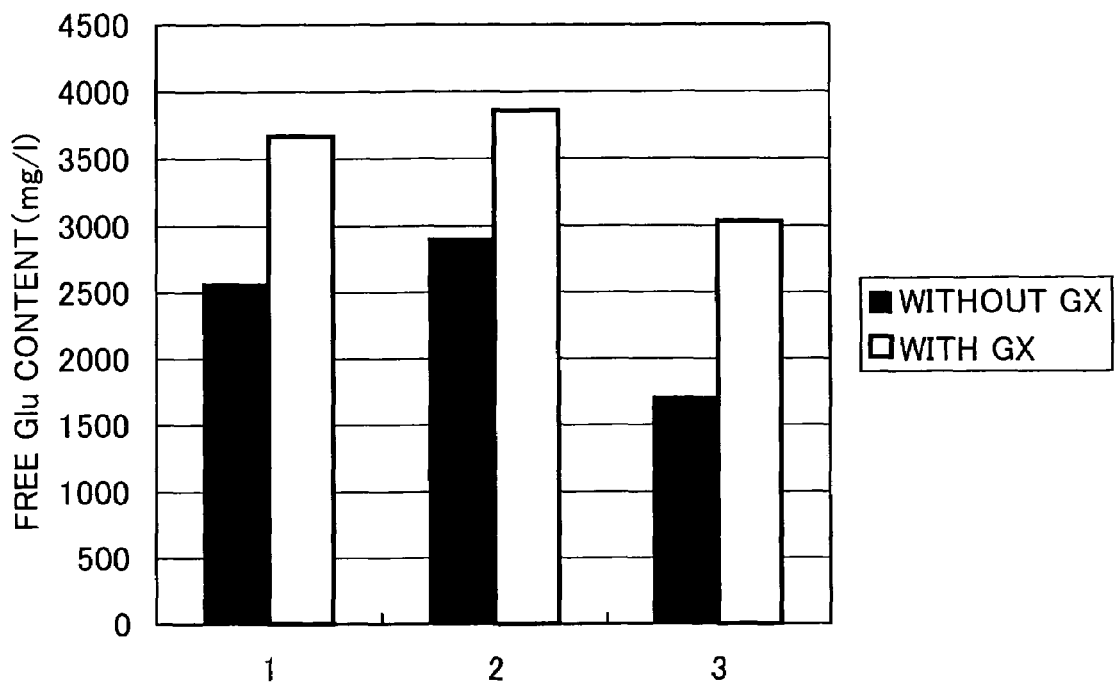
Figure 8B:
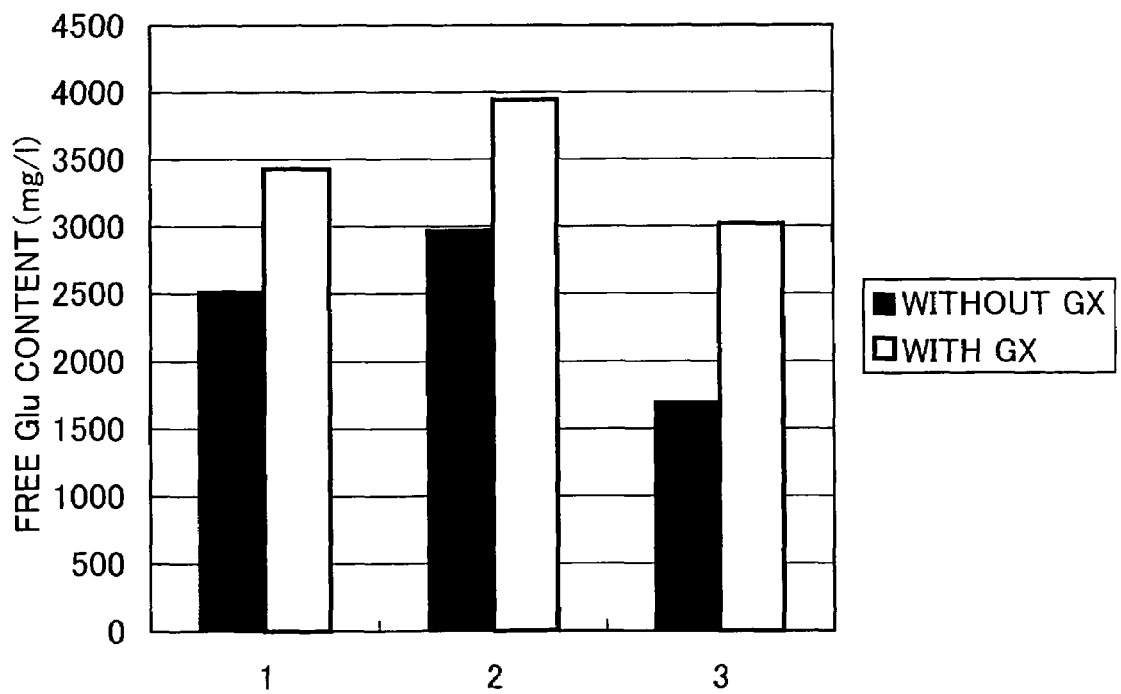

FIG. 8 is graph showing the effects of the addition of the EAPs on a protein hydrolysate solution from isolated soybean proteins which has been hydrolyzed by PROTEASE M™ (a commercially available protease preparation) and UMAMIZYME™ (a peptidase preparation). The vertical axes indicate the contents of free Glu contained in the hydrolysate solutions. (8A) *Aspergillus oryzae* EAP; (8B) *Aspergillus nidulans* EAP. 1. UMAMIZYME™ 1% +PROTEASE M™ 1%; 2. UMAMIZYME™ 2%; 3. PROTEASE M™ 2%.

Figure 9A:
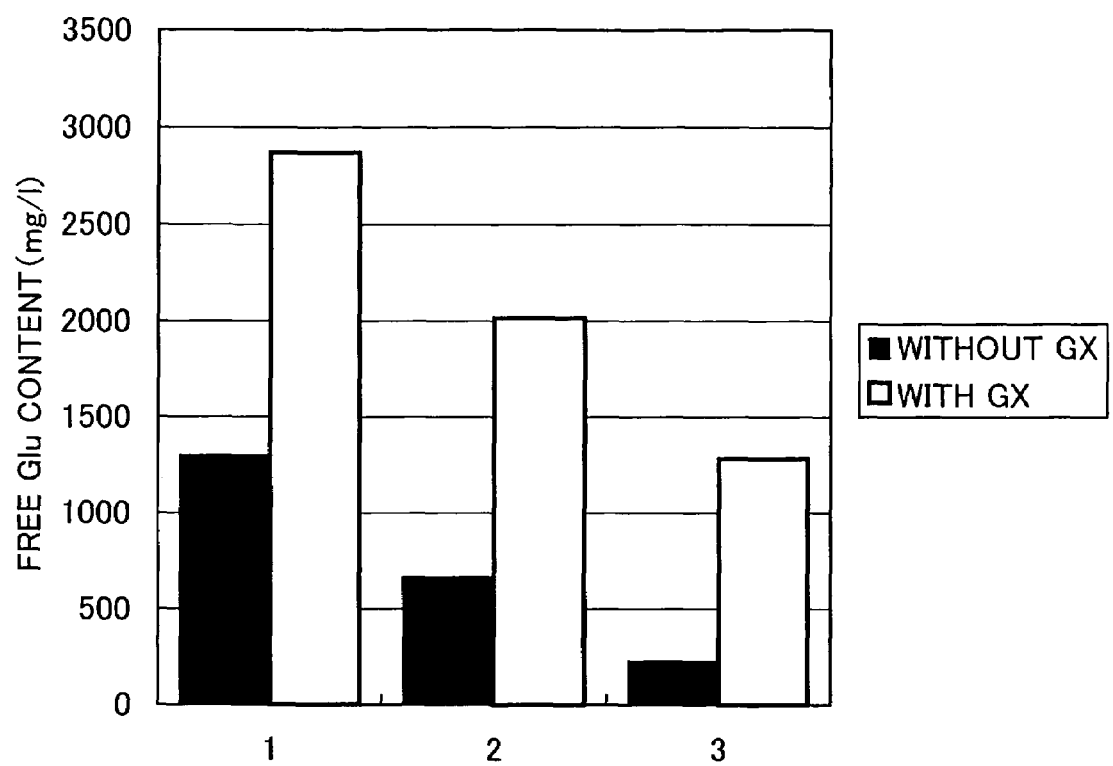
Figure 9B:
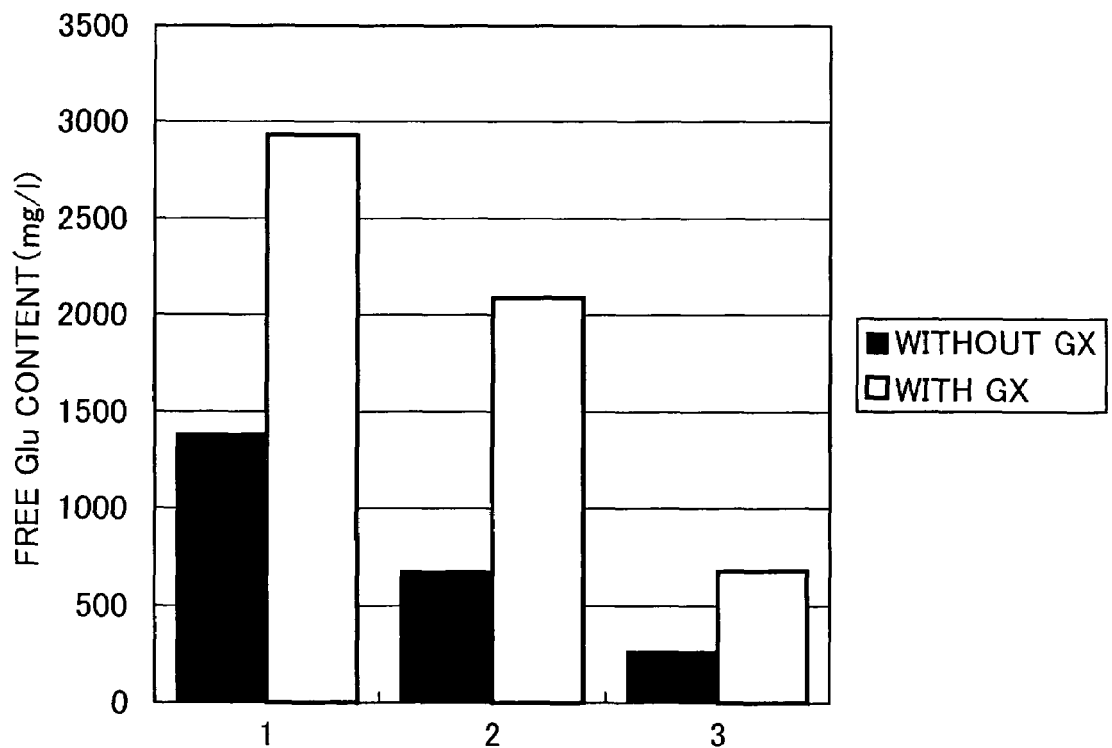

FIG. 9 is a graph showing the effects of the addition of the EAPs on a protein hydrolysate solution from isolated soybean proteins which has been hydrolyzed by (a commercially available protease preparation) and (a peptidase preparation). The vertical axes indicate the contents of free Glu contained in the hydrolysate solutions. (9A) *Aspergillus oryzae* EAP; (9B) *Aspergillus nidulans* EAP. 1. ALCALASE™ 1 % +FLAVOURZYME™ 1%; 1. ALCALASE™ 1% +FLAVOURZYME™1%; 3. ALCALASE™ 1%.

DESCRIPTION OF THE PREFERRED EMBODIMENTS

The present invention is a method for producing foods and/or beverages having improved taste and/or flavour by reacting an microbial aminopeptidase having the aforementioned properties on a protein material, optionally under the existence of a protease. Particularly, the aminopeptidases used in the present invention are glutamic acid- and/or aspartic acid-specific microbial aminopeptidases.

The aminopeptidases used in the present invention are considered to be koji-molds counterpart of the aforementioned soybean aminopeptidase GX. As used in the specification, therefore, the glutamic acid- and/or aspartic acid-specific aminopeptidase protein used in the present invention may be referred to as "EAP" or "aminopeptidase EAP" and the gene encoding the EAP may be referred to as "EAP gene". When it is apparent from the context, the glutamic acid- and/or aspartic acid-specific aminopeptidase protein used in the present invention may be simply referred to as "aminopeptidase". For example, the glutamic acid- and/or aspartic acid-specific aminopeptidase from *Aspergillus oryzae* and the glutamate- and/or aspartate-specific aminopeptidase from *Aspergillus nidulans*, which are used in the present invention, may be referred to as "*Aspergillus oryzae* EAP" and "*Aspergillus nidulans* EAP", respectively. On the other hand, the aforementioned soybean aminopeptidase (JP Kokai No. 2000-325090) may be referred to as "GX" or "soybean aminopeptidase GX" or "soybean GX".

As used herein, "aminopeptidase" particularly means a protein which has an activity of releasing acidic amino acids such as glutamic acid or aspartic acid from the N-terminal of a peptide.

A nucleic acid molecule encoding the aminopeptidase EAP used in the present invention maybe obtained form a chromosomal DNA or a cDNA of *Aspergillus* including *Aspergillus oryzae* and *Aspergillus nidulans* and the like, for example *Aspergillus nidulans* A26, as described below.

PCR (polymerase chain reaction) primers may be generated based on the nucleotide sequence of ESTs in the *Aspergillus nidulans* database having a high homology to the gene sequence of the aminopeptidase from germinating soybean (JP Kokai No. 2000-325090), and a clone containing a nucleic acid molecule encoding the aminopeptidase EAP usable for the present invention may be obtained by PCR using the *Aspergillus nidulans* cDNA or the *Aspergillus nidulans* chromosomal DNA as a template.

The nucleic acid molecule may be obtained from a cDNA library prepared from *Aspergillus nidulans* polyA RNAs, for example by PCR using the oligonucleotides having the nucleotide sequences of SEQ ID NOs:17 and 18 as primers, followed by 5'-RACE using the oligonucleotides shown in SEQ ID NOs:19 and 20 as primers. The examples of the primers to obtain the sequence containing the entire open reading frame (ORF) are the oligonucleotides having the nucleotide sequences shown in SEQ ID NOs: 22 and 23. The nucleotide sequence of the genomic DNA containing the gene encoding the *Aspergillus nidulans* A26 derived aminopeptidase, which can be obtained according to the above-described methods, is shown in SEQ ID NO:1. The nucleotide sequence of the cDNA is shown in SEQ ID NO:2 and the amino acid sequence is shown in SEQ ID NO:3. Comparison of the genomic DNA and the cDNA nucleotide sequence revealed no introns in the genomic DNA.

A nucleic acid molecule encoding the aminopeptidase used for the present invention can be obtained from chromosomal DNAs or cDNAs of microorganisms belonging to other species of genus *Aspergillus*, for example *Aspergillus oryzae*. Particularly, the nucleic acid molecule may be obtained from *Aspergillus oryzae*, for example *Aspergillus oryzae* RIB40 (ATCC42149) cDNA by PCR method. The oligonucleotide primers for PCR may be synthesized based on the nucleotide sequence of the *Aspergillus nidulans* derived aminopeptidase and PCR may be conducted using the cDNA prepared from *Aspergillus oryzae* cells as a template, for example from *Aspergillus oryzae* RIB40 cells. The PCR primers for this purpose include dT primer and the oligonucleotide having the sequence shown in SEQ ID NO:24, the 5'-RACE primers include the oligonucleotides having the sequences shown in SEQ ID NOs:25 and 26 and the primers for obtaining the entire ORF include the oligonucleotides having the sequences shown in SEQ ID NOs:27 and 28.

The nucleotide sequence of thus obtained cDNA encoding the EAP of *Aspergillus oryzae* RIB40 is shown in SEQ ID NO:6 and the amino acid sequence is shown in SEQ ID NO:7. The amino acid sequence of the *Aspergillus nidulans* EAP shown in SEQ ID NO:3 and the amino acid sequence of the aminopeptidase from *Aspergillus oryzae* shared a homology of 83% and they differs in about 85 amino acid residues. The homology between the *Aspergillus oryzae* EAP gene and the *Aspergillus nidulans* EAP gene is about 76% in the coding regions and is 80% or more in the amino acid sequences, as measured by the analyzing software GENETYX-MAC Ver. 10. Comparison between the genomic DNA and the cDNA revealed that the genomic DNA of *Aspergillus oryzae* contained five (5) introns. The genomic nucleotide sequence encoding the *Aspergillus oryzae* EAP is shown in SEQ ID NO:4.

Nucleic acid molecules encoding the EAPs of *Aspergillus niger*, coryneform bacteria and yeast may be obtained respectively according to the similar methods. The genomic sequences of the EAP genes from *Aspergillus niger*, yeast and coryneform bacterium are shown in SEQ ID NOs:8, 11 and 14, respectively, and the nucleotide sequences of the coding regions are shown in SEQ ID NOs:9, 12 and 15, respectively. The amino acid sequences of the EAPs are shown in SEQ ID NOs:10, 13 and 16, respectively.

The ORF contained in the cDNA sequence shown in SEQ ID NO:6, that is, the nucleotide sequence encoding the aminopeptidase used for the present invention, is disclosed in the *Aspergillus oryzae* EST database for the entire sequence. Furthermore, in the aforementioned database the proposed function of the protein encoded by the ORF is described as an "aspartyl aminopeptidase". However, it has been demonstrated that the enzymes actually obtained by the inventors of the present invention had a significantly different functions from an aspartyl aminopeptidase. For example, an aspartyl aminopeptidase has a weaker activity in releasing glutamic acid than the activity for releasing aspartic acid (Cheung, H. S. and Cushman, D. W. B.B.A. 242, 190-193 (1971)). On the other hand, one of the features of the present invention resides in that the releasing activity of the aminopeptidase used in the present invention for glutamic acid is almost equal to the releasing activity for aspartic acid. Additionally, it is understood that an aspartyl aminopeptidase has little activity of hydrolyzing short substrates such as di-peptides (S. Wilk, E. Wilk, R. P. Magnusson, Arch. Biochem. Biophys. 407 (2002) 176-183), while another feature of the present invention is that the aminopeptidases used for the present invention efficiently hydrolyze short peptides such as hydrolysis-resistant di-peptides which may be frequently found, for example in a soy sauce brewing process.

Accordingly, the present invention utilizes the functions and properties that are different from those of the hypothetical protein of which functions and properties have been presumed in the *Aspergillus oryzae* EST database.

The aminopeptidase used for the present invention may be an aminopeptidase having one or plural amino acid(s) replacement, deletion, insertion or addition at one or more position(s) in the amino acid sequence shown in SEQ ID NO:7, as long as the above-described aminopeptidase activity is not impaired. As used herein, "plural" normally means 2-85, preferably 2-50, most preferably 2-10, although it varies depending on the locations and species of the amino acid residues. Although the replacement of 85 amino acids can be found between the *Aspergillus oryzae* derived aminopeptidase and the *Aspergillus nidulans* derived aminopeptidase, both retain the equivalent activities as shown in Examples. Therefore, it is expected that the functions and properties of the aminopeptidase can be retained to the extent sufficient to be used for the present invention by the amino acid replacement within this range.

The genes encoding the aminopeptidase used for the present invention include the DNA having the nucleotide sequence consisting of base no. 1 to no. 1494 of the nucleotide sequence shown in SEQ ID NO:6. Additionally, it may include a modification caused by the degeneracy in the genetic codes. Furthermore, a nucleic acid molecule encoding a protein having the equivalent properties to those of the EAP may be obtained by modifying the nucleotide sequence of EAP such that the amino acids at particular locations are replaced, deleted, inserted or added by, for example site-specific mutagenesis. Such modified nucleic acid molecules may also be obtained by a conventionally known mutagenesis process. The examples of such mutagenesis processes include a process where the DNA encoding the aminopeptidase is treated in vitro with hydroxylamine and the like, a process of treating *Escherichia* bacteria harboring the DNA encoding the aminopeptidase with UV irradiation or a mutagen which is conventionally used for mutagenesis such as N-methyl-N'-nitro-N-nitrosoguanidine (NTG).

The replacement, deletion, insertion, addition and the like include the naturally occurring mutations such as the variation among the species or strains of koji mold. The nucleic acid molecules having the above-mentioned modification may be expressed in suitable cells and the expressed products may be tested for the EAP activity to obtain a nucleic acid molecule encoding a protein which is substantially identical to the EAP. Alternately, a nucleic acid molecule encoding a protein which is substantially identical to the EAP may also be obtained by, for example, isolating a nucleic acid molecule which hybridizes under stringent conditions with a nucleic acid molecule having the sequence of nos. 1-1494 of the nucleotide sequence shown in SEQ ID NO:6, and which encodes a protein having the EAP activity from nucleic acid molecules encoding the modified EAP or cells harboring the nucleic acid molecules. As used herein, "stringent condition" is a condition where a so-called specific hybrid is formed. It is difficult to describe this condition numerically and specifically because the condition depends on a particular sequence, the GC-content and the existence or absence of repeating sequences. The examples of the conditions include the conditions where nucleic acid molecules having 65% or more homology can hybridize one another but nucleic acid molecules having less homology do not hybridize one another, or alternately the conditions where hybridization is conducted at 60° C. and in 1×SSC, 0.1% SDS, preferably 0.1×SSC, 0.1% SDS or corresponding salt concentration. The genes hybridizable under these conditions may include those which have a stop codon in the middle or lost the activity due to the alteration in the active center, but they can be easily removed by connecting them to commercially available expression vectors and determining the EAP activity according to the method described below.

The homology among the EAPs from *Aspergillus nidulans*, *Aspergillus oryzae* and *Aspergillus niger* is 80% or more for the amino acid sequences between any two of these aminopeptidases EAPs, as determined by a sequence analyzing software GENETYX-MAC Ver. 10.

The nucleic acid molecule encoding the aminopeptidase used for the present invention may be used for producing the aminopeptidase used for the present invention.

The nucleic acid molecules encoding the aminopeptidases (EAPs) used for the present invention may be used for the breeding of filamentous fungi such as koji mold or for the production of the EAP. For example, the EAP activity may be increased by introducing the DNA encoding the aminopeptidase of the present invention into the cells of a filamentous fungus (such as *Aspergillus oryzae*), preferably as multi-copy DNA. The EAP can be produced by expressing the nucleic acid molecules of the present invention in a suitable host.

The filamentous fungi into which the nucleic acid molecules encoding the aminopeptidases for the present invention are introduced include the filamentous fungi belonging to the genus *Aspergillus* such as *Aspergillus oryzae*, *Aspergillus niger* and *Aspergillus nidulans*; those belonging to the genus *Neurospora* such as *Neurospora crassa*, and those belonging to the genus *Rhizomucor* such as *Rhizomucor miehei*. The filamentous fungi of the genus *Aspergillus* are particularly preferred.

The vectors for introducing the nucleic acid molecules into the above-described filamentous fungi are not particularly limited and the vectors usually used for filamentous fungi for breeding and the like may be used. For example, the vectors used for *Aspergillus oryzae* include pUNG (Lee, B. R. et al., Appl. Microbiol. biotechnol., 44, 425-431 (1995)), PMARG (Tsuchiya, K. et al., Appl. Microbiol. Biotechnol., 40, 327-332 (1993)), pUSC (Gomi, K. et al., Agric. Biol. Chem. 51, 2549-2555 (1987)), etc. pUNG has a marker complementing niaD$^-$ (defection in nitric acid assimilability) of *Aspergillus oryzae* niaD300 (Minetoki, T. et al., Curr. Genet. 30, 432-438 (1996)); pMARG has a marker complementing argB$^-$ (arginine requirement) of *Aspergillus oryzae* M2-3 (Gomi, K. et al., Agric. Biol. Chem., 51(9), 2549-2555 (1987)); and pUSC has a marker complementing sC$^-$ (defection in ATP sulfurylase) of *Aspergillus oryzae* NS4 (Yamada, O. et al., Biosci. Biotech. Biochem., 61(8), 1367-1369 (1997)).

Among these vectors, when a vector containing a promoter is used, the EAP can be expressed by inserting a DNA encoding the EAP downstream to the promoter in frame. For example, since pUNG and pMARG have a promoter for glucoamylase gene (glaA) and α-amylase gene (amyB terminator), respectively, the EAP can be expressed under the control of the promoter by inserting a DNA encoding the EAP (for example the region including nucleotide position Nos. 1 to 1497 of SEQ ID NO: 6) down stream to the promoter in frame. When a vector which does not contain a promoter is used, such as pUSC, the EAP can be expressed by introducing it into the host filamentous fungus by the co-transformation thereof with a plasmid such as pUC19 containing a DNA of the present invention inserted therein. Thus obtained filamentous fungi or EAPs may be used for the method of the present invention.

Vectors, promoters and markers described in the literatures shown in below Table 1 may be used depending on the host filamentous fungus. In Table 1, the promoters are shown in terms of the enzymes encoded by the genes naturally regulated by the promoters.

TABLE 1

| Literature | Promoter | Marker | Host filamentous fungus |
|---|---|---|---|
| JP-Kokai No. 4-503450 | Neutral α-amylase | argB | *Aspergillus niger* |
|  |  | argB | *Aspergillus niger* |
|  |  | trpC | *Aspergillus nidulens* |
|  |  | amdS | *Aspergillus nidulans* |
|  |  | pyr4 | *Aspergillus nidulans* |
|  |  | DHFR | *Neurospora crassa* |
|  |  |  | *Neurospora crassa* |
| JP-Kokai No. 62-272988 | Taka-amylase | | *Aspergillus oryzae* |
|  | Aspartic protease | | *Rhizomucor miehei* |
|  | Lipase | | *Rhizomucor miehei* |
|  | Glucoamylase, lipase | | *Aspergillus niger* |
|  | Amylase, glucoamylase, cellulase | | |
|  | Protease, glycolytic enzyme | | |
| JP-Kokai No. 7-51067 | Taka-amylase | | genus *Aspergillus* |
| JP-Kokai No. 7-115976 | New promoter sequence is given | | *Aspergillus oryzae* |
| JP-Kokai No. 7-59571 | New promoter sequence is given | | *Aspergillus oryzae* |
| Nihon NougeiGakkaishi Vol. 71, No. 10 (1997) 1018-1023 | α-Amylase (anyB) | | *Aspergillus oryzae* |
|  | Glucoamylase (glaA) | | *Aspergillus oryzae* |
|  | Glucosidase (agdA) | | *Aspergillus oryzae* |

For the transformation of filamentous fungi, any known methods can be employed in addition to the methods described in the literatures in the table. For example, *Aspergillus oryzae* may be transformed as described below.

The cells (conidia) are inoculated in DPY medium (2% glucose, 1% peptone, 0.5% yeast extract, pH 5.0), and they are cultured at 30° C. for about 24 hours with vigorously shaking. The culture is filtered through Myracloth (CALBIO CHEM Co.) or a sterilized gauze or the like to recover the cells. The cells are washed with sterilized water and thoroughly drained. The cells are placed in a test tube. An enzyme solution (1.0% Yatalase; Takara Shuzo Co., Ltd.) or 0.5% NovoZyme (Novo Nordisk) and 0.5% cellulase (for example, Cellulase Onozuka; Yakult Co., Ltd.), 0.6 M $(NH_4)_2SO_4$ and 50 mM malic acid, pH 5.5) are added thereto and they are gently shaken at 30° C. for about 3 hours. The degree of the protoplastization is monitored with a microscope. When good condition is observed, the protoplasts are stored on ice.

The enzymatic reaction mixture is filtered through Myracloth to remove the cell residue. An equal amount of buffer A (1.2 M sorbitol, 50 mM $CaCl_2$, 35 mM NaCl and 10 mM Tris-HCl, pH 7.5) is added to the protoplast-containing filtrate, and the obtained mixture is placed in ice. After the centrifugation of the mixture at 1,500 to 2,500 rpm at 0° C. for 5 to 10 minutes, the centrifugation is slowly stopped. The pellets are washed with buffer A and then suspended in a suitable amount of buffer A. 20 μl or less of DNA solution (5 to 10 μg) is added to 100 to 200 μl of the protoplast suspension, and the obtained suspension is placed on ice for 20 to 30 minutes. 250 μl of buffer B (60% polyethylene glycol 6000, 50 mM $CaCl_2$, 10 mM Tris-HCl, pH 7.5) is added to the obtained mixture. After gently mixing, additional 250 μl of buffer B is added thereto and gently mixed. Then 850 μl of buffer B is added to the mixture and gently mixed, and then the mixture is left to stand at room temperature for 20 minutes. To the mixture 10 ml of buffer A is added and the test tube is inverted to mix them. After centrifugation at 1,500 to 2,500 rpm at 0° C. for 5 to 10 minutes, the pellets are suspended in 500 μl of buffer A.

A suitable amount of the suspension thus obtained is added to 5 ml of a top agar which has been previously aliquoted and pre-warmed and the mixture is overlaid on the lower layer medium (a selection medium prepared depending on the marker and containing 1.2 M sorbitol), and cultured at 30° C. The grown cells are subcultured on a selection medium to confirm that they are the transformants. It may be preferable to prepare the recombinant DNA from the cells to confirm the introduction of the DNA encoding the EAP by restriction enzyme analysis or Southern analysis and the like.

The EAP gene is expressed and EAP is produced by culturing the transformants thus obtained under the conditions suitable for the promoter used. For example, when *Aspergillus oryzae* is used as the host and a glucoamylase promoter is used as the promoter, spores of transformed *Aspergillus oryzae* are suspended in a medium containing wheat bran, potassium phosphate, and the like, and they are cultured at about 30° C. for about 3 days to produce the EAP. If necessary, the culture is diluted with distilled water or the like and then treated with a homogenizer or the like to obtain a crude enzyme extract containing EAP. The obtained crude extract can be treated by the gel filtration or a chromatography to further purify the EAP. The EAP thus obtained can be further purified by salting out, isoelectric precipitation, gel filtration, ion chromatography, reverse phase chromatography or the like and used for releasing acidic amino acids from peptides.

It is also possible to obtain a seasoning or foods and beverages such as protein hydrolysates, which have a high free amino acids content and have an improved taste and/or flavour, by admixing the culture of the transformed microorganism having increased EAP activity as a whole with protein raw materials, optionally together with a proteolytic enzyme (a protease), and treating them on the proteins or the mixture of proteins. The protein raw materials to be reacted include any proteins used for foods such as soybean, wheat, wheat gluten, commeal, milk casein, bonito, dried bonito, fish meal and the like. They may be also various processed proteins such as defatted soybean, puffed proteins or solubilized proteins, or they may be isolated proteins prepared from these various raw materials. When proteolytic enzymes are used, they may be those which are commercially available and may include other enzymes such as cell-wall digesting enzymes. Proteolytic enzymes produced by *Aspergillus* or *Bacillus* may be used, which include marketed enzyme preparations such as UMAMIZYME™, PROTEASE M™, FLAVOURZYME™ and ALCALASE™.

The foods which contains proteins or peptides of which taste and/or flavour may be improved by acting the glutamic acid- and/or aspartic acid-specific peptidase on them may include a wide range of various foods, for example, they include, but are not limited to, brewed or fermented foods such as soy sauce and miso, dairy foods such as cheese and yogurt, beverages such as vegetable juice and fruit juice, soybean products such as soy milk and tofu (soybean curd), wheat products such as bread or noodle, foods made from fish paste and water such as fish cake and fish sausage and meat products such as ham and sausage.

As for the practical conditions under which the culture of the transformed microorganism or the crude enzyme is treated on proteins, for example, a protein raw material having a concentration of 0.2 to 50%, preferable 1 to 20%, is mixed with the cultured product of the transformed microorganism, optionally in the presence of a proteolytic enzyme, to conduct the reaction at 5 to 55° C., preferably 30 to 55° C., for 1 minute to 10 days, preferably 1 hour to 10 days.

After the completion of the reaction, insoluble matters such as the unreacted protein materials or the cells are removed by an ordinary separation method such as centrifugation or filtration. If necessary, the product can be concentrated under reduced pressure or by reverse osmosis or the like, and the concentrated product may be dried or granulated by a drying process such as freeze-drying, reduced-pressure drying or spray-drying. Thus, foods and beverages having a high free glutamic acid content and improved taste and/or flavour can be obtained, including a seasonings and protein hydrolysates.

EXAMPLES

Example 1

Cloning of Genomic DNA Encoding *Aspergillus nidulans* EAP

The cDNA database of *Aspergillus nidulans* (http://www.genome.ou.edu/fungal.html) was used for a homology search, using the sequence of the aminopeptidase from germinating soybean, and ESTp0f10a1.f1 having high homology was identified.

The cloning of *Aspergillus nidulans* EAP from *Aspergillus nidulans* cDNAs was conducted as follows based on this information.

*Aspergillus nidulans* A26 strain (purchased from Fungal Genetics Stock Center, Department of Microbiology, University of Kansas Medical Center) was cultured with shaking at 30° C. for 48 hours in 50 ml of YG medium (0.5% of yeast extract, 2.5% of glucose, 0.1% or trace elements*, pH6.5 (*trace elements=$FeSO_4.7H_2O$ 0.1%, $ZnSO_4.7H_2O$ 0.88%, $CuSO_4.5H_2O$ 0.04%, $MnSO_4.4H_2O$ 0.015$Na_2B_4O_7.10H_2O$ 0.01%, $(NH_4)_6MoO_{24}.4H_2O$ 0.005%).

The cells were harvested, frozen in liquid nitrogen and crushed in a mortar. Total RNA was prepared from the crushed mixture by using RNeasy Plant Mini Kit (QIAGEN) and mRNAs were prepared by using oligotex-dT30<Super>mRNA Purification Kit (TaKaRa). The cDNAs were synthesized from the mRNAs by using TaKaRa RNA PCR Kit (AMV) Ver. 2.1 (TaKaRa). The full length cDNA for EAP was cloned by PCR and by 5' RACE method using oligonucleotides having the following sequences as primers, which had been designed from the sequence of *Aspergillus nidulans* ESTp0f10a1.f1, and the obtained cDNAs as templates.

```
(Primer for 5' terminal)
CGC ATT CCG ACG TTG GCT ATC C      (SEQ ID NO:17)

(Primer for 3' terminal)
ATG TTG GAA GAG CTC TTG AAG AG     (SEQ ID NO:18)
```

PCR reaction was conducted by heat-denaturation at 94° C. for 3 minutes, followed by 25 cycles of 94° C. for 30 seconds, 55° C. for 30 seconds and 72° C. for 30 seconds. As a result, a DNA fragment having the expected size (about 1000 bp) was amplified, which was in turn inserted into the plasmid pUC19. *Escherichia coli* JM109 was transformed with this plasmid, and the plasmid DNA was prepared from the transformed bacteria to determine the nucleotide sequence. This revealed that the sequence was identical to the sequence shown in the EST database.

Then, 5' RACE and 3' RACE methods were used to obtain the entire ORF sequence from *Aspergillus nidulans*. The PCR reaction was conducted at 94° C. for 9 minutes for heat denaturation followed by 30 cycles of 94° C. for 30 seconds, 55° C. for 30 seconds and 72° C. for 30 seconds with a final reaction at 72° C. for 5 minutes. The 5' ORF sequence was determined by 5' RACE using the primers shown in SEQ ID NOs: 19 and 20, and the entire ORF in the 3' RACE region was determined by using SEQ ID NO:21. An amplified fragment of about 1500 bp containing the entire ORF was obtained by PCR using the primers shown in SEQ ID NOs:22 and 23. The nucleotide sequence of the DNA fragment was shown in SEQ ID NO:2 and the amino acid sequence deduced from the nucleotide sequence was shown in SEQ ID NO:3.

The *Aspergillus nidulans* EAP cDNA fragment was inserted into the Hinc II site of pUC19. The expression plasmid pUCtrpnidGX was also constructed where a trp promoter was connected upstream to the inserted sequence. An *Escherichia coli* JM109 stain transformed with the resulting plasmid was obtained.

(Primer for 5' RACE)
TAG GGA ACA GTT GAG TCT C          (SEQ ID NO:19)

(Primer for 5' RACE)
TCC GTG TGA GCC CCG ATC ATG        (SEQ ID NO:20)

(Primer for 3' RACE)
TCC CGC TAC AAC TCT TTG TCG T      (SEQ ID NO:21)

(Primer for 5' terminal)
ATG ACG TCT AAT CTA ACG AAG        (SEQ ID NO:22)

(Primer for 3' terminal)
GAT TCA CTA GCC CTC GCA CTA C      (SEQ ID NO:23)

Example 2

Cloning of cDNA Homologous to *Aspergillus nidulans* EAP From *Aspergillus oryzae*

(1) Obtaining cDNA from *Aspergillus oryzae*

*Aspergillus oryzae* RIB40 (ATCC42149) was cultured at 30° C. for 64 hours in 50 ml of a medium containing 1.5% soybean isolate. The bacterial cells were collected by centrifugation to yield 1 g of cells. The cells were immediately frozen in liquid nitrogen and crushed in a mortar, from which a total RNA was prepared with Plant Mini Kit (QIAGEN) and mRNAs were prepared with olligotex-dT30<Super>mRNA Purification Kit (TaKaRa). cDNAs were synthesized from the mRNAs by using TaKaRa RNA PCR Kit (AMV) Ver.2.1 (TaKaRa).

(2) Cloning of Aminopeptidase Corresponding to the *Aspergillus nidulans* EAP From *Aspergillus oryzae*

Based on the EAP sequence from *Aspergillus nidulans* obtained in Example 1, a cDNA homologous to the *Aspergillus nidulans* EAP was cloned from *Aspergillus oryzae* by 3' RACE using the oligonucleotide shown in SEQ ID NO:24 and dT primer adapter primer and by 5' RACE using SEQ ID NOs:25 and 26.

(5' terminal primer for 3' RACE)
TCC ACC TTG ATC GCC AGG AGA CTT    (SEQ ID NO:24)

(Primer for 5' RACE)
TAG GGA ACA ATT GGG TCT C          (SEQ ID NO:25)

(Primer for 5' RACE)
GGC TTC CAT TTC TTG CCG            (SEQ ID NO:26)

The 3' RACE reaction was conducted by heat denaturation at 95° C. for 9 minutes followed by 35 cycles of 94° C. for 30 seconds, 60° C. for 30 seconds and 72° C. for 1 minute. This resulted in a gene fragment of about 800 bp, which was homologous to the aminopeptidase EAP of *Aspergillus nidulans*. The 5' RACE reaction was conducted by 35 cycles of 94° C. for 30 seconds, 53° C. for 30 seconds and 72° C. for 1 minute. This resulted in a gene fragment of about 300 bp, which was homologous to the aminopeptidase EAP of *Aspergillus nidulans*. A nucleotide sequence of about 1500 bp containing the entire ORF was obtained by conducting PCR using the sequence shown in SEQ ID NOs:27 and 28. PCR reaction was conducted by 25 cycles of 94° C. for 30 seconds, 54° C. for 30 seconds and 72° C. for 45 seconds.

(Primer for 5' terminal)
ATG ACT TCG AAA ATC GCC CAA AAT TTG AAG    (SEQ ID NO:27)

(Primer for 3' terminal)
TCA GTC AAC AAA GAT TGT CTT TGA CGTG       (SEQ ID NO:28)

Determination of the nucleotide sequence of the resulting gene fragment revealed that the fragment contained the full length sequence which was homologous to the aminopeptidase EAP of *Aspergillus nidulans*. Therefore, the inventors concluded that the gene is the gene encoding the aminopeptidase of *Aspergillus oryzae*, which corresponds to the *Aspergillus nidulans* EAP. Additionally, a nucleotide sequence of about 1800 bp including 5 introns could be obtained by PCR using SEQ ID NOs: 27 and 28 as primers and the genomic DNA of *Aspergillus oryzae* as a template. The genomic sequence of *Aspergillus oryzae* including the 5 introns was shown in SEQ ID NO:4. The nucleotide sequence of the full length cDNA encoding the aminopeptidase of *Aspergillus oryzae* is shown in SEQ ID NO:6, and the amino acid sequence of *Aspergillus oryzae* is shown in SEQ ID NO:7.

*Escherichia coli* JM109 strain was transformed with a plasmid which had been obtained by inserting the fragment into pUC19 plasmid. The expression vector pUCtrpoGX was also obtained by connecting a trp promoter upstream to the cDNA.

Example 3

Cloning of cDNA of EAP from *Aspergillus niger*, which is Homologous to EAPs from *Aspergillus nidulans* and *Aspergillus oryzae*

(1) Obtaining the aminopeptidase cDNA from *Aspergillus niger*

*Aspergillus niger* (JCM2261) was cultured at 30° C. for 64 hours in 50 ml of a medium containing 1.5% soybean isolate. The bacterial cells were collected by centrifugation to yield 1 g of cells. The cells were immediately frozen in liquid nitrogen and crushed in a mortar, and the total RNA was prepared from the cells with Plant Mini Kit (QIAGEN) and mRNAs were prepared with olligotex-dT30<Super>mRNA Purification Kit (TaKaRa). cDNAs were synthesized from the mRNAs by using TaKaRa RNA PCR Kit (AMV) Ver.2.1 (TaKaRa).

(2) Cloning of *Aspergillus niger* EAP, Which Corresponds to the EAPs from *Aspergillus nidulans* and *Aspergillus oryzae*

Primers shown in SEQ ID NOs:29 and 30 were designed for the sequence region exhibiting 100% homology between the *Aspergillus nidulans* EAP obtained in Example 1 and the *Aspergillus oryzae* EAP. By using these primers, a partial cDNAs for aminopeptidase EAP were obtained from *Aspergillus niger*. The cloning of the cDNA for *Aspergillus niger* EAP, which is homologous to the EAPs from *Aspergillus nidulans* and *Aspergillus oryzae*, was conducted by 3' RACE using the partial cDNAs as templates, the oligonucleotide shown in SEQ ID NO:31 and dT adaptor primer, and by 5' RACE using SEQ ID NO:32. For 3' RACE, "3' RACE System for Rapid Amplification of cDNA Ends (Invitrogen)" was used and for 5' RACE, "5' RACE System for Rapid Amplification of cDNA Ends (Invitrogen)" was used.

```
(5' primer for obtaining partial
cDNAs)
TTG TCC TTT GTC AAT GC          (SEQ ID NO:29)

(3' primer for obtaining partial
cDNAs)
CGG ATA CTG TGC ATG CTT         (SEQ ID NO:30)

(Primer for 3' RACE)
CAA CAA GGG CCC TGT TAT C       (SEQ ID NO:31)

(Primer for 5' RACE)
CTT TGC CGA CTG AAC GGC         (SEQ ID NO:32)
```

The PCR reaction for 3' RACE was conducted by heat denature at 95° C. for 9 minutes followed by 35 cycles of 94° C. for 30 seconds, 60° C. for 30 seconds and 72° C. for 1 minute. This resulted in a gene fragment of about 120 bp, which was homologous to the aminopeptidase EAPs from *Aspergillus nidulans* and *Aspergillus oryzae*. The 5' RACE reaction was conducted by 35 cycles of 94° C. for 30 seconds, 53° C. for 30 seconds and 72° C. for 1 minute. This resulted in a gene fragment of about 100 bp, which was homologous to the aminopeptidase EAPs from *Aspergillus nidulans* and *Aspergillus oryzae*. A nucleotide sequence of about 1500 bp containing the entire ORF was obtained by conducting PCR using the sequence shown in SEQ ID NOs:33 and 34. PCR reaction was conducted by 25 cycles of 94° C. for 30 seconds, 54° C. for 30 seconds and 72° C. for 45 seconds.

```
(Primer for 3' terminal)              (SEQ ID NO:33)
GTA AGG AGG TTT AAA ATG ACT TCG AAA ATC GCC C (Primer for 5' terminal)              (SEQ ID NO:34)
CTA ATC AAC AAA GAT GGT CTT GGA AAG ATT GGC G
```

The nucleotide sequence of the full length cDNA encoding the EAP of *Aspergillus niger* was determined from the gene fragment, which is shown in SEQ ID NO:9. The amino acid sequence of the *Aspergillus niger* EAP is shown in SEQ ID NO:10.

*Escherichia coli* JM109 strain was transformed with a plasmid which had been obtained by inserting the fragment into pUC19 plasmid. The expression vector pUCtrpnigGX was also obtained by connecting a trp promoter upstream to the cDNA. *Escherichia coli* JM109 strain was transformed with the resulting plasmid.

Example 4

Cloning of a Gene Homologous to Soybean GX from *Saccharomyces*

(1) Obtaining the Genomic DNA from *Saccharomyces*

*Saccharomyces* YPH500 (IFO10506) was cultured overnight at 30° C. in 50 ml of YPD (1% yeast extract, 2% peptone and 2% glucose) supplemented with adenine. The genomic DNA was extracted from the culture medium by using "Gen Toru-Kun (for Yeast)" (TaKaRa).

(2) Cloning of EAP Corresponding to Soybean GX from *Saccharomyces*

The genome database of *Saccharomyces* was searched for sequences having homology to the sequence of soybean GX described in JP-Kokai No. 9-294583. As a result, a sequence having 43% homology was found and the positions of the initiation codon and the stop codon were also identified. The primers shown in SEQ ID NOs:35 and 36 were designed based on the sequence and a gene fragment for *Saccharomyces* EAP was cloned from the genomic DNA using these primers.

```
(5' primer)
CTA TGT TCA GGA TAC AAC TGA GAA    (SEQ ID NO:35)

(3' primer)
CAG TTT AGA CAA CAA TTT CAG ATT    (SEQ ID NO:36)
```

The nucleotide sequence of the full length DNA encoding the EAP of *Saccharomyces* was determined based on the gene fragment, which is shown in SEQ ID NO:12. The amino acid sequence of EAP of *Saccharomyces* is shown in SEQ ID NO:13.

*Escherichia coli* JM109 strain was transformed with a plasmid which had been obtained by inserting the fragment into pUC19 plasmid. The expression vector pUCtrpsGX was also obtained by connecting a trp promoter upstream to the cDNA. *Escherichia coli* JM109 strain was transformed with the resulting plasmid.

Example 5

Cloning of a Gene Homologous to Soybean GX from Coryneform Bacterium (1) Obtaining the Genomic DNA from a Coryneform Bacterium Coryneform bacteria (ATCC13869) were cultured overnight at 30° C. in 50 ml of LB medium (tryptone 1%, yeast extract 0.5% and NaCl 1%). The genomic DNA was extracted from the culture medium by using "Gen Toru-Kun (for Yeast)" (TaKaRa).

(2) Cloning of EAP Corresponding to Soybean GX from a Coryneform Bacterium

The genome database for coryneform bacteria was searched for sequences having homology to the sequence of soybean GX described in JP-Kokai No. 9-294583. The homology of 48% was detected for a sequence encoding an aspartyl aminopeptidase. Primers shown in SEQ ID NOs:37 and 38 were designed based on the sequence and a gene fragment for coryneform bacterial EAP was cloned from the genomic DNA using the primers.

```
(5' primer)                              (SEQ ID NO:37)
GTA AGG AGG TTT AAA ATG CAT GTA ACT GAC GAT TTC
TTA AGT TTT ATT GCC C (3' primer)                              (SEQ ID NO:38)
TTA ATT TAC CAG ATA GGC TTC CAG GGC TT
```

The nucleotide sequence of the full length DNA encoding the EAP of coryneform bacterium was determined based on the gene fragment, which is shown in SEQ ID NO:15. The amino acid sequence of EAP of *Saccharomyces* is shown in SEQ ID NO:16.

*Escherichia coli* JM109 strain was transformed with a plasmid which had been obtained by inserting the fragment into pUC19 plasmid. The expression vector pUCtrpcGX was also obtained by connecting a trp promoter upstream to the cDNA. *Escherichia coli* JM109 strain was transformed with the resulting plasmid.

Example 6

Mass Expression of EAPs from *Aspergillus nidulans*, *Aspergillus oryzae*, *Aspergillus niger*, Yeast and a Coryneform Bacterium in *Escherichia coli* JM109

(1) Purification *Aspergillus nidulans* EAP, *Aspergillus oryzae* EAP, *Aspergillus niger* EAP, Yeast EAP and Coryneform Bacterial EAP The bacteria transformed with pUCtrpGX were cultured with shaking at 30° C. for 8 hours in a refresh medium (tryptone 1%, yeast extract 0.5%, NaCl 0.5% and glucose 0.1%). Five (5) ml of the resulting culture was then further cultured at 37° C. for 20 hours in 350 ml of casamino acid medium ($Na_2HPO_4$ 0.6%, $KH_2PO_4$ 0.3%, $NH_4Cl$ 0.1%, NaCl 0.05%, casamino acid 1%, thiamine 0.0002%, $MgSO_4$ 1 mM, $CaCl_2$ 1 mM and glucose 0.1%). However, the culture temperature was 34° C. for the coryneform type. The bacterial cells were crushed according to the conventional procedures to obtain cell extracts. To the cell extracts ammonium sulfate was added and precipitated fractions at 40-65% of ammonium sulfate were collected. However, 0%-40% fraction was collected for yeast case. The resulting fractions were resuspended in 50 mM of a phosphate buffer (pH7.5) and separated on a gel filtration column which had been previously equilibrated with the phosphate buffer to obtain crude EAPs. The resulting enzyme solutions were concentrated by ultrafiltration. The crude EAPs were subjected to a further isolation process with anion exchange column (monoQ, Amersham Biotech.) to obtain the purified EAPs.

The resulting purified EAPs exhibited a molecular weight of about 300 to 480 kD on a native polyacrylamide gel and exhibited a molecular weight of about 40 to 60 kD on a denature polyacrylamide gel.

Example 7

Characterization of the Aminopeptidase EAPs

The aminopeptidase activity in the purified enzyme solutions prepared as above-described was determined as described below. To 0.16 ml of 5 mM Glu-Glu (in 50 mM HEPES buffer, pH7.5) 0.02 ml of the purified enzyme solution was added. The reaction was conducted at 37° C. for 10 minutes and the reaction was terminated by adding 0.02 ml of 20% acetic acid. The free Glu content was determined by Glutamic Acid Measurement Kit (Yamasa Shouyu). One unit of the activity was defined as the enzyme activity that librates 1 micromole of Glu per 1 minute.

The enzymatic properties of the resulting purified aminopeptidases are described below.

(i) Substrate Specificity

Figure 1C:
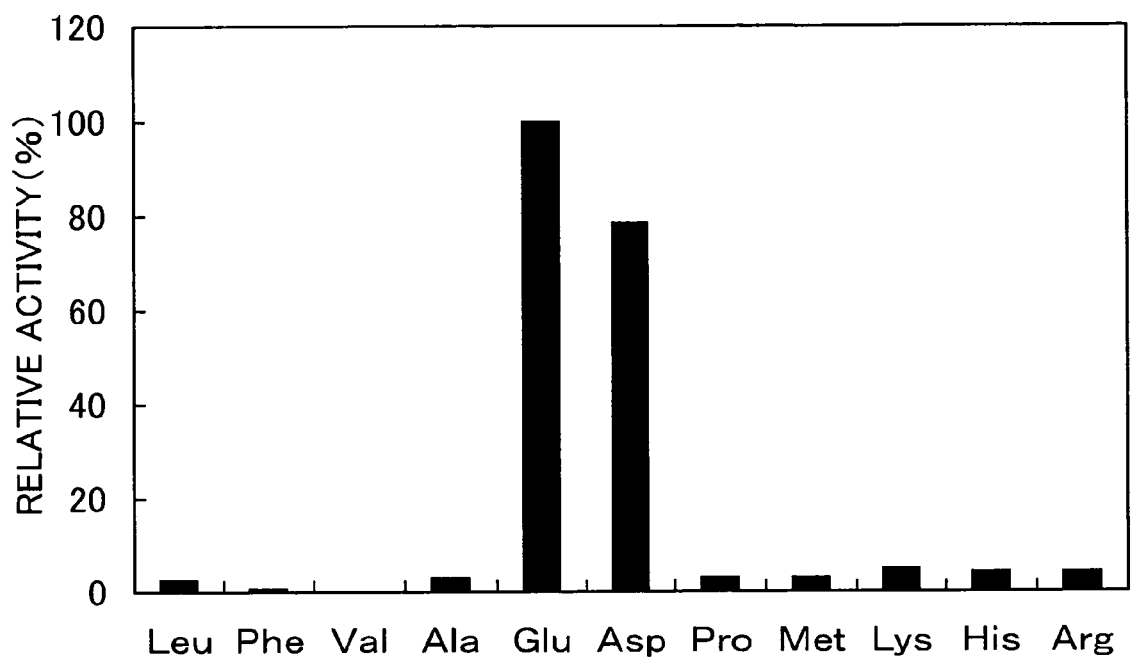
FIG. 1 is a graph showing the substrate specificity of the EAPs. (1A) *Aspergillus oryzae* EAP; (1B) *Aspergillus niger* EAP; (1C) Coryneform bacterial EAP; (1D) Yeast EAP.
Figure 1D:
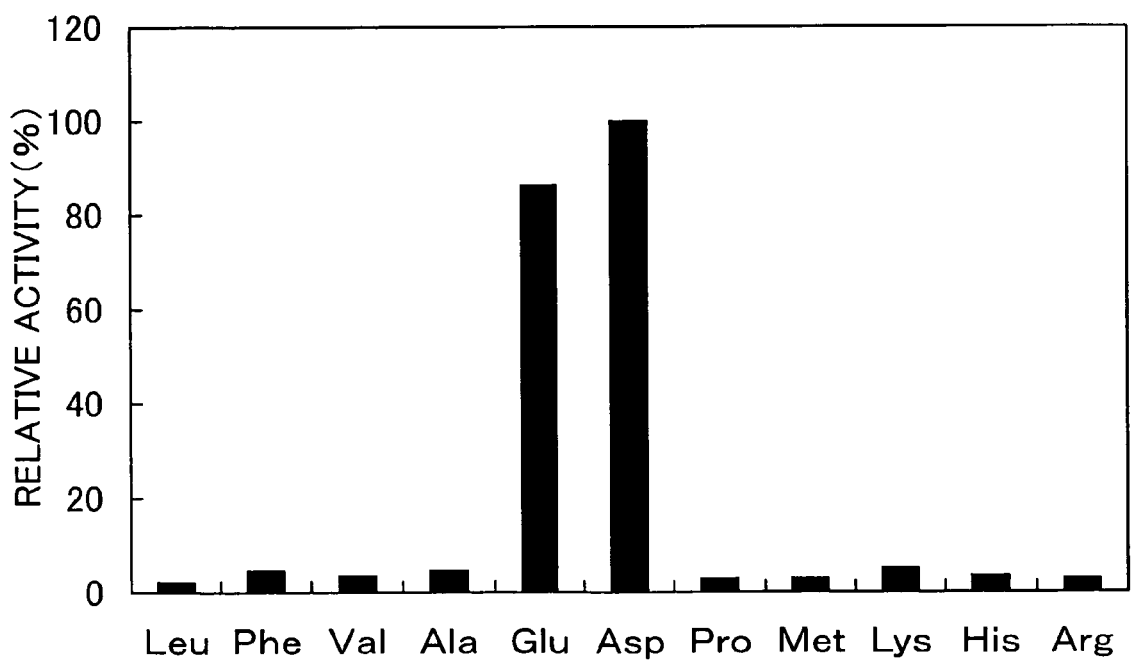

The activity of EAP can be also determined by using Glu-pNA as a substrate. Briefly, to 0.75 ml of 1 mM Glu-pNA (in 50 mM sodium phosphate buffer, pH7.5) 0.02 ml of the enzyme solution was added to allow the reaction for 10 minutes at 37° C. and 0.25 ml of 40% acetic acid was then added to stop the reaction. The absorbance of the reaction mixture was measured at 405 nm to determine the activity. One unit (U) of the activity was defined as the enzyme activity to liberate 1 micromole of paranitroanilide per 1 minute. The activity of hydrolyzing various X-pNAs was determined by using X-pNA instead of Glu-pNA. The relative activities were shown in FIG. 1 by assuming the maximum activity as 100. The enzymes were proved to hydrolyze N-terminal acidic acid amino acids efficiently and specifically, that is, two amino acids, glutamic acid and aspartic acid.

(ii) Temperature-Reaction Profile

Figure 2C:
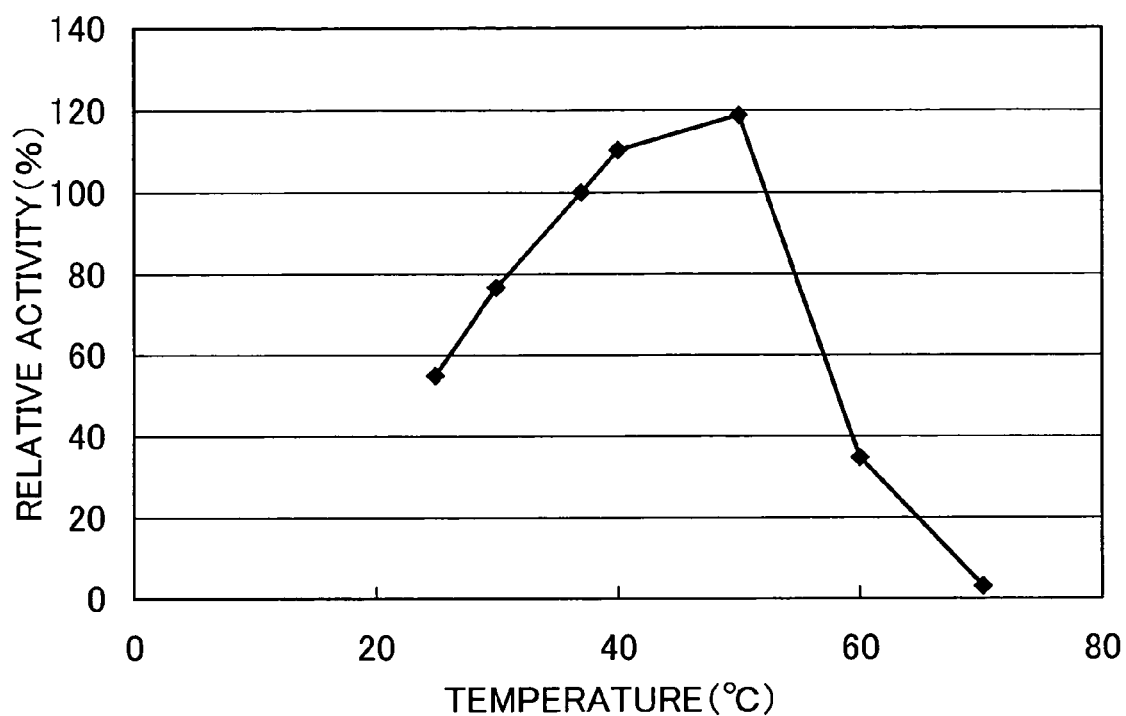
FIG. 2 is a graph showing the temperature-reaction profile. The horizontal axes indicate temperature (° C.) and the vertical axes indicate the relative activity of the aminopeptidases assuming the activity at 37° C. as 100. (2A) *Aspergillus oryzae* EAP; (2B) *Aspergillus nidulans* EAP; (2C) *Aspergillus niger* EAP; (2D) Coryneform bacterial EAP; (2E) Yeast EAP.
Figure 2D:
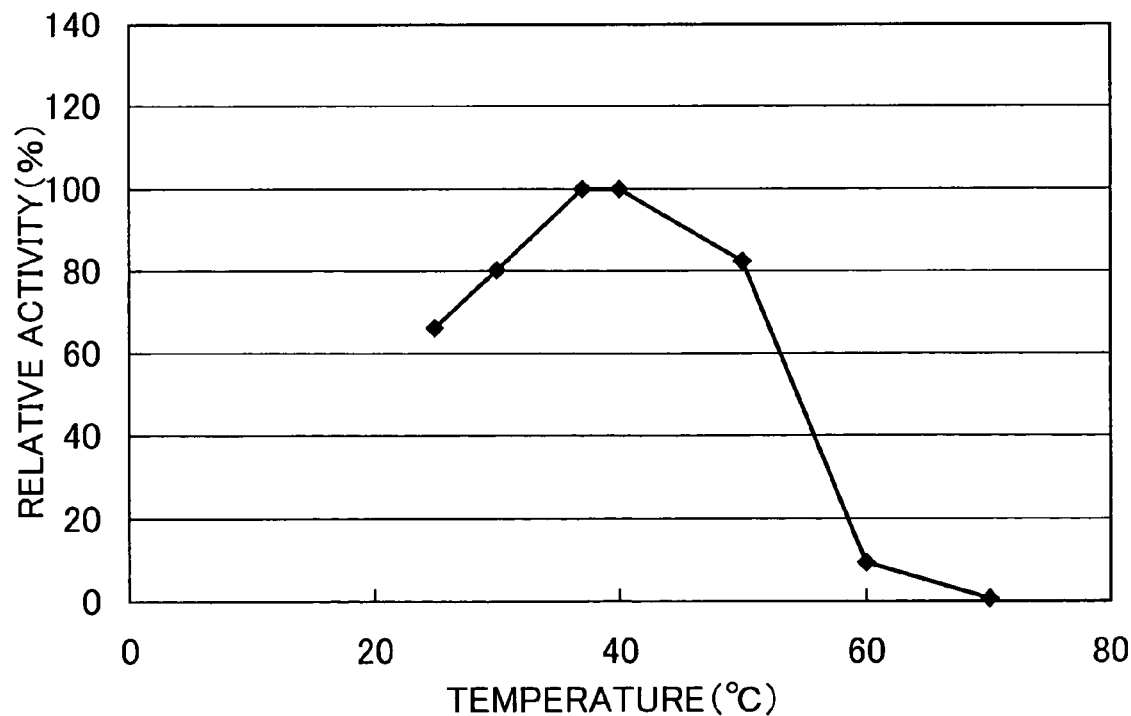
Figure 2E:
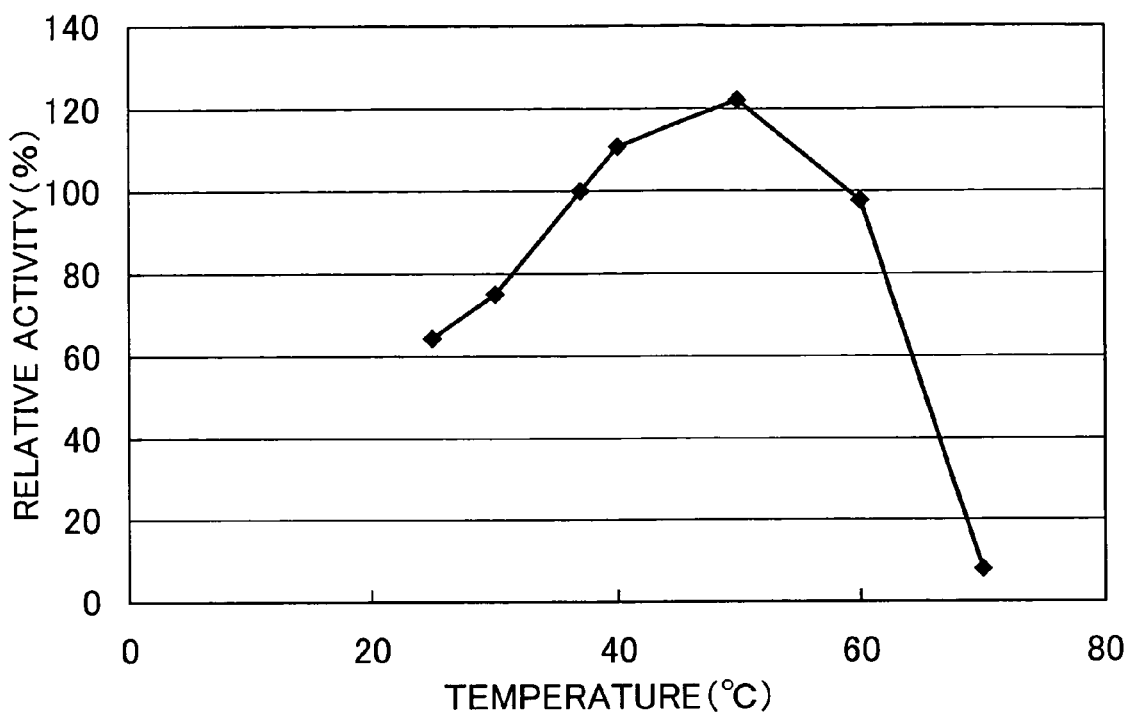
Figure 3A:
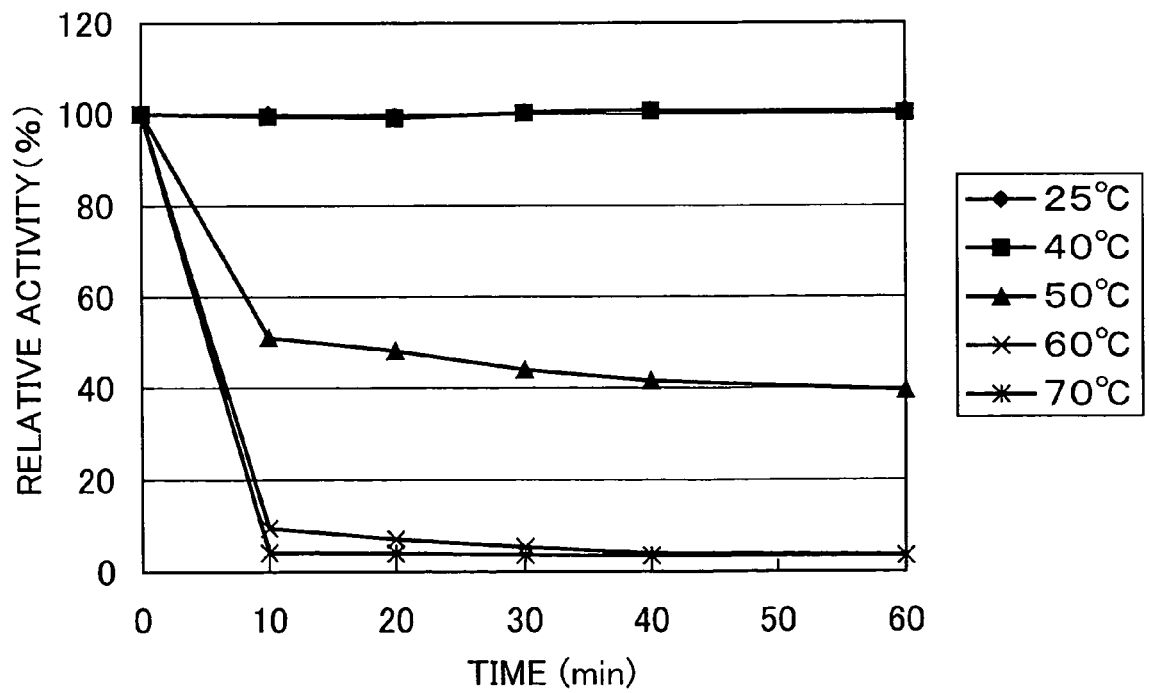
FIG. 3 is a graph showing the temperature-stability. The horizontal axes indicate the storage period and the vertical axes indicate the relative activity of the aminopeptidases assuming the activity at 0 minute storage as 100. (3A) *Aspergillus oryzae* EAP; (3B) *Aspergillus nidulans* EAP (3C) *Aspergillus niger* EAP; (3D) Coryneform bacterial EAP; (3E) Yeast EAP.
Figure 3B:
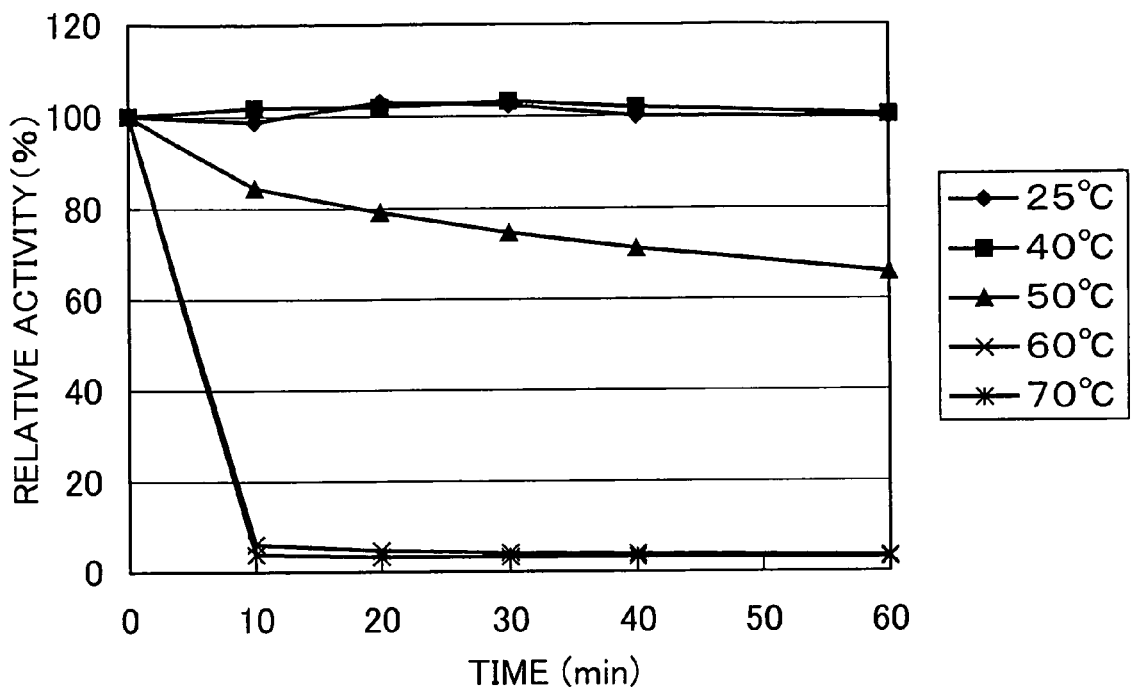
Figure 3C:
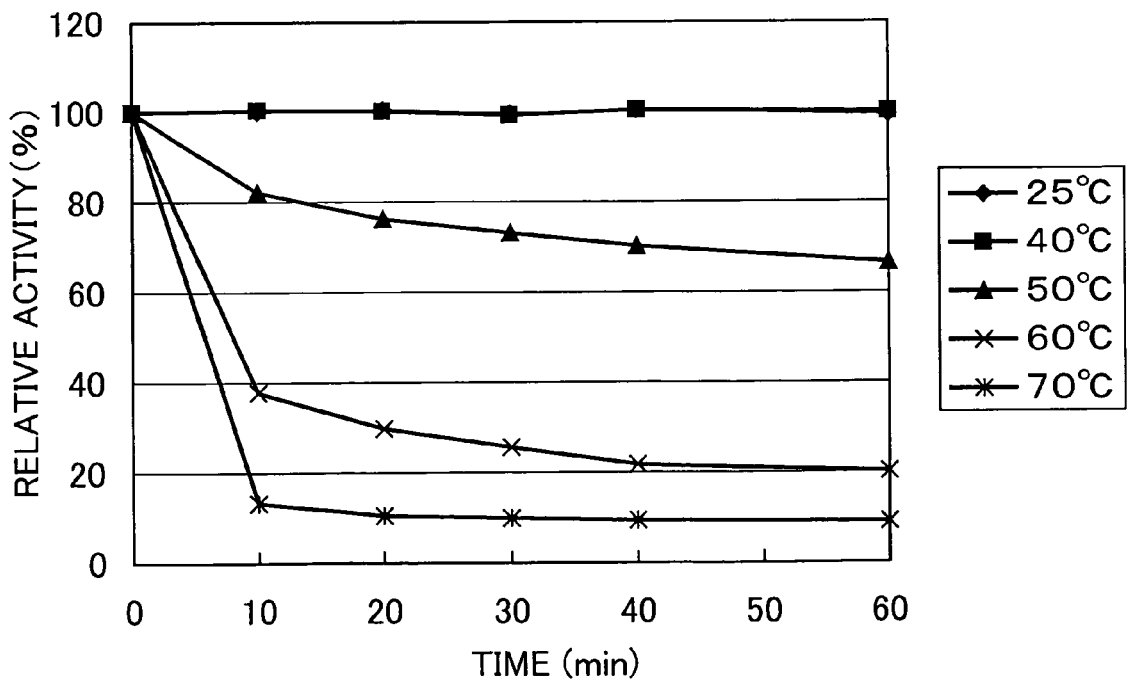
Figure 3D:
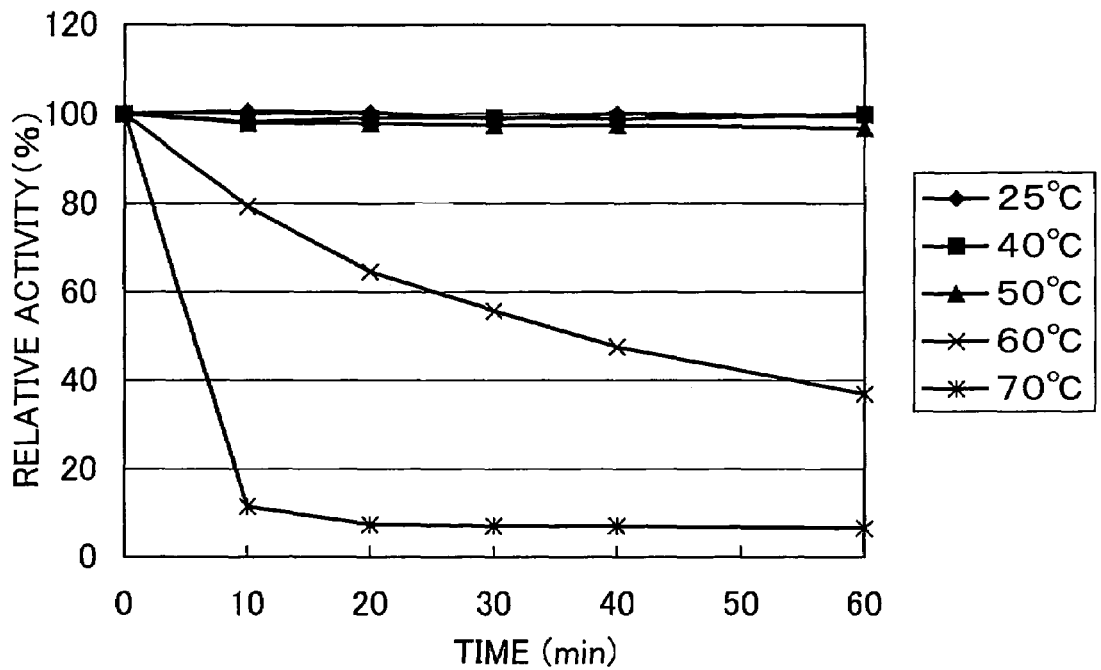
Figure 3E:
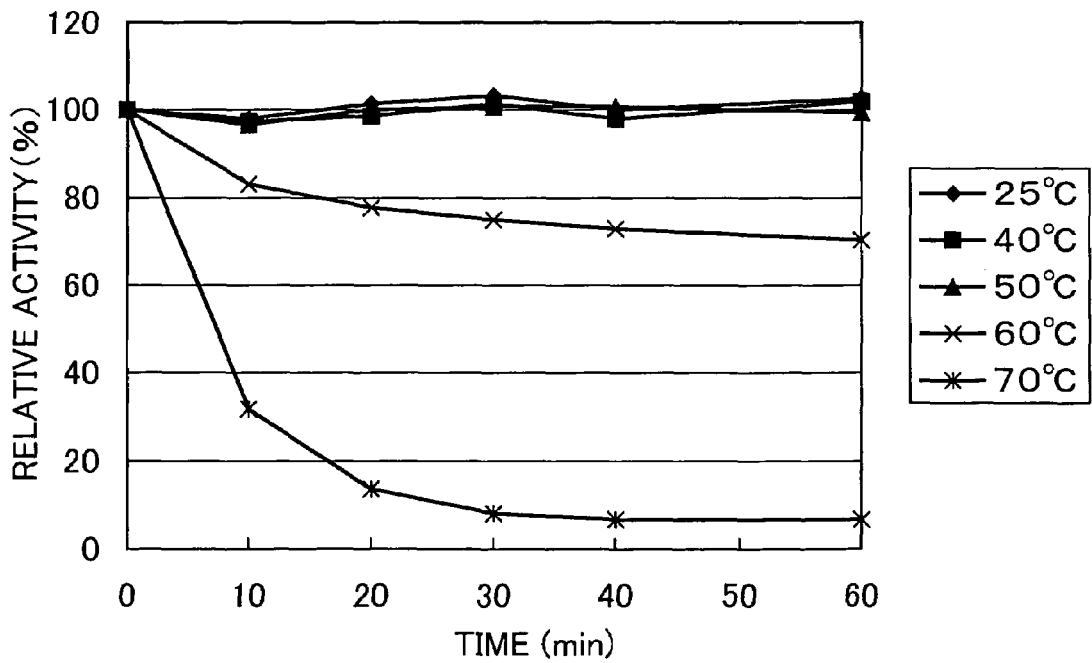
Figure 4A:
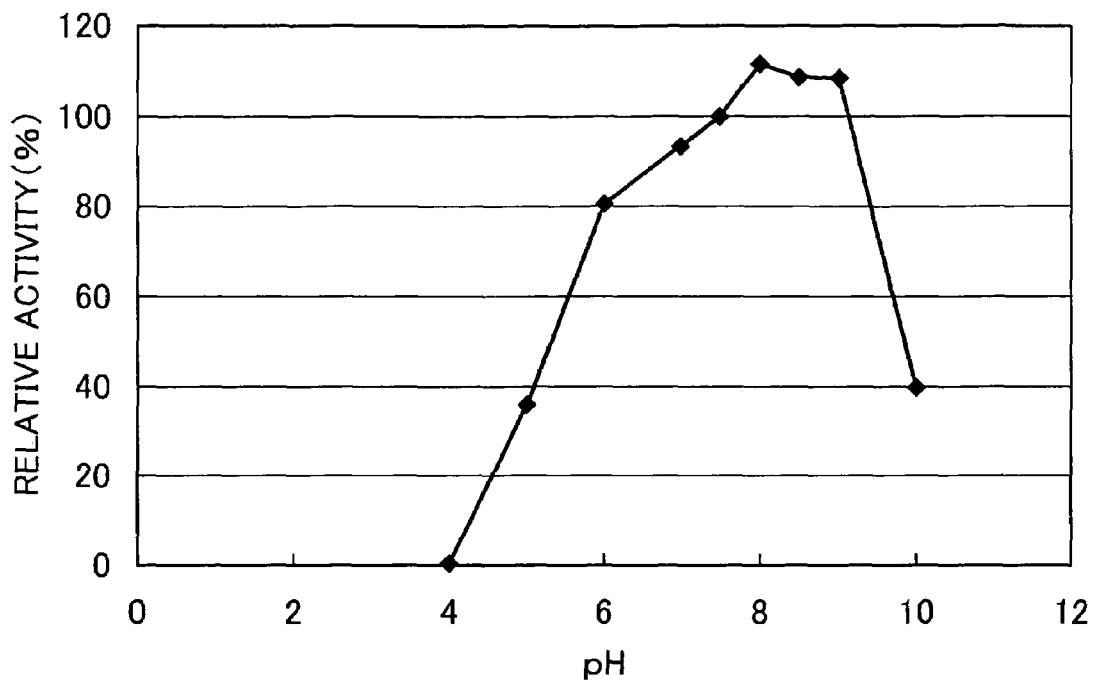
FIG. 4 is a graph showing the pH-reaction profile. The horizontal axes indicate the pH and the vertical axes indicate the relative activity of aminopeptidases assuming the activity at pH7.5 as 100. (4A) *Aspergillus oryzae* EAP; (4B) *Aspergillus nidulans* EAP (4C) *Aspergillus niger* EAP; (4D) Coryneform bacterial EAP; (4E) Yeast EAP.
Figure 4B:
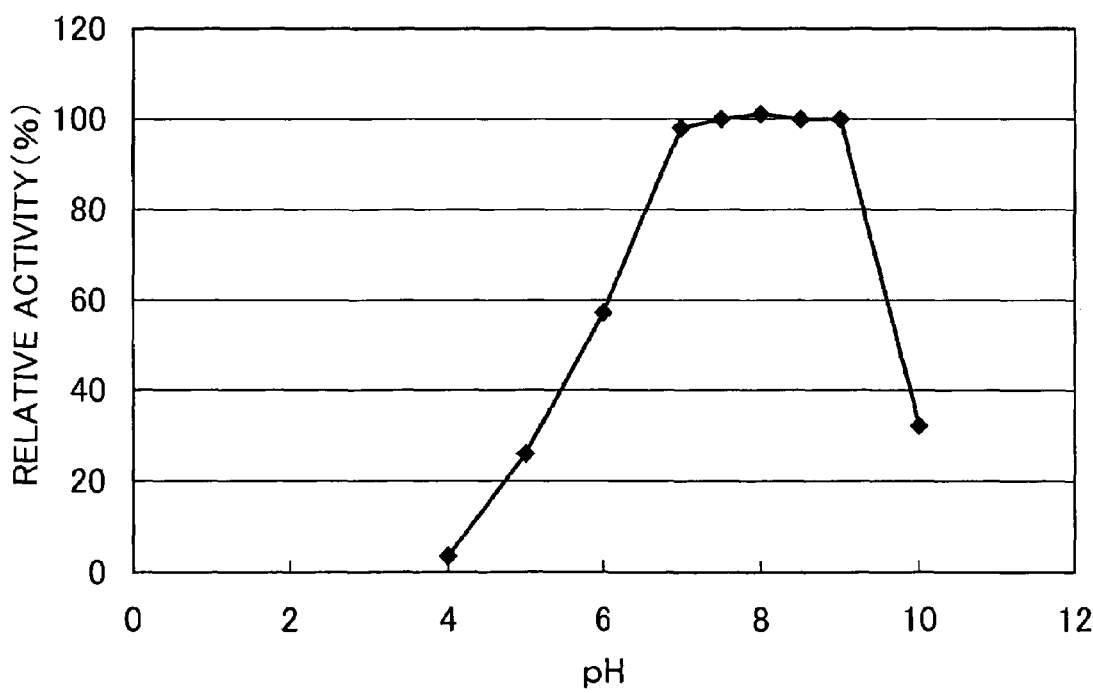
Figure 4C:
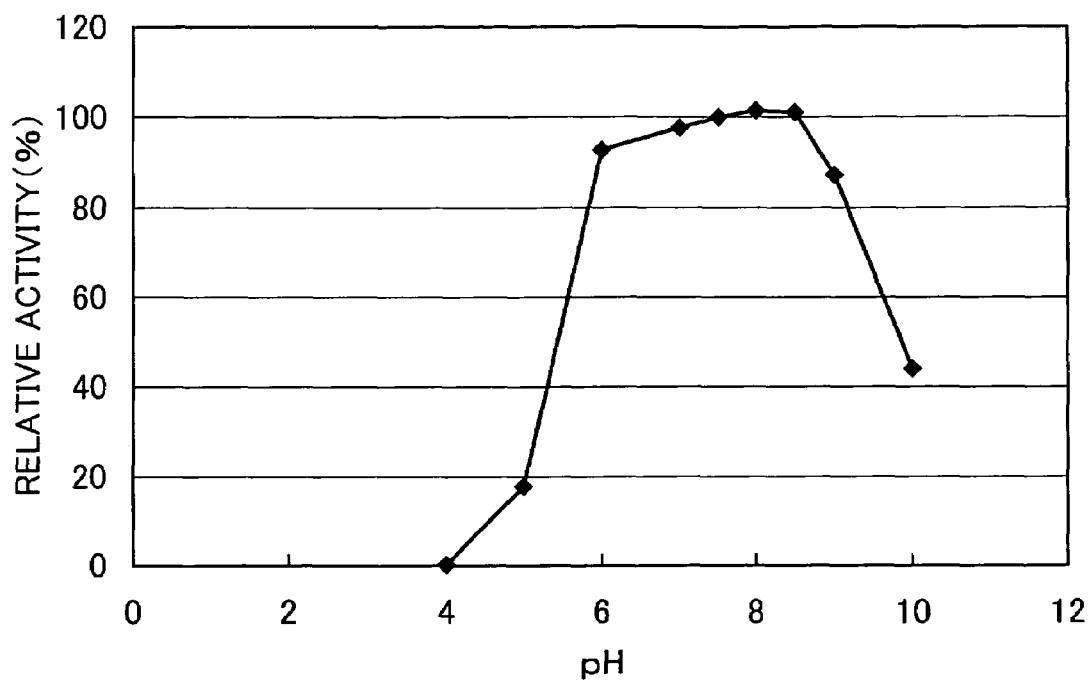
Figure 4D:
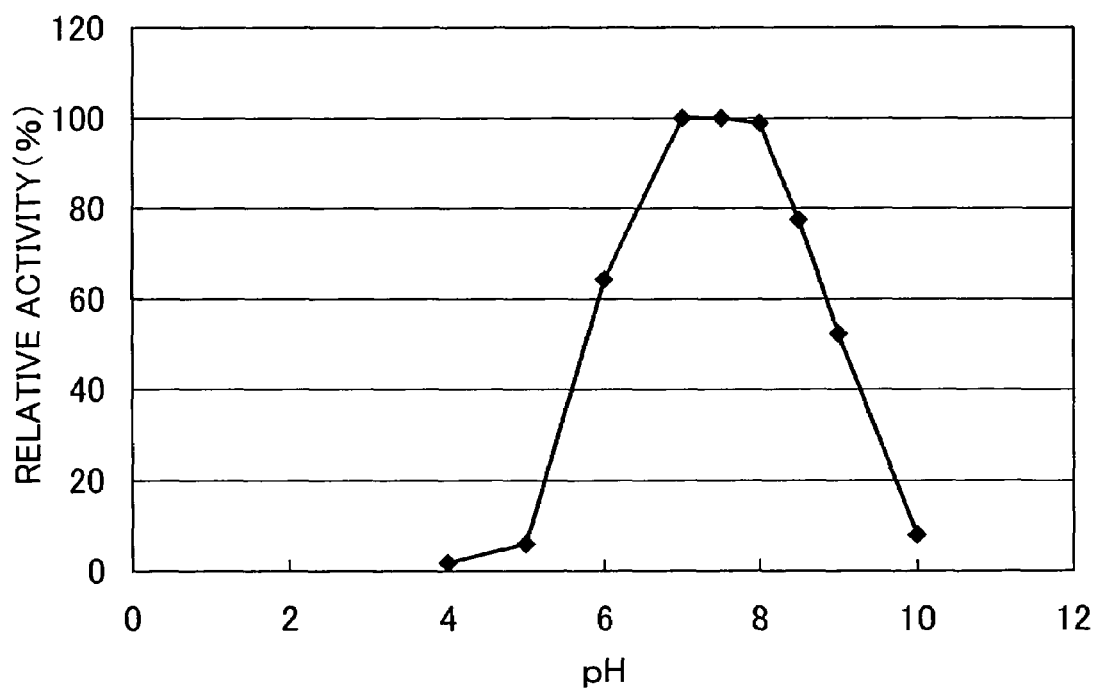
Figure 4E:
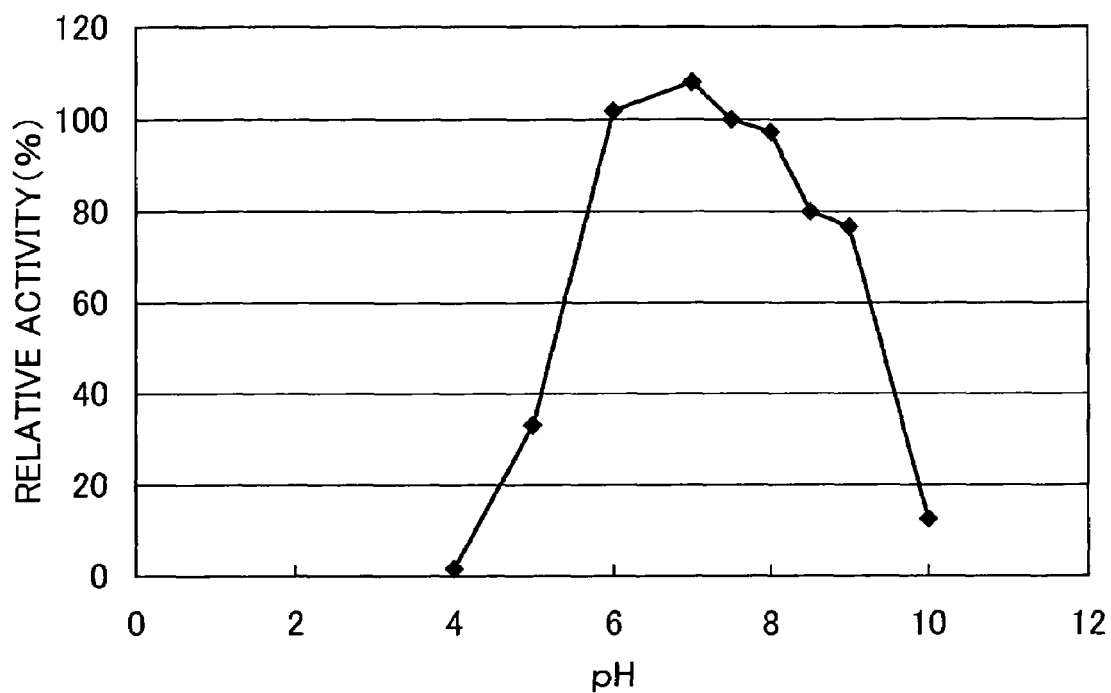
Figure 5A:
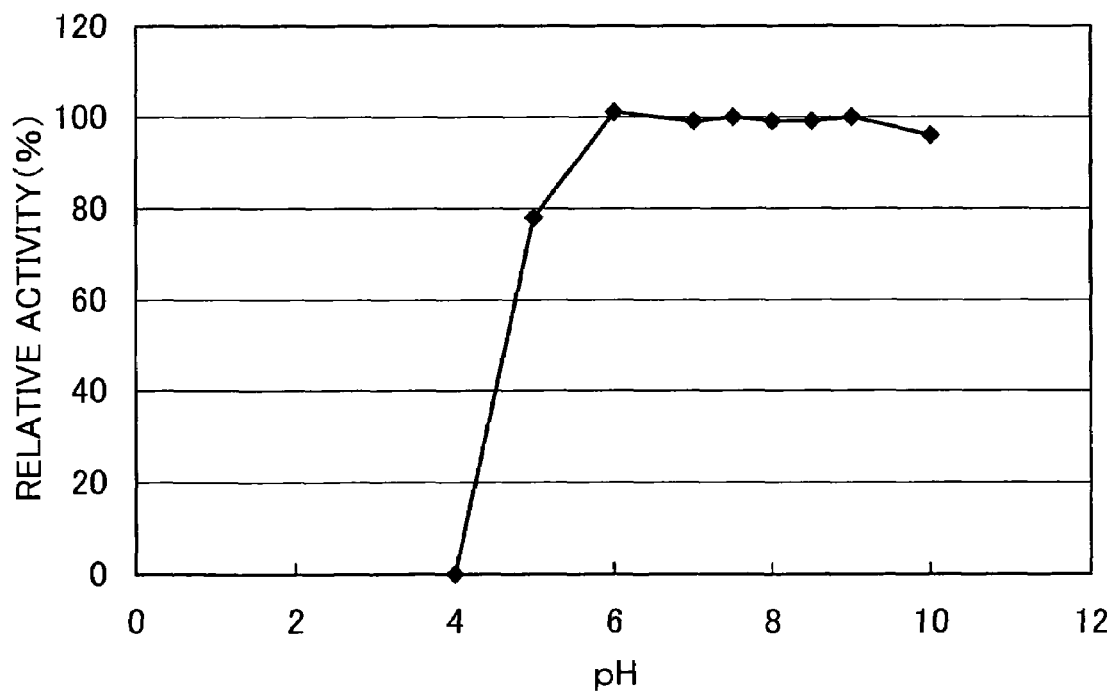
FIG. 5 is a graph showing the pH-stability. The horizontal axes indicate the pH of the buffer used for storage and the vertical axes indicate the relative activity of aminopeptidases assuming the activity before storage as 100. (5A)
Figure 5B:
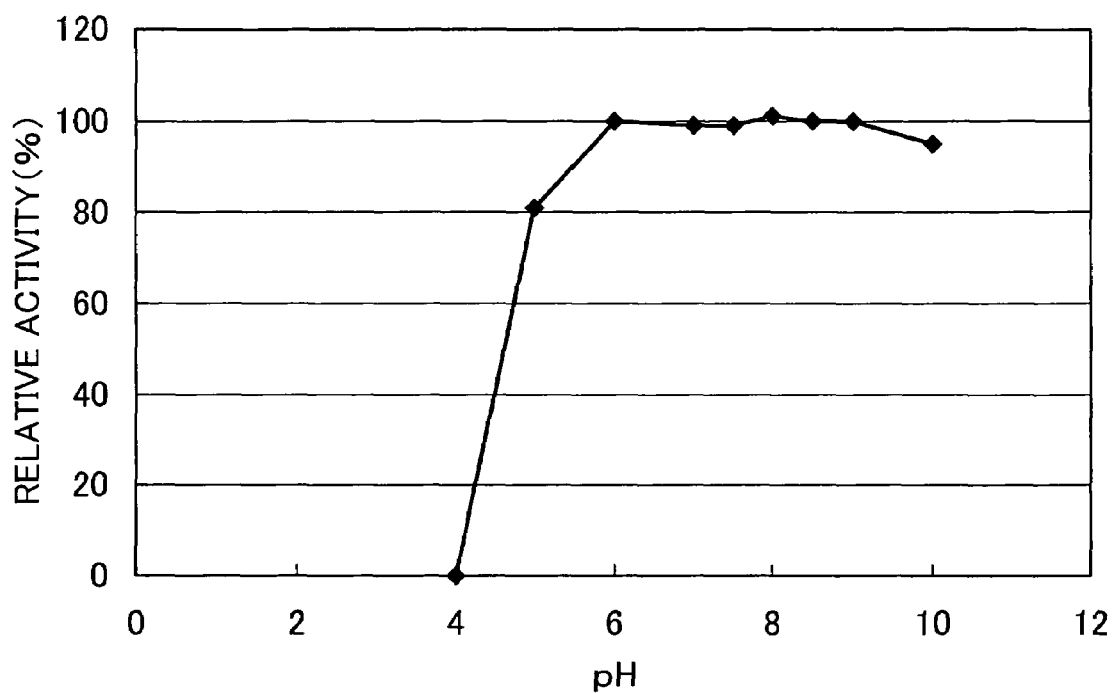
Figure 5C:
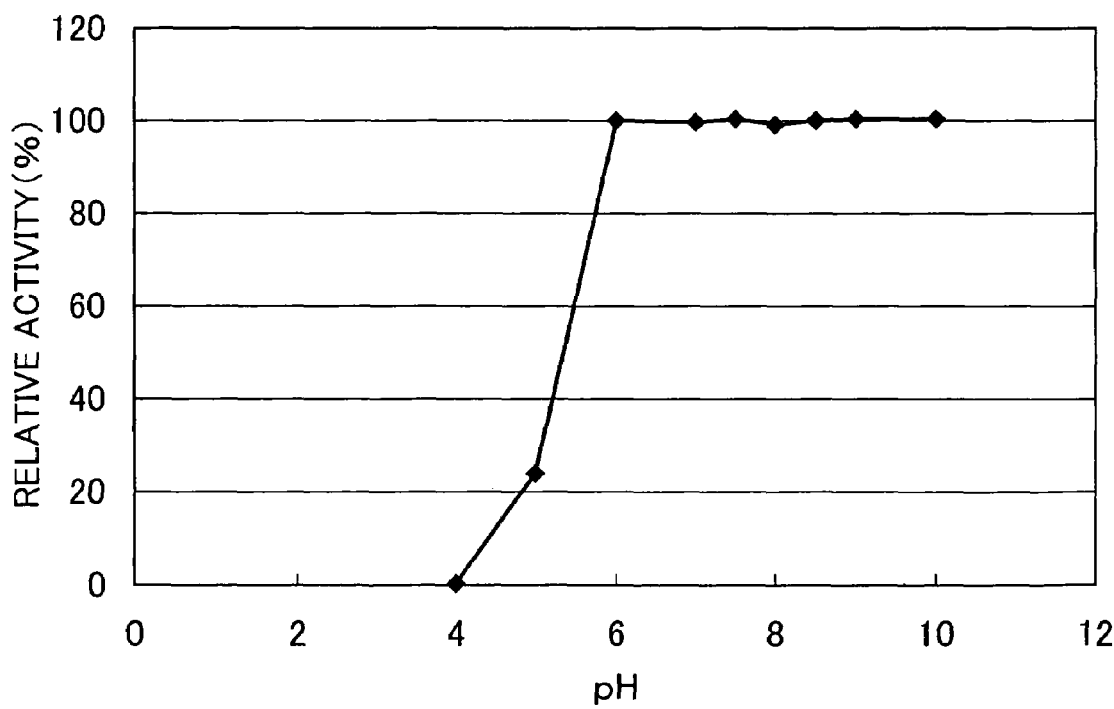
Figure 5D:
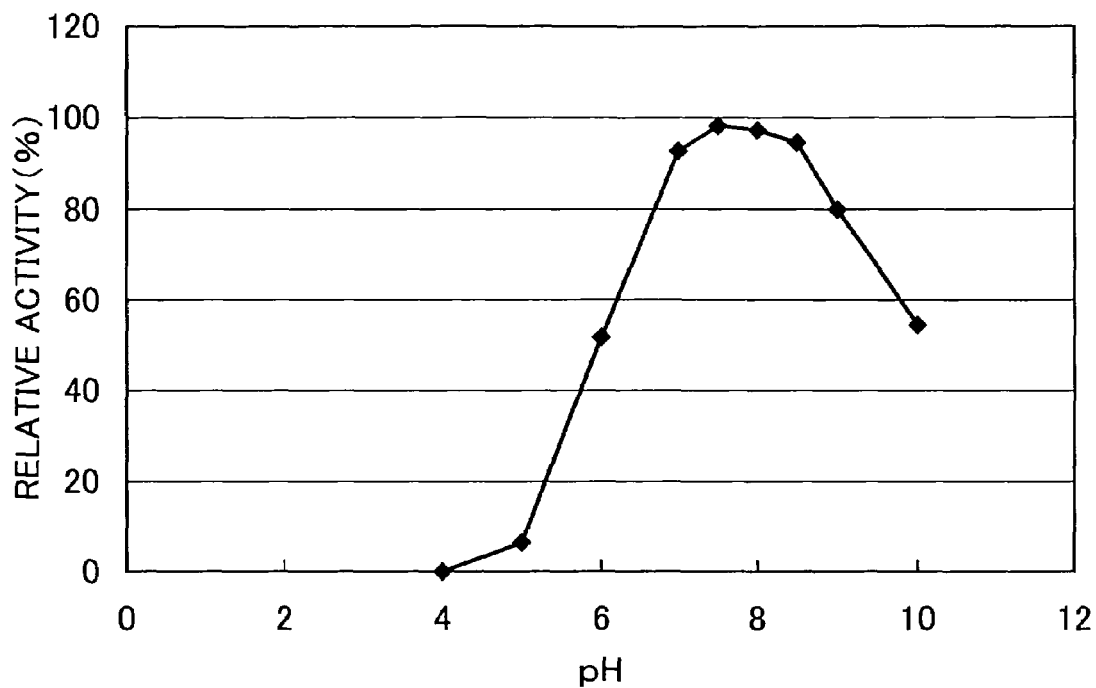
Figure 5E:
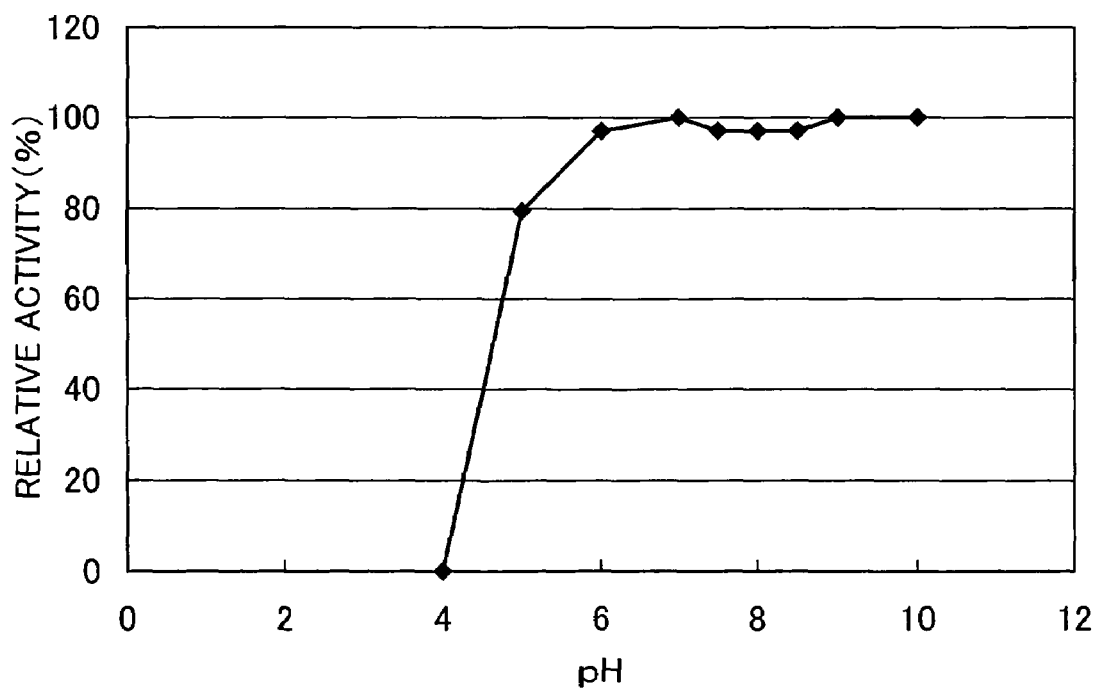

In the process for determination of the activity using Glu-Glu as a substrate, the EAP activity was determined at various temperatures. The relative activities were shown in FIG. 2 by defining the activity at 37° C. as 100. It can be seen from FIG. 2 that the relative activity is higher at a temperature of 30° C.-60° C., preferably at 37° C.-50° C.

(iii) Temperature-Stability

In the process for determination of the activity using Glu-Glu as a substrate, the EAP activity was determined according to the aforementioned method after keeping the enzyme at various temperature for 10, 20, 30, 40 or 60 minutes. The relative activities were shown in FIG. 3 by defining the activity at time 0 as 100.

*Aspergillus oryzae* EAP, *Aspergillus nidulans* EAP and *Aspergillus niger* EAP exhibited at least 80% remaining activity after keeping them at 25° C.-40° C., pH7.5 for 1 hour. The coryneform bacterial EAP and the yeast EAP exhibited at least 80% remaining activity after keeping them at 25° C.-50° C., pH7.5 for 1 hour and maintained at least 40% activity after heating them at 25-60° C. for 30 minutes as compared with the activity before heating.

(iv) pH-Reactivity Profile

In the process for determination of the activity using Glu-Glu as a substrate, GTA buffers having various pHs were added respectively to the reaction mixture to a final concentration of 50 mM instead of 50 mM HEPES buffer (pH7.5). The EAP activity at pH7.5 was defined to be 100. The activities at various pHs were shown in FIG. 4. As shown in FIG. 4, EAPs had at least 50% of the activities observed at the optimum pHs, in the range of pH6.0-9.0.

(v) pH-Stability

The EAP activities were determined according to the aforementioned method (pH7.5) after storing the purified enzymes at 0° C. for 24 hours in 50 mM GTA buffer having various pH. The relative activities were shown in FIG. 5 defining the activities before storage as 100. The *Aspergillus oryzae* EAP, *Aspergillus nidulans* EAP, *Aspergillus niger* EAP and the yeast EAP exhibited at least 90% remaining activity after storing them at 0° C. for 24 hours in the range of pH6.0-10.0. The coryneform bacterial EAP exhibited at least 90% remaining activity after storing it at 0° C. for 24 hours in the range of pH7.0-8.0.

(vi) Peptide Length-Dependent Reaction Profile

The activities of the aminopeptidases were determined by using various substrates which had different amino acid residues and Glu at the N-terminals instead of using the Glu-Glu substrate. Briefly, to 0.16 ml of 5 mM each substrate (in 50 mM HEPES buffer, pH7.5) 0.02 ml of the enzyme solution was added to react for 10 minutes at 37° C. and 0.02 ml of 20% acetic acid was added to stop the reaction. The free Glu content was determined by Glutamic Acid Measurement Kit (Yamasa Shouyu). One unit of the activity was defined as the enzyme activity that liberated 1 micromole of Glu per 1 minute and the specific activities, which were the activities per weight, were calculated and shown in FIG. 6. The substrates used were the following four species: (a) Glu-Glu (Bachem), (b) Glu-His-Phe-Arg-Trp-Gly (Bachem) (SEQ ID NO:39), (c) Glu-Gly-Val-Tyr-Val-His-Pro-Val (Bachem) (SEQ ID NO:40) and (d) Asp- Glu (Bachem). As shown in FIG. 6, the activities inclined to be high for longer peptides compared with the activities for di-peptides.

Example 8

Effects of Enhancing the Taste of Natural Seasonings

To 1 ml of "Honzukuri Ichiban-Dashi Kiwami Katsuo" (Ajinomoto) 0.1 mg of each purified EAP was added to allow the reaction at 37° C., and samples were sequentially taken at 0, 60 and 120 minutes after the reaction. The free Glu content was determined by Glutamic Acid Measurement Kit (Yamasa Shouyu). The samples taken at 120 minutes of the reaction were diluted 20-fold and tested by a sensory evaluation.

The *Aspergillus oryzae* EAP, *Aspergillus niger* EAP and the yeast EAP increased the free Glu content by about 300 mg/l after 120 minute-reaction (FIG. 7). On the other hand, the increase by the coryneform bacterial EAP was about ⅓ of them. The intensity of umami was proportional to the free Glu content as measured by the sensory evaluation (Table 2).

| Intensity of umami after reaction (120 min.) | | | |
|---|---|---|---|
| *Aspergillus oryzae* EAP | *Aspergillus niger* EAP | Coryneform bacterial EAP | Yeast EAP |
| +++ | +++ | + | +++ |

—: no change ; +: slight increase ; ++: increase ; +++: significant increase

Example 9

Production of Protein Hydrolysates Having Intense Taste

A solution of 5% isolated soybean protein was adjusted to pH 8.0 and was heat-denatured by autoclave sterilization at 121° C. for 20 minutes. To the resulting protein solution UMAMIZYME™ (Amano Enzyme) and PROTEASE M™ (Amano Enzyme) was added at 1% by weight of soybean, proteins, and reacted at 50° C. for 48 hours. The *Aspergillus* EAP was then added to the mixture at 0.2% (by weight) to react at 37° C. for 24 hours. Free Glu content of the *Aspergillus oryzae* EAP-added sample and that of the non-added sample were determined by using Glutamic Acid Measurement Kit (Yamasa Shouyu). As a result, it was revealed that the free Glu content increased about 1.5-fold by the addition of *Aspergillus oryzae* EAP (FIG. 8).

To a soybean protein solution which had been similarly processed 1% ALCALASE™ (Novozymes) was added and reacted at 50° for 48 hours. Then, the ALCALASE™ was inactivated at 121° C. for 10 minutes, 1% FLA-VOURZYME™ (Novozymes) was then added to react under the condition of 37° for 24 hours. After that, *Aspergillus oryzae* EAP was added the reaction was further conducted at 37° C. for 24 hours. Free Glu content of the *Aspergillus oryzae* EAP added sample and that of the non-added sample were determined the free Glu content increased about 2.2-fold by the addition of *Aspergillus oryzae* EAP (FIG. 9).

Example 10

Improvement in Taste and/or Flavour of Dairy Products

The effects of adding *Aspergillus oryzae* EAP to a cheese were studied. The same raw milk (about 35L) was used as the raw material milk. The milk was defatted according to the conventional process and the fat ratio was adjusted to 3%. A defined amount of starter lactic acid bacteria was added to the raw material milk and the milk was heated to 32° C. Chymosin was added to the material at an amount of 0.003% of the material. After confirming the coagulation of the raw material milk, the coagulated milk was cut and stirred to remove about ⅓ of the whey. It was then heated to 34° C. slowly at a rate of 1° C./2 min, stirred and ⅓ of the whey was further removed. After that, it was slowly heated to 38° C. at a rate of 1° C./2 min, stirred for 1 hour and was subjected to whey off to obtain a curd. The amount of the added *Aspergillus oryzae* EAP was 0.5 mg per 100 g of the curd. To the control group no enzyme was added. The enzyme was directly added to 1500 g of the curd and the mixture was sufficiently stirred to become homogeneous. The lactic acid bacteria used were a quadruple combined lactic cocci (Gouda cheese) from Christian Hansen. NaCl was also added to the curd at 3% by weight. For high temperature ripening (10° C.) sodium nitrate was added to the raw material milk at 0.002%. After pre-drying until the next morning of the production date, about 375 g of curd was placed in a mold. The ripening was conducted by storing in a ripening chamber at 10° C. after vacuum packaging to shorten the experiment period and the samples were evaluated by sensory evaluation after storing them for 140 days.

The significant difference in ripening rate (solubilized nitrogen ratio) was not observed by adding the *Aspergillus oryzae* EAP as compared with the non-enzyme added control. The solubilized nitrogen rate was calculated as the ratio of the nitrogen content in the soluble fraction in 12% trichloroacetic acid to the total nitrogen content. On the other hand, the increase in the free glutamic acid content caused by adding the *Aspergillus oryzae* EAP was 1 mg/100 g cheese. From the results of sensory evaluation, the effects were observed including the enhancement of the flavour of cheese, the improved total balance and the creamy taste and the like. Additionally, the bitterness of cheese was eliminated by the addition of the *Aspergillus oryzae* EAP, which was supposed to be the effect due to the increase in the free glutamic acid content.

Example 11

Improvement of Taste and/or Flavour of Beverage (I)

Tomatoes (Momotarou and petit tomato) were washed and crushed by a mixer for home use to prepare a tomato juice. To 100 ml of the juice the *Aspergillus oryzae* EAP was added at a concentration of 3 mg/l. As a control, a pre-heated *Aspergillus oryzae* EAP was also added. The reaction was conducted at 37° C. for 1 hour and after the completion of the reaction the juice was subjected to a sensory evaluation.

The free glutamic acid content increased about 3% by the treatment with the *Aspergillus oryzae* EAP. However, since 0.2% (w/w) free glutamic acid inherently exists in a tomato juice, the affection of the 3% increase of the free glutamic acid content on the umami intensity was not observed. On the other hand, sweetness was enhanced and acidity was repressed in the enzyme-treated group, and therefore an unpreferable taste characteristic to a tomato juice was reduced. Such improving effects on the taste and/or on the flavour were not observed for the control group. The effects of the *Aspergillus oryzae* EAP on tomatoes were remarkable for petit tomatoes or for well-ripened tomatoes.

Example 12

Improvement of Taste and/or Flavour of Beverage (II)

The *Aspergillus oryzae* EAP was added to 100 ml of a commercially available soybean milk beverage (Domestic soybean milk; Taishi Shokuhin Kougyou Co.) to be a concentration of 3 mg/l. The previously heat-inactivated peptidase was used as a control. These were reacted at 37° C. for 1 hour and then subjected to sensory evaluation.

An increase of the glutamic acid content of the soybean milk by *Aspergillus oryzae* EAP treating was not observed. Thus, the enhancement of umami was not observed. However, grass-like smell (smell of hexanal) characteristic for soybean milk was weakened as compared with the control group and the soybean milk became milder, which confirmed the taste- and/or flavour-improving effects on soybean milk.

According to the present invention, a method for producing a food and/or a beverage having a high glutamic acid content and enhanced flavour. Particularly, it will be possible to hydrolyze hydrolysis-resistant peptides such as Glu-Glu, which exist under the condition such as soy sauce brewing process, and it is also possible to produce a flavouring liquid having intense taste. The free Glu content in protein hydrolysates may be increased by using the enzyme together with marketed protease preparations or peptidase preparations. The reason is considered to be that the marketed protease preparations and peptidase preparations contain little enzymes having EAP-like activity, and thus hydrolysis-resistant peptides such as Glu-Glu remain intactly. According to the present invention, it is possible to further enhance the taste of a food and/or a beverage including soy source and protein hydrolysates by using the aminopeptidase EAP.

What is claimed is:

1. A method for producing a food and/or beverage comprising reacting a protein in the food and/or beverage with an aminopeptidase wherein the aminopeptidase is encoded by the nucleic acid sequence of SEQ ID NO:6 or by a polynucleotide homolog that varies from SEQ ID NO: 6 as a result of degeneracy in the genetic code, wherein said polynucleotide homolog encodes the same amino acid sequence as the polynucleotide sequence of SEQ ID NO:6.

2. The method according to claim 1, wherein the aminopeptidase is encoded the nucleotide sequence shown in SEQ ID NO:6.

3. The method according to claim 1, wherein the aminopeptidase is produced by a microorganism transformed with polynucleotide having the sequence shown in SEQ ID NO:6.

4. The method according to claim 1, wherein the foods and/or beverages are selected from the group consisting of protein hydrolysates, cheeses, tomato juice containing beverages and soy milk-containing beverages.

5. The method according to claim 1, wherein reacting said protein in a food and/or beverage with an aminopeptidase further comprises the presence of a protease.

6. The method according to claim 5, wherein said aminopeptidase is encoded by said polynucleotide homolog.

7. The method according to claim 5, wherein said protease is a proteolytic enzyme produced by *Aspergillus* or *Bacillus*.

8. The method according to claim 5, wherein said protease is selected from the group of enzyme preparations consisting of UMAMIZYME™, PROTEASE M™, FLAVOURZYME™ and ALCALASE™.

9. A method for producing a food and/or beverage comprising reacting a protein in the food and/or beverage with an aminopeptidase, wherein the aminopeptidase has the amino acid sequence of SEQ ID NO:7 or a homolog thereof, wherein said homolog thereof has an amino acid sequence of SEQ ID NO:7 having from one to ten amino acid replacements, deletions or additions, or combinations thereof and wherein said aminopeptidase homolog:

(a) has an activity of catalyzing the reaction of specifically releasing a glutamic acid or an aspartic acid from the N-terminal of a peptide and/or a protein;

(b) has 50% or more of the activity defined in clause (a) at pH 6.0-9.0 as compared with the activity at pH 7.5;

(c) has 40% or more of the activity defined in clause (a) after heating at 25-60° C., pH 7.5 for 30 minutes as compared with the activity of the aminopeptidase prior to heating;

(d) has a molecular weight of about 40-60 kD as measured by SOS-PAGE and about 300-480 kD as measured by native-PAGE; and (e) has a hydrolyzing activity of 5 U/mg or more toward Glu-Glu dipeptide, wherein one U (unit) is an enzyme activity that liberates 1 micromole of Glu per 1 minute at 37° C.

10. The method according to claim 9, wherein the aminopeptidase has the amino acid sequence of SEQ ID NO: 7.

11. The method according to claim 9, wherein the aminopeptidase is said homolog thereof.

12. The method according to claim 9, wherein the foods and/or beverages are selected from the group consisting of protein hydrolysates, cheeses, tomato juice containing beverages and soy milk-containing beverages.

13. The method according to claim 9, wherein reacting said protein in a food and/or beverage with an aminopeptidase further comprises the presence of a protease.

14. The method according to claim 13, wherein said protease is a proteolytic enzyme produced by *Aspergillus* or *Bacillus*.

15. The method according to claim 14, wherein said protease is selected from the group of enzyme preparations consisting of UMAMIZYME™, PROTEASE M™, FLAVOURZYME™ and ALCALASE™.

* * * * *